US012745934B2

(12) United States Patent
Margiott et al.

(10) Patent No.: US 12,745,934 B2
(45) Date of Patent: Sep. 29, 2026

(54) WIRELESS OXYGEN SATURATION SENSOR

(71) Applicant: ViOptix, Inc., Newark, CA (US)

(72) Inventors: Alex Michael Margiott, Dunbarton, NH (US); Scott E. Coleridge, New York, NY (US); Mark Lonsinger, San Jose, CA (US)

(73) Assignee: ViOptix, Inc., Newark, CA (US)

( * ) Notice: Subject to any disclaimer, the term of this patent is extended or adjusted under 35 U.S.C. 154(b) by 0 days.

(21) Appl. No.: 19/036,800

(22) Filed: Jan. 24, 2025

(65) Prior Publication Data

US 2025/0241564 A1 Jul. 31, 2025

Related U.S. Application Data

(60) Provisional application No. 63/624,782, filed on Jan. 24, 2024.

(51) Int. Cl.
*A61B 5/1455* (2006.01)
*A61B 5/00* (2006.01)

(52) U.S. Cl.
CPC ........ *A61B 5/14551* (2013.01); *A61B 5/0002* (2013.01); *A61B 5/742* (2013.01)

(58) Field of Classification Search
CPC .................................................... A61B 5/1455
See application file for complete search history.

(56) References Cited

U.S. PATENT DOCUMENTS

| | | | |
|---|---|---|---|
| 6,134,460 | A | 10/2000 | Chance |
| 6,748,254 | B2 | 6/2004 | O'Neil et al. |
| 7,355,688 | B2 | 4/2008 | Lash et al. |
| 7,525,647 | B2 | 4/2009 | Lash et al. |
| 7,538,865 | B2 | 5/2009 | Lash et al. |
| 7,657,293 | B2 | 2/2010 | Lash et al. |
| 7,796,247 | B2 | 9/2010 | Mao et al. |
| 8,052,605 | B2 | 11/2011 | Muller et al. |
| 8,308,784 | B2 | 11/2012 | Streeter et al. |
| 8,315,685 | B2 | 11/2012 | Arizaga Ballesteros |
| 8,622,918 | B1 | 1/2014 | Mao et al. |

(Continued)

FOREIGN PATENT DOCUMENTS

| | | | |
|---|---|---|---|
| CN | 108344524 | B | 8/2021 |
| JP | 4465271 | B2 | 5/2010 |

(Continued)

OTHER PUBLICATIONS

International Search Report and the Written Opinion of the International Searching Authority for PCT/US2025/0121969 dated May 28, 2025, 14 pages.

(Continued)

*Primary Examiner* — Marjan Fardanesh
(74) *Attorney, Agent, or Firm* — Aka Chan LLP

(57) ABSTRACT

An oximeter sensor probe system includes a sensor probe unit that is connected by a wire to a sensor probe electronic module. The sensor probe electronic module connects wirelessly to a medical device console, which can be a phone, tablet, or other mobile device. And the mobile device can connect to a network or the Internet (e.g., the Cloud). Alternatively, the sensor probe electronic module can directly to the network or the Internet directly without a medical device console. The medical device console can execute an application and show on its display oxygen saturation and related measurements obtained through the sensor probe unit.

26 Claims, 45 Drawing Sheets

(56) References Cited

U.S. PATENT DOCUMENTS

| | | | |
|---|---|---|---|
| 8,929,967 | B2 | 1/2015 | Mao et al. |
| 9,591,999 | B2 | 3/2017 | Schenkman et al. |
| 10,028,682 | B2 | 7/2018 | Thiele |
| 10,188,872 | B2 | 1/2019 | De Taboada et al. |
| 10,209,178 | B2 | 2/2019 | Carvalho Sousa et al. |
| 10,321,862 | B2 | 6/2019 | Dalene et al. |
| 10,335,074 | B2 | 7/2019 | Mao et al. |
| 10,548,526 | B1 | 2/2020 | Mao et al. |
| 10,750,986 | B2 | 8/2020 | Bechtel et al. |
| 10,758,743 | B2 | 9/2020 | De Taboada et al. |
| 10,932,708 | B2 | 3/2021 | Bechtel et al. |
| 11,273,319 | B2 | 3/2022 | De Taboada et al. |
| 11,439,330 | B2 | 9/2022 | Bechtel et al. |
| 11,662,309 | B2 | 5/2023 | Magnussen et al. |
| 12,514,474 | B2 | 1/2026 | Shadgan et al. |
| 2007/0078316 | A1 | 4/2007 | Hoarau et al. |
| 2007/0093698 | A1 | 4/2007 | Goldberger et al. |
| 2009/0163775 | A1 | 6/2009 | Barrett et al. |
| 2010/0105998 | A1 | 4/2010 | Benni |
| 2011/0060266 | A1 | 3/2011 | Streeter et al. |
| 2013/0225955 | A1 | 8/2013 | Schenkman et al. |
| 2014/0276014 | A1 | 9/2014 | Khanicheh et al. |
| 2014/0343384 | A1 | 11/2014 | Floyed et al. |
| 2015/0265214 | A1 | 9/2015 | De Kok et al. |
| 2015/0282747 | A1 | 10/2015 | Thiele |
| 2016/0235303 | A1 | 8/2016 | Fleming et al. |
| 2016/0278675 | A1 | 9/2016 | Benni |
| 2017/0209083 | A1 | 7/2017 | Zarandi et al. |
| 2017/0215780 | A1 | 8/2017 | Mao et al. |
| 2018/0042513 | A1 | 2/2018 | Connor |
| 2018/0214026 | A1 | 8/2018 | Goodall et al. |
| 2018/0214066 | A1 | 8/2018 | Goodall et al. |
| 2019/0150811 | A1 | 5/2019 | Evans et al. |
| 2019/0206538 | A1 | 7/2019 | Xing et al. |
| 2019/0234869 | A1 | 8/2019 | Sajjadi et al. |
| 2019/0254536 | A1 | 8/2019 | Nahman et al. |
| 2021/0259618 | A1 | 8/2021 | Seidman et al. |
| 2022/0218272 | A1 | 7/2022 | Pollonini et al. |
| 2024/0000383 | A1 | 1/2024 | Connor |

FOREIGN PATENT DOCUMENTS

| | | | |
|---|---|---|---|
| KR | 102000866 | B1 | 7/2019 |
| WO | 2012109661 | A2 | 8/2012 |
| WO | 2013166461 | A1 | 11/2013 |
| WO | 2015/054681 | A1 | 4/2015 |
| WO | 2018168145 | A1 | 9/2018 |
| WO | 2021042215 | A1 | 3/2021 |
| WO | 2022/087374 | A1 | 4/2022 |

OTHER PUBLICATIONS

U.S. Appl. No. 63/094,999, filed Oct. 22, 2020, available Apr. 28, 2022, Macewan et al., 57 pages.

"Pulse Oximetry Basic Principles and Interpretation," Iowa Head and Neck Protocols, University of Iowa Health Care, Oct. 3, 2017, 4 pages.

Seidl, M., "Analog Front-End Design With Texas Instruments' Tooling Landscape," Texas Instruments, Mar. 2022, 20 pages.

King, I., "High-Performance Analog Front Ends," Analog edge, Expert tips, tricks, and techniques for analog designs, vol. 4(1), 2011, 6 pages.

Pratt, M.K., "Top 12 most commonly used IoT protocols and standards," IoT Agenda, Tech Accelerator, Ultimate IoT implementation guide for businesses, Jul. 12, 2023, 9 pages.

Amiri, A.R., et al., Intraoperative Assessment of Human Spinal Cord Perfusion using near Infrared Spectroscopy with Indocyanine Green Tracer Technique, Spine J., Dec. 2013, 13(12), pp. 1818-1825.

Arifler, D., et al., Optimal Wavelength Combinations for Near-Infrared Spectroscopic Monitoring of Changes in Brain Tissue Hemoglobin and Cytochrome C Oxidase Concentrations, Biomed Opt Express, Mar. 1, 2015, 6(3), pp. 933-947.

Boushel, R., et al., Monitoring Tissue Oxygen Availability with near Infrared Spectroscopy (NIRS) in Health and Disease, Scand J Med Sci Sports, 2001: 11, pp. 213-222.

Busch, D.R. et al., Laser Safety in Fiber-Optic Monitoring of Spinal Cord Hemodynamics: A Preclinical Evaluation, J Biomed Opt, 2018, 23:065003.

Casha, S., et al., A Systematic Review of Intensive Cardiopulmonary Management after Spinal Cord Injury, J Neurotrauma, 2011, 28, pp. 1479-1495.

Delphy, D. T., et al., Quantification in tissue near-infrared spectroscopy, Phil. Trans. R. Soc. Lond. B 1997, 352, pp. 649-659.

Demir, A. et al., Near-infrared Spectroscopy Monitoring of the Spinal Cord during Type B Aortic Dissection Surgery, J Card Surg., May 2013, 28(3), pp. 291-294.

Dix, L.M.L., et al., Monitoring Cerebral Oxygenation in Neonates: An Update, Frontiers in Pediatrics, vol. 5(46), Mar. 14, 2017, doi: 10.3389/pfed.2017.00046, 9 pgs.

Etz, D.C., et al., Spinal Cord Ischemia in Open and Endovascular Thoracoabdominal Aortic Aneurysm Repair: New Concepts, J Cardiovasc Surg (Torino), Apr. 2014: 55(2 Suppl 1), pp. 159-168.

Hawryluk, G., et al., Mean Arterial Blood Pressure Correlates with Nuerological Recovery after Human Spinal Cord Injury: Analysis of High Frequency Physiologic Data, Journal of Neurotrauma, 32:1958-1967, Dec. 15, 2015.

Kogler, A.S., et al., Fiber-optic Monitoring of Spinal Cord Hemodynamics in Experimental Aortic Occlusion, Anesthesiology, Dec. 2015, 123(6), pp. 1362-1373.

Lemaire, S.A., et al., Transcutaneous near-infrared Spectroscopy for Detection of Regional Spinal Ischemia during Intercostal Artery Ligation: Preliminary Experimental Results, J Thorac Cardiovasc Surg., Nov. 2006, 132(5), pp. 1150-1155.

Macnab, A.J., et al., Near Infrared Spectroscopy for Intraoperative Monitoring of the Spinal Cord, Spine (Phila Pa 1976), Jan. 1, 2002, 27(1), pp. 17-20.

Matcher, S.J., et al., Performance Comparison of Several Published Tissue Near-Infrared Spectroscopy Algorithms, Anal. Biochem., May 1995, 227(1), pp. 54-68.

Mesquita, R. C., et al., Optical Monitoring and Detection of Spinal Cord Ischemia, PLoS One, Dec. 16, 2013, 8 (12).

Moerman, A., et al., Near-infrared Spectroscopy for Monitoring Spinal Cord Ischemia during Hybrid Thoracoabdominal Aortic Aneurysm Repair, J Endovasc Ther., Feb. 2011, 18(1), pp. 91-95.

Ploumis, A. et al., A Systematic Review of the Evidence Supporting a Role for Vasopressor Support in Acute SCI, Spinal Cord, 2010, 48(5), pp. 356-362.

Redlin, M., et al., Detection of Lower Torso Ischemia by near-infrared Spectroscopy during Cardiopulmonary Bypass in a 6.8-kg Infant with Complex Aortic Anatomy, Ann Thorac Surg., Jul. 2006, 82(1), pp. 323-325.

Shadgan, B., et al., Optical Assessment of Spinal Cord Tissue Oxygenation Using a Miniaturized Near Infrared Spectroscopy Sensor, Journal of Neurotrauma, 2019, 36, pp. 3034-3043.

Suzuki, S., et al., Tissue Oxygenation Monitor Using NIR Spatially Resolved Spectroscopy, Proc SPIE 3597, Optical Tomography and Spectroscopy of Tissue III, Jul. 19, 1999.

Tachtsidis, I., et al., Relationship between Brain Tissue Haemodynamics, Oxygenation and Metabolism in the Healthy Human Adult Brain during Hyperoxia and Hypercapnea, Adv. Exp. Med. Biol., 2009, 645, pp. 315-320.

Tator, C.H. et al., Review of the Secondary Injury Theory of Acute Spinal Cord Trauma with Emphasis on Vascular Mechanisms, J Neurosurg, Jul. 1991, 75(1), pp. 15-26.

Tsiakaka, O., et al., Toward the Monitoring of the Spinal Cord: A Feasibility Study, Microelectronics Journal, 2019, 88, pp. 145-153.

Wyser, D., et al., Wearable and Modular Functional near-infrared Spectroscopy Instrument with Multidistance Measurements at Four Wavelengths, Neurophotonics, 2017, 4(4), 041413.

WIRELESS OXYGEN SATURATION SENSOR

CROSS-REFERENCE TO RELATED APPLICATIONS

This application claims the benefit of U.S. patent application 63/624,782, filed Jan. 24, 2024, which is incorporated by reference along with all other references cited in this application.

BACKGROUND OF THE INVENTION

This invention relates to medical devices, and more specifically, to devices and techniques to measure oxygen saturation.

Oxygen saturation or StO2 is a relative measure of the concentration of oxygen that is dissolved or carried in a given medium, such as blood or tissue, as a proportion of the maximal concentration that can be dissolved in that medium at the given temperature. In medicine, oxygen saturation is the fraction of oxygen-saturated hemoglobin relative to total hemoglobin (unsaturated and saturated) in the blood. The human body maintains a specific balance of oxygen in the blood. Normal arterial blood oxygen saturation levels in humans are typically 97-100 percent. If the level falls below 90 percent, it is considered low and called hypoxemia. Arterial blood oxygen levels below 80 percent may compromise organ function, such as the brain and heart. Continued low oxygen levels may lead to respiratory or cardiac arrest. Oxygen saturation is an important measure of human health and well-being.

Oximeters are medical devices used to measure oxygen saturation of tissue in humans and living things for various purposes. For example, oximeters are used for medical and diagnostic purposes in hospitals and other medical facilities (e.g., surgery, patient monitoring, or ambulance or other mobile monitoring for, e.g., hypoxia); sports and athletics purposes at a sports arena (e.g., professional athlete monitoring); personal or at-home monitoring of individuals (e.g., general health monitoring, or person training for a marathon); and veterinary purposes (e.g., animal monitoring).

Pulse oximeters and tissue oximeters are two types of oximeters that operate on different principles. A pulse oximeter uses a pulse to make measurements. A pulse oximeter typically measures the absorbance of light due to pulsing arterial blood. In contrast, a tissue oximeter does not need a pulse in order to function, and can be used to make oxygen saturation measurements of a tissue flap that has been disconnected from a blood supply or of tissue, such as internal organs that are connected to a blood supply.

Human tissue, as an example, includes a variety of light-absorbing molecules. Such chromophores include oxygenated hemoglobin, deoxygenated hemoglobin, melanin, water, lipid, and cytochrome. Oxygenated hemoglobin, deoxygenated hemoglobin, and melanin are the most dominant chromophores in tissue for much of the visible and near-infrared spectral range of electromagnetic waves. Light absorption differs significantly for oxygenated and deoxygenated hemoglobins at certain wavelengths of light. Tissue oximeters can measure oxygen levels in human tissue by exploiting these light-absorption differences.

Despite the success of existing oximeters, there is a continuing desire to improve oximeters by, for example, improving form factor; improving measurement accuracy; reducing measurement time; lowering cost; reducing size, weight, or form factor; reducing power consumption; improve network or wireless connectivity, and for other reasons, and any combination of these.

In particular, assessing a patient's oxygenation state, at both the regional and local level, is important as it is an indicator of the state of the patient's local tissue health. Thus, oximeters are often used in clinical settings, such as during surgery and recovery, where it may be suspected that the patient's tissue oxygenation state is unstable. For example, during surgery, oximeters should be able to quickly deliver accurate oxygen saturation measurements under a variety of nonideal conditions. While existing oximeters have been sufficient for postoperative tissue monitoring where absolute accuracy is not critical and trending data alone is sufficient, accuracy is, however, important during surgery in which spot-checking can be used to determine whether tissue might remain viable or needs to be removed.

Therefore, there is a need for improved tissue oximeter sensors and devices and methods of using and making measurements using these sensors.

BRIEF SUMMARY OF THE INVENTION

An oximeter sensor probe system includes a sensor probe unit that is connected by a wire to a sensor probe electronic module. The sensor probe electronic module connects wirelessly to a medical device console, which can be a phone, tablet, other mobile device, or other devices, and the device or mobile device can connect to a network or the Internet (e.g., the Cloud). Alternatively, the sensor probe electronic module can directly to the network or the Internet directly without a medical device console. The medical device console can execute an application and show on its display oxygen saturation and related measurements obtained through the sensor probe unit.

ViOptix, Inc. is a pioneer and worldwide leader in the field of tissue oximetry and tissue oximeters. ViOptix's products include T.Ox, TOx Remote, and Intra. Ox, which are described at ViOptix's Web site, www.vioptix.com. The ViOptix Web site, user's manuals, and other publicly available documents on its products as of the filing date of this patent application are incorporated by reference.

In an implementation, a form factor of the sensor probe unit is the same or similar to the form factor of the T.Ox small patch sensor having a rectangular shape with right-angle or rounded corners where the longest dimension of the width and the length of the sensor is no more than one centimeter, 2 centimeters, 3 centimeters, 4 centimeters, or 5 centimeters. In some of these embodiments, the size of the sensor is about 5 millimeters×5 millimeters with manufacturing tolerances. The operation and capabilities of the oximeter sensor probe system of this application are similar to T.Ox, but without the need for a T.Ox console. Any mobile device (e.g., running Apple's iOS or Google's Android operating system) can run an application and interface with the sensor probe electronic module via Bluetooth or other wireless technology (such as an application or interface provided via a USB or Wi-Fi dongle). The application on the mobile device will display the oxygen saturation readings or a real-time oxygen saturation graph that are updated periodically, such as every 4 seconds. In the application, a user can to set custom alarms or alerts that occur when the measured oxygen saturation exceed or fall below a certain level.

The following are incorporated by reference along with all other references cited in this application: all patent applications of ViOptix, Inc. published or issued in the U.S.

or abroad with a filing date before the filing date of the present application, including U.S. Pat. No. 6,587,703, filed Jun. 7, 2001; U.S. Pat. No. 7,657,293, filed Sep. 8, 2005; U.S. Pat. No. 8,352,006, filed Jun. 24, 2007; U.S. Pat. No. 7,525,647, filed Dec. 21, 2007; U.S. Pat. No. 8,929,967, filed Apr. 28, 2008; U.S. Pat. Nos. 7,553,285, 7,569,017, 7,582,060, filed Jul. 9, 2008; U.S. Pat. No. 10,548,526, filed Jan. 6, 2014; 10,335,074, Jan. 5, 2015; U.S. Pat. No. 11,457,812, filed Aug. 6, 2019.

Other objects, features, and advantages of the present invention will become apparent upon consideration of the following detailed description and the accompanying drawings, in which like reference designations represent like features throughout the figures.

DETAILED DESCRIPTION OF THE INVENTION

Figure 1:
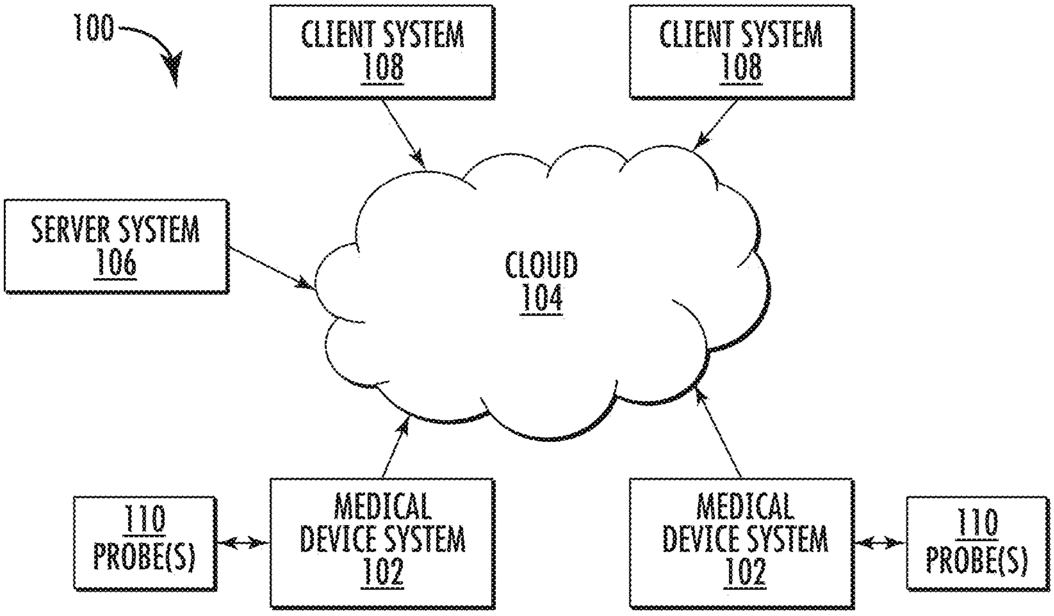
FIG. 1 shows an architectural diagram of a computing environment to which various techniques described herein may be applied in some embodiments.

Some embodiments of the present invention relate to the field of medical devices, their use and manufacture. Some embodiments relate generally to optical imaging systems that monitor oxygen levels in tissue. These embodiments relate to monitoring oxygen levels to determine the viability of flaps before and after a flap transplant. Some embodiments relate to medical devices and techniques for diagnosing intestinal ischemia or bowel ischemia.

Flap surgery is a type of plastic or reconstructive procedure that enables tissue from one area of a body to effectively be moved to another area of the body. A flap is a section of living tissue with a blood supply that may be transported from a "donor" area of a body to a new area of the body, e.g., an area onto which the flap is to be transplanted. A flap may be transplanted to an area of the body that has lost, for example, skin, fat, or muscle. Flap surgery generally restores some skin, fat, muscle movement, or skeletal support (e.g., in areas of the patient's body that have lost bone(s)) to an area in which muscle movement, fat, bone(s), or skin coverage may have been missing or lost.

There are many different kinds of flaps that are used in flap surgery. A local flap is typically a piece of skin with underlying tissue that is located next to a wound. The local flap is repositioned over the wound while remaining attached at one end such that the local flap may be nourished by its original blood supply. A regional flap is generally a section of tissue that is attached by a specific blood vessel or specific blood vessels. When lifted, the regional flap uses a relatively narrow attachment to the donor, or original, site to receive a blood supply from the specific blood vessel or vessels, e.g., a tethered artery and vein. A musculocutaneous flap, e.g., a muscle and skin flap, is typically used when an area to be covered by the flap is relatively large and requires a significant blood supply. A musculocutaneous flap is often used in breast reconstruction surgery, and remains tethered to its original blood supply. A microvascular free flap is a flap of tissue and skin that is detached, along with blood vessels, from an original site of a body and reattached to a new site in the body. As a microvascular free flap is completely detached from an original site, the attachment of such a flap to a new site requires reattaching severed blood vessels at the new site.

Blood flow through transplanted flaps may change drastically in the period of time substantially immediately after a transplant is completed. A transplanted flap may sometimes die, e.g., transplanted tissue may die, when the blood flow through the transplanted flap is compromised. For example, a blood clot in the transplanted flap or a pinched vein in the transplanted flap may cause the transplanted flap to die. Currently, to monitor a transplanted flap to determine whether blood flow through a transplanted flap is adequate to sustain the transplanted flap, laser Doppler flap monitoring may be used. Laser Doppler flap monitoring, or laser Doppler flowmetry, allows Doppler measurements to be made near blood vessels of the transplanted flap. Interpretation of the Doppler measurements may enable potential flap failures to be detected before clinical signs of failure, e.g., discoloration of the transplanted flaps, manifest themselves.

Though laser Doppler flap monitoring may be effective for enabling potential flap failures to be detected in some instances, laser Doppler systems are generally able to make measurements on relatively large vessels, and are unable to measure regional perfusion in the micro-vasculature within a skin flap. Even though flow may be detected in larger vessels when laser Doppler flap monitoring is employed, distal flap tissue may be under-perfused and, as a result, may die.

As an alternative to laser Doppler flap monitoring, some surgeons may nick a transplanted flap in various places to assess the blood flow therethrough. Nicking a transplanted flap is invasive and does not always allow for an accurate determination of the viability of a transplanted flap, as assessing the blood flow in such a manner is highly subjective. Further, it may be very difficult to determine where in a transplanted flap to make a nick, e.g., a surgeon may inadvertently fail to make a nick near a blood vessel that is pinched.

Therefore, what is needed is a method and an apparatus that allows the viability of a transplanted flap to be accurately determined. That is, what is desired in some embodiments is a system which is non-invasive and relatively non-subjective, and allows the blood flow through a flap to be accurately assessed.

Intestinal ischemia or bowel ischemia is a term used to describe the result of a variety of disorders that cause insufficient blood flow to the gastrointestinal tract. Ischemia can be localized to a relatively small part of the small intestine or large intestine, or it may be widespread and involve both types of intestines. Moreover, ischemic necrosis (e.g., localized death of living cells) of the intestine can be superficial, involving mucosa (inner lining) to full thickness transmural necrosis. Intestinal ischemia can manifest with symptoms ranging from a mild, short-lived abdominal pain, to bloody diarrhea or a more serious situation that may require surgery.

There are several causes for intestinal ischemia. The most common cause is diminished intestine perfusion resulting from low cardiac output. It is often seen in patients with cardiac disease or in patients with prolonged shock of any etiology. Another cause of intestinal ischemia is an occlusive disease of the vascular supply to the intestine. The occlusive disease can result from atheroma (e.g., a deposit of lipid-containing plaques an inner wall layer of an artery), thrombosis (e.g., a stationary clot attached to the blood vessel wall), or embolism (e.g., a migrating blood clot that forms a blockage) in which the collateral circulation is not adequate to maintain intestine integrity. Another common form of intestinal ischemia is ischemic colitis, in which inflammation and injury of the colon result from inadequate blood supply.

When ischemic bowel disease severely damages tissue in the intestine, the damaged tissue must be surgically removed. The remaining tissue can be sewn together, typically in end-to-end anastomosis (e.g., surgical connection of two severed tubular organ parts). Prior to resection, a surgeon must distinguish between viable and nonviable intestinal tissue. Typically, the surgeon relies on subjective visual inspection such as tissue color to determine which intestinal tissue is viable. Such a decision is often made hastily during operation. Further, such visual inspection has been shown to be unreliable in determining long-term viability of intestinal tissue.

Determining intestine viability is difficult but important for patients with ischemic bowel disease. If nonviable tissue is not removed, the result can be fatal. Removing too much intestine can also lead to severe complications. Thus, there is a need for better medical devices and systems that can determine the oxygenation state of the entire thickness of an intestinal tissue as well as other tissues. Improved devices and system can better assist doctors in determining viability of an intestinal tissue, and the doctors can make a better-informed decision regarding a treatment plan for the patient. Some embodiments of the present invention meet this and other needs.

Moreover, some embodiments of the present invention relate to methods of diagnosing peripheral vascular disease (PVD) using measured changes in oxygen saturation in tissue. More specifically, the invention relates to diagnosing peripheral vascular disease from an analysis of oxygen saturation during recovery from, for example, ischemia (reduced or stoppage of blood flow), PVD (peripheral vascular disease), exercises for enhancing metabolic demands, and others.

Peripheral vascular disease is a condition that is exemplified by a narrowing of blood vessels to internal organs and muscles. Patients with peripheral vascular disease are four times more likely to have a myocardial infarction and three times more likely to have a stroke. The five-year mortality rate for people with peripheral vascular disease is 30 percent. Peripheral vascular disease affects 20 percent of the elderly and 40 percent of diabetics.

Unfortunately, it has been estimated that 8-12 million people in the United States are affected with this disease and the numbers are growing at a rate of five percent a year. Although these numbers show that peripheral vascular disease is a fairly common disease, peripheral vascular disease is often not diagnosed or is misdiagnosed. It has been estimated that 71 percent of physicians overlook a peripheral vascular disease condition in their patients.

As provided for in some embodiments of the present invention, it would be beneficial to have innovative techniques for diagnosing peripheral vascular disease. Additionally, it would be beneficial to have techniques of diagnosing peripheral vascular disease with relatively high accuracy rates.

Some embodiments of the present invention relate generally to optical imaging systems that monitor oxygen levels in tissue. More specifically, the present invention relates to optical probes that include sources and detectors that are not symmetrically arranged on sensor heads of the optical probes.

Near-infrared spectroscopy has been used for noninvasive measurement of various physiological properties in animal and human subjects. The basic principle underlying the near-infrared spectroscopy is that physiological tissues include various highly-scattering chromophores to the electromagnetic waves (e.g., near-infrared waves) with relatively low absorption. Many substances in a medium may interact or interfere with the light waves (e.g., electromagnetic waves such as visible or near-infrared waves) propagating therethrough. Human tissues, for example, include numerous chromophores such as oxygenated hemoglobin (a form of hemoglobin that carries oxygen from the lungs to body tissues), deoxygenated hemoglobin (a form of hemoglobin that has released its oxygen to tissues and is no longer bound to oxygen), water, lipid, and cytochrome, where the hemoglobin are the dominant chromophores in the spectrum range of approximately 700 nanometers to approximately 900 nanometers. Accordingly, the near-infrared spectroscope has been applied to measure oxygen levels in the physiological medium such as tissue hemoglobin oxygen saturation and total hemoglobin concentrations.

Various techniques have been developed for the near-infrared spectroscopy, e.g., time-resolved spectroscopy (TRS), phase modulation spectroscopy (PMS), spatial frequency domain imaging (SFDI), and continuous wave spectroscopy (CWS). In a homogeneous and semi-infinite model, both TRS and PMS have been used to obtain spectra of an absorption coefficient and reduced scattering coefficient of the physiological medium by solving a photon diffusion equation, and to calculate concentrations of oxygenated and deoxygenated hemoglobin as well as tissue oxygen saturation. CWS has generally been designed to solve a modified Beer-Lambert equation and to measure changes in the concentrations of oxygenated and deoxygenated hemoglobin.

Despite their capability of providing the hemoglobin concentrations as well as the oxygen saturation, one major drawback of TRS and PMS is that the equipment is bulky and expensive. CWS may be manufactured at a lower cost but is limited in its utility because it cannot compute the oxygen saturation from the changes in the concentrations of oxygenated and deoxygenated hemoglobin.

Optical diffusion imaging and spectroscopy (ODIS) allows tissue to be characterized based on measurements of photon scattering and absorption. In tissue such as human tissue, near-infrared light is highly scattered and minimally absorbed. Optical diffusion imaging is achieved by sending optical signals into tissue and measuring the corresponding diffuse reflectance or transmittance on the tissue surface.

Scattering is caused by the heterogeneous structure of a tissue and, therefore, is an indicator of the density of a cell and the nuclear size of the cell. Absorption is caused by interaction with chromophores. ODIS emits light into tissue through a sensor. The position of the light source which emits the light and a detector which detects the light allows a depth of measurement to be determined. A ratio of oxyhemoglobin and deoxyhemoglobin may be used to allow for substantially real-time measurement of oxygen, e.g., oxygen saturation levels. In some embodiments, a light source emits electromagnetic waves that include a carrier wave. In some of these embodiments, an electromagnetic wave described herein may further include a modulating signal (or message signal) where the modulating signal carries the information that is superimposed onto the carrier wave to allow the information to be transmitted via the electromagnetic waves. In some embodiments where more than one light source is employed, the emitted light from these multiple sources include multiple different wavelengths (or frequencies) of light where each light source may emit light having a single wavelength or multiple different wavelengths (e.g., multispectral light source). In these embodiments, the respective carrier waves of light having different wavelengths (or frequencies) are characteristically different from one another as respectively exhibiting at least different wavelengths and different frequencies.

Within ODIS systems, sensors which come into contact with tissue surfaces generally have optical fibers arranged thereon in a substantially symmetric layout. That is, optical fibers that are coupled to light sources are arranged in a substantially symmetric orientation relative to optical fibers that are coupled to light detectors. While a symmetric orientation is effective in allowing for oxygen saturation levels to be measured, the manufacture of such sensor is often difficult, as the exact placement of the optical fibers within the sensor is crucial. Further, when the anatomy of tissue or underlying structure is not substantially symmetric, the use of a sensor with a symmetric orientation may not allow for accurate measurements to be readily made.

Therefore, what is needed in some embodiments is a sensor that is relatively easy to manufacture, and is arranged to be used on tissue which may not have a symmetric anatomy. That is, what is desired is a sensor with a layout of optical structures (which can include optical fibers) for light sources and optical structures (which can include optical fibers) for detectors that facilitate use with tissue having substantially any anatomy.

Some embodiments of the present invention relate to medical devices and their manufacture. More particularly, the present invention relates to patient monitoring devices and methods.

Patient monitoring systems measure, display, and sometimes store physiological data. Patient monitoring systems are now used in a wide variety of applications. This includes, for example, hospital, ambulatory, and home health care. Hospitals routinely measure and analyze the vital signs of surgical, trauma, and other patients from admission through discharge. There are many different types of monitoring devices. For example, there are monitoring devices for blood pressure, body temperature, heart activity, blood gases, cholesterol, glucose, pulse rate, respiration rate, tissue oxygen saturation, and many other parameters.

Noninvasive monitoring devices fulfill an important role in assessing, tracking, diagnosing, and treating patients. These devices enable early diagnosis, treatment of acute conditions, and reduce the need for invasive interventions. Some types of monitoring devices gather patient data via sensors attached to the patient.

In order for the sensors gather accurate information, it is important that they are protected from outside interference. They should also be comfortable for the patient to wear as the sensors may be attached to the patient for long periods of time. Furthermore, in an operating room environment or for an open wound, anything that touches or comes near the patient must be sterile. Thus, sterility is also a concern. These are just a few examples of desirable features.

There is, then, a continuing demand for medical devices that are easier to use, safer to use, usable in locations outside the hospital, provide more features, and generally address the needs of patients, doctors, nurses, clinicians, first responders, and others in the medical community.

Some embodiments of the present invention fulfill the need to provide improved systems and techniques for monitoring patients.

Some embodiments of the present invention relate to methods of diagnosing peripheral vascular disease (PVD) using measured changes in oxygen saturation in tissue. More specifically, the invention relates to diagnosing peripheral vascular disease from an analysis of oxygen saturation during recovery from ischemia (reduced or stoppage of blood flow).

These embodiments thus provide innovative techniques for diagnosing peripheral vascular disease as well as techniques of diagnosing peripheral vascular disease with relatively high accuracy rates.

Some embodiments of the present invention relate to methods and apparatuses of diagnosing peripheral vascular disease (PVD) using measured changes in oxygen saturation in tissue. More specifically, these embodiments relate to diagnosing peripheral vascular disease from an analysis of oxygen saturation during recovery from ischemia (reduced or stoppage of blood flow).

There is a need for innovative techniques for diagnosing peripheral vascular disease in these embodiments. Additionally or alternatively, there is a need for techniques of diagnosing peripheral vascular disease with relatively high accuracy rates.

Some embodiments relate generally to optical imaging systems that monitor oxygen levels in tissue. More specifically, the present invention relates to monitoring oxygen levels to determine the viability of flaps before and after a flap transplant.

Some embodiments of the present invention relate to medical devices and their manufacture. More particularly, the present invention relates to patient monitoring devices and methods.

Patient monitoring systems measure, display, and sometimes store physiological data. Patient monitoring systems are now used in a wide variety of applications. This includes, for example, hospital, ambulatory, and home health care. Hospitals routinely measure and analyze the vital signs of surgical, trauma, and other patients from admission through discharge. There are many different types of monitoring devices. For example, there are monitoring devices for blood pressure, body temperature, heart activity, blood gases, cholesterol, glucose, pulse rate, respiration rate, tissue oxygen saturation, and many other parameters.

Noninvasive monitoring devices fulfill an important role in assessing, tracking, diagnosing, and treating patients. These devices enable early diagnosis, treatment of acute conditions, and reduce the need for invasive interventions. Some types of monitoring devices gather patient data via sensors attached to the patient.

In order for the sensors gather accurate information, it is important that they are protected from outside interference. They should also be comfortable for the patient to wear as the sensors may be attached to the patient for long periods of time. Furthermore, anything that touches or comes near the patient must be sterile. Thus, sterility is also a concern. These are just a few examples of desirable features.

There is, then, a continuing demand for medical devices that are easier to use, safer to use, usable in locations outside the hospital, provide more features, and generally address the needs of patients, doctors, nurses, clinicians, first responders, and others in the medical community.

Therefore, there is a need for an improved system and techniques for monitoring patients.

Some embodiments of the present invention relate to the field of medical devices, their use and manufacture, and more specifically to medical devices and techniques for diagnosing intestinal ischemia or bowel ischemia.

When blood supply to a tissue or organ within a body is diminished due to a poor circulation or blockage of blood vessels, the tissue or organ suffers ischemia which results in diminished functioning of the tissue or organ. The tissue or organ ischemia can present various symptoms in a patient which makes a proper diagnosis of the underlying disease difficult for a doctor. Consequently, an ischemic disease is often not diagnosed until an advanced stage, which limits treatment options for the patient.

This is particularly the case for a patient suffering with intestinal ischemia. The ischemic condition or oxygenation state of an internal organ, such as the intestine or mesentery, is difficult to evaluate. The intestine is a long tubular organ which can stretch about 7 feet long. The mesentery is a fold of tissue which anchors the intestine to the back of the abdominal wall. Blood vessels, nerves, and lymphatics branch through the mesentery to supply the intestine. Since the intestine and mesentery involve an extensive network of tissues, it is difficult to localize an ischemic area in the tissue.

The present invention provides various medical devices and systems for measuring oxygen saturation of a tissue located inside a body. In particular, the devices and systems can be used to measure oxygen saturation of mouth, esophagus, stomach, small intestine, large intestine, mesentery, anus, or others. While some of these body parts may be classified as organs, for this application, "tissue" and "organ" are used interchangeably to refer to any body part or aggregate of cells. In other words, "tissue" may be used to refer to an organ, and vice versa.

The medical devices and systems in accordance with embodiments of the invention include a catheter device, an endoscopic device, and a needle sensor device which allow the doctor to explore tissues deep inside a body noninvasively or with a minimal pin size puncture. In embodiments of the invention, the devices include a sensor probe that has one or more optical fibers that form an oximeter at a distal end of the sensor probe. As the devices are guided down along the gastrointestinal tract, the oximeter sensor of the sensor probe can contact a tissue and measure oxygen saturation at various locations along the tract.

In embodiments of the invention, the sensor probe is connected to a signal emitter which sends light having a wavelength between about 600 nanometers to about 1000 nanometers through optical fibers in the sensor probe into a tissue in some embodiments. In some embodiments, the wavelength may fall within the range of about 700 nanometers to about 900 nanometers. After being scattering and absorbed by chromophores (e.g., hemoglobin) in the tissue, an attenuated version of the light is detected by the sensor probe and is transmitted to a photodetector.

In an implementation, the sensor probe uses a ratiometric algorithm, and does not use a calibration or have any knowledge of an unattenuated brightness. In another implementation, based on values of the initial light and the attenuated version of the light, an oxygen saturation value of the tissue can be obtained. Based on the oxygen saturation value of the tissue, it can be determined whether the tissue is suffering from ischemia.

Embodiments of the invention can be used in a wide variety of applications. One application is in diagnosing whether or not a patient has intestinal ischemia or exhibits a hypoxia condition. Moreover, the devices and systems can be used to determine the severity of intestinal ischemia and the extent of tissue damage. In another application, the devices and systems can be used in monitoring oxygen saturation of an intestinal tissue or mesentery during a surgical procedure (e.g., anastomosis). Since oxygen saturation measurements can be made in real-time during surgery, any necessary modifications to surgical procedures can be made based on oxygen saturation measurements. Furthermore, the devices and systems can also be used during recovery after surgery to evaluate a patient's prognosis.

Embodiments of the present invention provide several advantages. The catheter and endoscopic devices can be inserted into a human body noninvasively to determine the oxygenation state of a mucosal surface of the intestine or any other tissue along the gastrointestinal tract. Moreover, the sensor needle device can be introduced into an abdomen with a pin-size hole to determine the oxygenation state of a serosal surface of the intestine or mesentery. These devices cause minimal discomfort to the patient and rarely cause any medical complications.

Moreover, the devices and systems according to embodiments of the invention provide oxygen saturation measurements of the entire thickness of the intestine, not just an outer skin or superficial surface of the intestine. An oximeter sensor of the present devices and systems also directly contact a tissue to make oxygen saturation measurements of the tissue. Thus, the oxygen saturation measurements according to embodiments of the invention can assess the oxygenation state of the intestine more accurately.

Further, sensor probes, catheter devices, and sensor needle devices of the present invention are cost effective to manufacture. The cost effectiveness is important as the devices containing a sensor probe are typically disposed after a single use. Also, since the portion of a device that is placed onto tissue or introduced into a body cavity is sealed (e.g., electrically sealed and liquid or fluid sealed) so that any electrical components such as light emitting diodes, photodiodes, or exposed electrical connections, cannot come in contact with tissue or internal organs, which may otherwise be subject to electrical shock, heating, or burning by the device.

Moreover, assessing the blood supply associated with a flap is crucial to ensure that the flap is viable. By monitoring the oxygen saturation level of an area on flap tissue, the blood flow to at least that area may be determined. Monitoring an oxygen saturation level is generally a non-invasive, non-subject process. Near-infrared spectroscopy has been used for non-invasive measurement of various physiological properties in animal and human subjects. The basic principle underlying the near-infrared spectroscopy is that physiological tissues include various highly-scattering chromophores to the near-infrared waves with relatively low absorption. Many substances in a medium may interact or interfere with the near-infrared light waves propagating therethrough. Human tissues, for example, include numerous chromophores such as oxygenated hemoglobin, deoxygenated hemoglobin, water, lipid, and cytochrome, where the hemoglobin are the dominant chromophores in the spectrum range of approximately 700 nanometers to approximately 900 nanometers. Accordingly, the near-infrared spectroscope has been applied to measure oxygen levels in the physiological medium such as tissue hemoglobin oxygen saturation and total hemoglobin concentrations.

Optical Diffusion Imaging and Spectroscopy (ODIS) allows tissue to be characterized based on measurements of photon scattering and absorption. In tissue such as human tissue, near infrared light is highly scattered and minimally absorbed. Optical diffusion imaging is achieved by sending optical signals into tissue and measuring the corresponding diffuse reflectance or transmittance on the tissue surface.

Scattering is caused by the heterogeneous structure of a tissue and, therefore, is an indicator of the density of a cell and the nuclear size of the cell. Absorption is caused by interaction with chromophores. ODIS emits light into tissue through a sensor. The position of the light source which emits the light and a detector which detects the light allows a depth of measurement to be determined. A ratio of oxy-hemoglobin and deoxyhemoglobin may be used to allow for substantially real-time measurement of oxygen, e.g., oxygen saturation levels. A percentage of hemoglobin that is bound to oxygen may express an oxygen saturation level.

In one embodiment, measuring oxygen saturation levels associated with a flap may enable a surgeon to accurately identify areas of a flap that may not be viable. Being able to identify areas that are not viable enables corrective actions to be taken substantially before the integrity of the overall flap is compromised. By way of example, a surgeon may be able to trim tissue from areas of a flap that may not be viable in an effort to preserve the integrity of the remainder of the flap. In addition, if oxygen saturation levels are measured in a potential flap before the potential flap is removed for transplant, arteries that provide significant blood flow to the potential flap may be identified and, hence, designated for use as reattachment arteries.

Some embodiments are directed to a sensor head which is such that optical fibers that are coupled to light sources are arranged in an offset orientation relative to optical fibers that are coupled to detectors allows the sensor head to be utilized in areas in which tissue being monitored and is not substantially symmetric. Any attenuation associated with the offset orientation of optical fibers that are coupled to light sources is typically compensated for through software. Such a sensor head is relatively easy to manufacture in that the placement of optical fibers that are coupled to light sources is less rigid, e.g., any slight variation in the placement of the optical fibers may be corrected for using the software that compensates for attenuation. In addition, the use of software to compensate for attenuation associated with the placement of optical fibers on a sensor head essentially enables the sensor head to be used with both symmetric and asymmetric tissue anatomies.

As will be understood by those skilled in the art, a volume of tissue substantially immediately beneath a sensor head may either be homogeneous or inhomogeneous depending upon the actual anatomical structures contained within this volume. By way of example, when a sensor head is positioned on skin overlying a thick region of adipose tissue, the distribution of, for example, epithelial cells, capillaries, and tissues containing red blood cells that contain oxygenated hemoglobin is generally relatively uniform, e.g., symmetric and homogenous. However, a sensor head may be positioned over a tissue volume in which underlying structure include arteries, veins, bone, tendon, cartilage, fascia, muscle, or pigmented lesions. Such tissue may have asymmetric anatomies that cause light to be reflected, refracted, or absorbed asymmetrically due, for example, to regions that are either unusually reflective or absorptive. It shall be noted that refraction does occur when shining light on a physiological medium, oximetry primarily relies on reflection of light where differential light absorption by oxygenated and deoxygenated hemoglobin at specific wavelengths for measuring how much light is absorbed by the blood at different light colors to determine, for example, oxygen saturation levels.

Software can compensate for attenuation may eliminate readings associated with light that reflects off of structures such as bone. Optical structures that are coupled to sources and are positioned in a sensor head in an offset orientation relative to optical structures optically coupled to detectors may facilitate the transmission and reading of light that avoids structures such as bone. Hence, the use of offset source optical structure orientations facilitates the creation of specialized sensor heads that may be used to measure oxygen saturation in many different parts of a body. In some embodiments, reflection occurs when light bounces off a surface (e.g., a surface on the exterior or interior of a physiological medium such as human tissues), while refraction occurs when light bends as the light passes through a medium (e.g., a physiological medium). Either reflection or refraction or both reflection and refraction when shining a light onto a physiological medium. For example, a portion of the light may penetrate into the physiological medium and changes direction or propagation (refraction); a smaller portion of the penetrated light may be absorbed; and some or all of the remainder of the penetrated light may be reflected off one or more surfaces within the physiological medium and eventually leave the physiological medium and detected by, for example, a detector described herein.

Some embodiments are directed to assessing the blood supply associated with a flap is crucial to ensure that the flap is viable. By monitoring the oxygen saturation level of an area on flap tissue, the blood flow to at least that area may be determined. Monitoring an oxygen saturation level is generally a non-invasive, non-subject process. Near-infrared spectroscopy has been used for non-invasive measurement of various physiological properties in animal and human subjects. The basic principle underlying the near-infrared spectroscopy is that physiological tissues include various highly-scattering chromophores to the near-infrared waves with relatively low absorption. Many substances in a medium may interact or interfere with the near-infrared light waves propagating therethrough. Human tissues, for example, include numerous chromophores such as oxygenated hemoglobin, deoxygenated hemoglobin, water, lipid, and cytochrome, where the hemoglobin are the dominant chromophores in the spectrum range of approximately 700 nanometers to approximately 900 nanometers. Accordingly, the near-infrared spectroscope has been applied to measure oxygen levels (e.g., tissue hemoglobin oxygen saturation and total hemoglobin concentrations) in a physiological medium.

Optical Diffusion Imaging and Spectroscopy (ODIS) allows tissue to be characterized based on measurements of photon scattering and absorption. In tissue such as human tissue, near infrared light is highly scattered and minimally absorbed. Optical diffusion imaging is achieved by sending optical signals into tissue and measuring the corresponding diffuse reflectance or transmittance on the tissue surface.

Scattering is caused by the heterogeneous structure of a tissue and, therefore, is an indicator of the density of a cell and the nuclear size of the cell. Absorption is caused by interaction with chromophores. ODIS emits light into tissue through a sensor. The position of the light source which emits the light and a detector which detects the light allows a depth of measurement to be determined. A ratio of oxy-hemoglobin and deoxyhemoglobin may be used to allow for substantially real-time measurement of oxygen, e.g., oxygen saturation levels. A percentage of hemoglobin that is bound to oxygen may express an oxygen saturation level.

In the description that follows, the present invention will be described in reference to embodiments. However, embodiments of the invention are not limited to any particular environment, application, or implementation. For example, although different techniques of monitoring changes in oxygen saturation will be described, the invention is not limited to the specific embodiments described below. Therefore, the description of the embodiments that follows is for purposes of illustration and not limitation. Further, any embodiment or even a feature thereof described herein can be readily combined with any other embodiment or embodiments or feature thereof described herein or equivalents thereof, unless otherwise explicitly disclaimed or described as mutually exclusive of one another. Moreover, examples of embodiments of the invention are shown using figures and are described below. The figures described herein are used to illustrate embodiments of the invention, and are not in any way intended to be restrictive of the broad invention. Embodiments of the invention are not limited to the specific arrangements and constructions shown and described. For example, features shown in one figure can be combined with features shown in another figure.

FIG. 1 is an architectural diagram of a computing environment to which various techniques described herein may be applied in some embodiments. More specifically, FIG. 1 shows a computing environment 100 where a plurality of client systems 108 (e.g., one or more computing devices such as a tablet, a laptop, a desktop, a server, and others in a medical care facility) may be connected with one or more medical device systems 102 (e.g., a medical device system or a patient monitoring system for monitoring viability of a biological tissue, via a cloud computing environment or a network 104 (e.g., a private cloud, a public cloud, a hybrid cloud, the Internet, an intranet, a mesh network, and others) to provide various features, functions, tasks, and others.

The cloud computing environment or network 104 (e.g., a public cloud, a private cloud, a hybrid cloud, and others) may be provisioned for by one or more server systems 106 (e.g., one or more server computers, one or more virtual machines, one or more executable containers, and others) in some embodiments. A medical device system may be connected either through a cable, wirelessly, or through a combination of both wired and wireless transmission to one or more probes 110 (e.g., a sensor probe unit described herein) to facilitate various functionalities described herein (e.g., monitoring viability of a biological tissue, intestinal ischemia, bowel ischemia, peripheral vascular disease, and others, measurement of changes in the concentrations of oxygenated hemoglobin, deoxygenated hemoglobin, and others.

Figure 2:
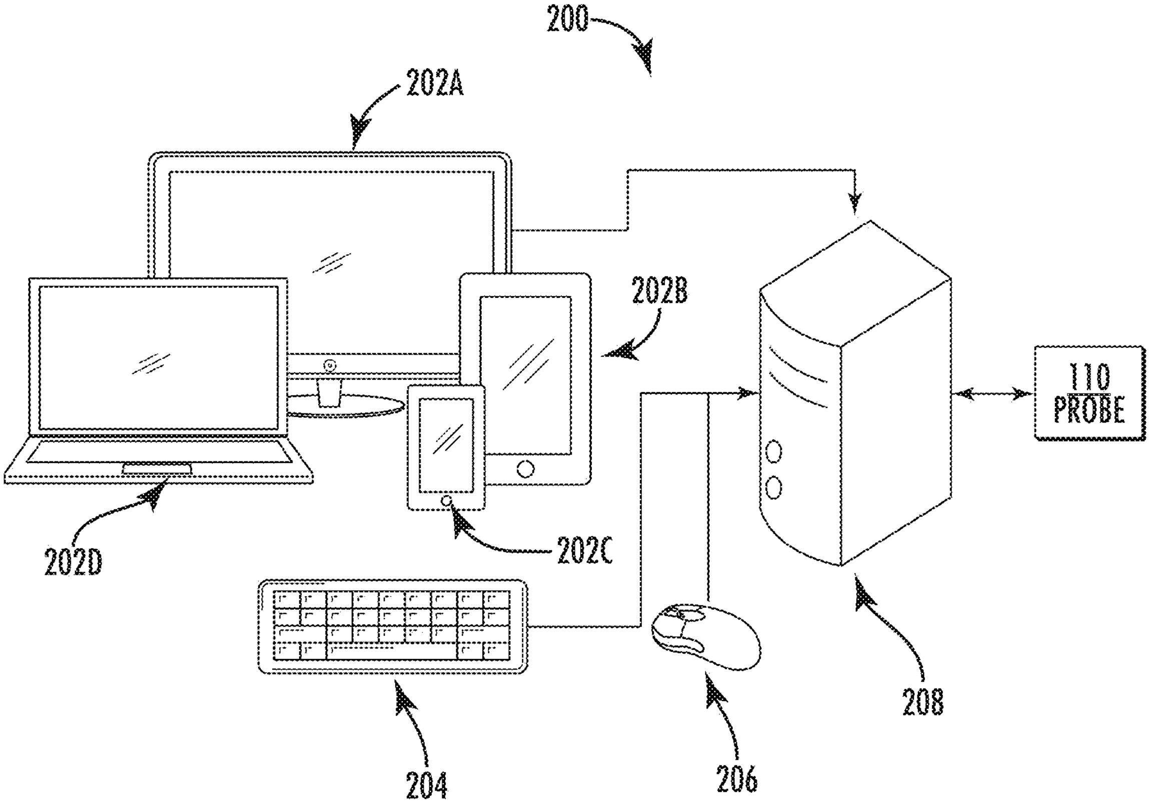
FIG. 2 shows a simplified computing device in which some of various techniques described herein may be implemented, according to some embodiments.

FIG. 2 is a simplified schematic diagram of a computing system 200 in which some of various techniques described herein may be implemented, according to some embodiments. For example, the example computing system 200 (e.g., a medical device system or patient monitoring system 102 in FIG. 1) may be implemented in a manner to allow for provisioning various techniques, functionalities, features, and others described herein. A computer system 200 (e.g., a tablet 202B, a smartphone 202C, a laptop 202D, a desktop, a terminal or computing device connected a server, and others) is connected to one or more probes 110 (e.g., one or more sensor probe units described herein). A probe 110 may be placed in close contact to a biological tissue (not shown) in order to collect data that may be further analyzed by the computer system 200 in order to determine viability (e.g., oxygen saturation) in the biological tissue. Oxygen saturation calculations may be made by components of the probe or by the computing system, or partial calculations may be made by components of the probe while further or remaining calculations are made by the computing system.

In some embodiments, the system for measuring oxygen saturation in tissue is as described in U.S. patent application Ser. No. 09/877,515, filed Jun. 7, 2001, which issued as U.S. Pat. No. 6,587,703 on Jul. 1, 2003, which is incorporated by reference. For example, the oxygen saturation system can use continuous wave spectroscopy (CWS) to determine absolute values of concentrations of oxygenated and deoxygenated hemoglobin in a patient's tissue. In other embodiments, other systems for measuring oxygen saturation in tissue can be utilized.

The computing system 200 may include, for example, a computing device 208 including, for example, one or more central processing units (CPUs), memory, storage devices, and others, a display 202A, a physical or virtual pointing device 206 (e.g., a physical or virtual touchpad, mouse, stylus, pen, and others), a physical or virtual keyboard 204, or any other required or desired components, and others to facilitate provisioning various techniques, functionalities, features and others described herein. In some embodiments, the computing system 200 my include a tablet computing device 202B or a smart phone 202C that includes the aforementioned one or more central processing units, memory, storage device(s), and a display. In some embodiments, the tablet computing device 202B or the smartphone 202C may be wirelessly connected to a keyboard (204) and/or a pointing device (e.g., 206). In some other embodiments, the functions of a pointing device (e.g., 206A) may be replaced by the touch screen of the tablet computing device 202B or the smartphone 202C, and the functions of a keyboard (e.g., 204) may be replaced by an on-screen virtual keyboard in some other embodiments. In some embodiments the computing device 200 may be a laptop computer that has a built-in display, a built-in pointing device, and a built-in physical keyboard, in addition to one or more central processing units, memory, and storage device(s).

Figure 3:
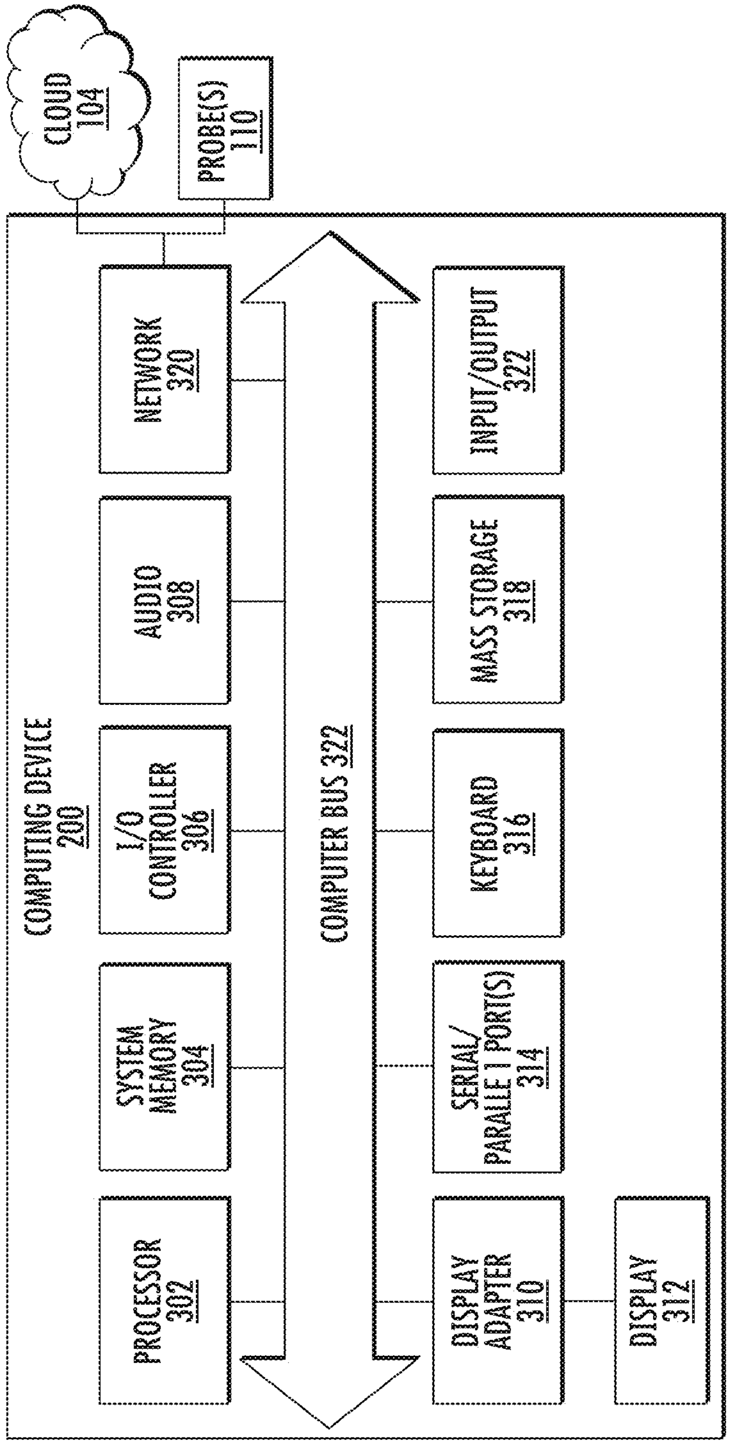
FIG. 3 shows a simplified schematic diagram of the example computing device of FIG. 2 in which some of various techniques described herein may be implemented, according to some embodiments.

FIG. 3 shows an example, simplified schematic diagram of the example computing device of FIG. 2 in which some of various techniques described herein may be implemented, according to some embodiments. A computer device (e.g., a computing system 200 in FIG. 2) includes a processor 302 that executes instructions from computer programs (including operating systems). Although processors typically have memory caches (e.g., L1, L2, and/or L3 cache) also, processor 302 utilizes memory 304, which may store instructions or computer code and data.

A mass storage (e.g., hard disks, solid state drives, and others) 318 stores computer programs and data such that it is typically persistent and provides more storage when compared to memory 304. A mass storage 318 may also include a removable storage device that provides mobility to computer programs and/or data that is stored thereon. Examples of removable storage devices include floppy disks, tape, CD-ROM, flash memory devices (and other nonvolatile storage), and the like.

Memory 304, mass storage 318, and removable storage provide examples of non-transitory computer readable storage media that may be utilized to store and retrieve computer programs incorporating computer codes that implement the invention, data for use with the invention, and the like. Additionally or alternatively, a data signal embodied in a carrier wave (e.g., in a network including the Internet) may be another form of a computer readable storage medium. An input 322 allows a user to interface with the system via an input/output (I/O) controller 306. Inputs may be provided through the use of a keyboard 316, a mouse, buttons, dials, or any other input mechanism. An output 322 allows the system to provide output to the user. Output may be provided through a monitor, display screen, LEDs (light omitting diodes), printer, or any other output mechanism.

The computing device 200 may include one or more display adapters 310 that function in conjunction with a display 312 to, for example, provide a user interface (not shown) that accepts inputs 322 and displays outputs 322. The computing device may include a charting subsystem(s), mechanism(s), or module(s) that provides charting capabilities of various measurements (e.g., charting oxygenated hemoglobin and representing as oxygen saturation or StO2) and display the charting results in a user interface. For example, the percentage of hemoglobin molecules bound to oxygen may be plotted on the y-axis against the partial pressure of oxygen on the x-axis to create a sigmoid-shaped curve such as an oxygen dissociation curve that demonstrates how readily oxygen binds to hemoglobin at different oxygen levels in some embodiments (e.g., a higher saturation percentage indicates more oxygenated hemoglobin is present in the blood). A computing device 200 may include one or more ports 314 in some embodiments. For example, a computing device 200 may include a serial port that includes a serial communication interface through which information transfers in or out sequentially one bit at a time and/or a parallel port that includes an interface allowing the computing device 200 to transmit or receive data down multiple bundled cables to a peripheral device (e.g., a printer).

A network or network interface 320 allows the system to interface with a network to which it is connected. For example, the network or network interface 320 may connect the computing device 200 to a cloud computing environment or network (e.g., 104 in FIG. 1) and/or one or more probes 110 (e.g., a sensor probe unit described herein) in some embodiments. The one or more respective connections between the network or network interface 320 and the one or more probes 110 may be wireless connections in some embodiments, wired connections in other embodiments, or a combination of wired connection(s) and wireless connection(s) in yet some other embodiments. The system bus or computer bus architecture of the computing device 200 is represented by arrows 322. The example components shown in FIG. 3 may be found in many computer systems. However, components can be added, deleted, and combined. Thus, FIG. 3 is for illustration purposes, without limitation.

Figure 4:
FIG. 4 shows an example of a mobile computing device in which some of various techniques described herein may be implemented, according to some embodiments.

FIG. 4 shows an example mobile computing device such as a smart phone device in which some of various techniques described herein may be implemented, according to some embodiments. More specifically, FIG. 4 shows an example mobile computing device that may be used as a client computing device 401 (e.g., client system 108 in FIG. 1) that may include, for example without limitation, a display 403, a front-facing camera 409, a rear-facing camera (not shown), a speaker or an array of multiple speakers 411, an optional proximity sensor 409, a multi-function virtual or physical button 410 (e.g., for accessing one or more menus or home screen, for obtaining fingerprints for authentication and/or authorization, and others).

Figure 5:
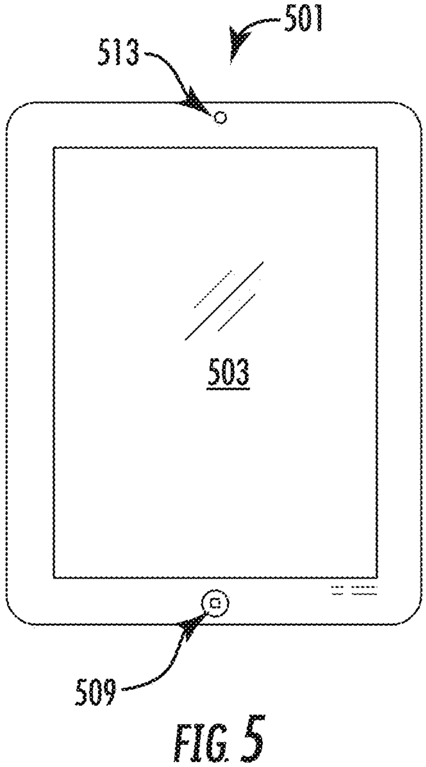
FIG. 5 shows another example of a mobile computing device in which some of various techniques described herein may be implemented, according to some embodiments.

FIG. 5 shows another example mobile computing device such as a tablet computing device in which some of various techniques described herein may be implemented, according to some embodiments. More specifically, FIG. 5 shows an example tablet computing device that may be used as a client computing device 501 (e.g., client system 108 in FIG. 1) that may include, for example without limitation, a display 503, a front-facing camera 513, a rear-facing camera (not shown), a speaker or an array of multiple speakers (not shown), a multi-function virtual or physical button 509 (e.g., for accessing one or more menus or home screen, for obtaining fingerprints for authentication or authorization, and others).

Figure 6:
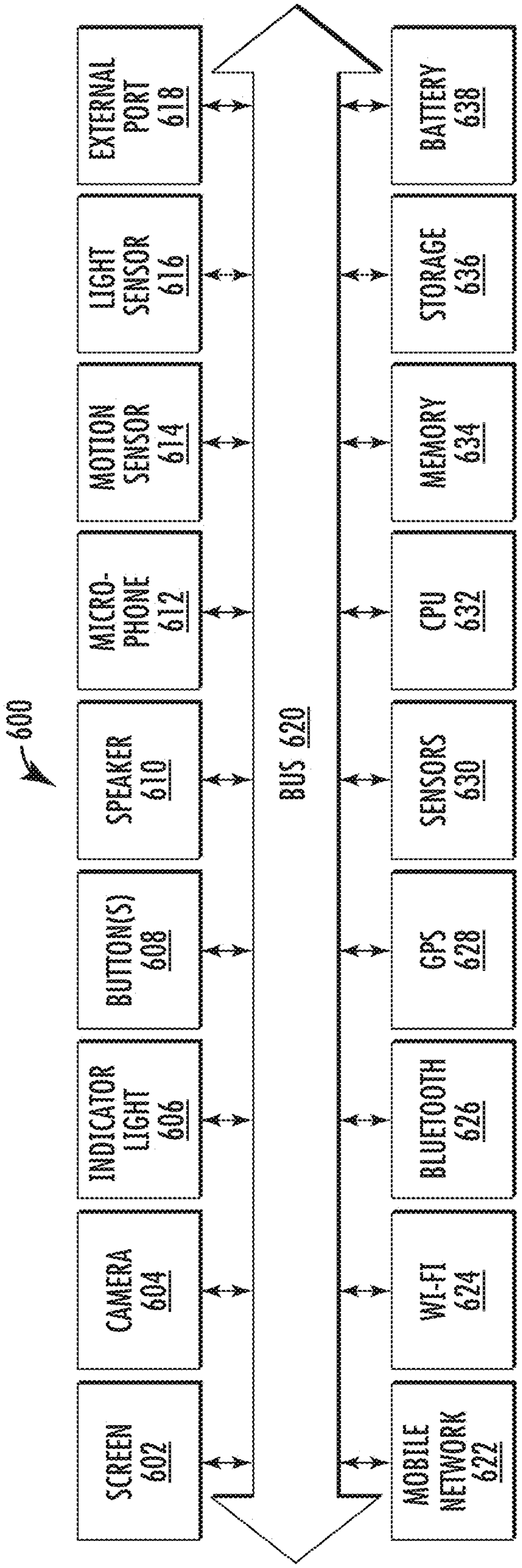
FIG. 6 shows a simplified schematic diagram of an example computing device in which some of various techniques described herein may be implemented, according to some embodiments.

FIG. 6 shows a simplified schematic diagram of an example computing device in which some of various techniques described herein may be implemented, according to some embodiments. More particularly, FIG. 6 shows a simplified schematic diagram of an example mobile computing device (e.g., the smart phone device 401 in FIG. 4 or the tablet computing device 501 in FIG. 5).

FIG. 6 shows an example, simplified schematic diagram of the example mobile computing device of FIG. 4 or 5 in which some or all of various techniques described herein may be implemented, according to some embodiments. The example components shown in FIG. 6 may be found in many mobile computing devices. However, components may be added, deleted, and combined. Thus, FIG. 6 is for illustration purposes, without limitation. A mobile computing device 600 (e.g., a smart phone 401 in FIG. 4 or a tablet computing device 501 in FIG. 5) includes a bus 620 that includes a communication system that transfers data between components inside a computer (e.g., the computing device 600), or between computers (e.g., between the computing device 600 and one or more other computing devices). The system bus or computer bus architecture 620 of an example mobile computing device 600 is represented by arrows.

These components inside the example mobile computing device 600 connected via the bus architecture 620 may include, for example without limitation, a processor 632 (e.g., a central processing unit or CPU) that executes instructions from computer programs (including operating systems). Although processors typically have memory caches (e.g., L1, L2, or L3 cache, or any combination) also, processor 632 utilizes memory 634 (e.g., dynamic random-access memory or DRAM), which may store instructions or computer code and data.

A storage device (e.g., persistent memory, a solid-state high-performance byte-addressable memory device, solid state drives, and others) 636 stores computer programs and data such that it is typically persistent and provides more storage when compared to memory 634. A mass storage 318 may also include a removable storage device that provides mobility to computer programs and/or data that is stored thereon. A persistent memory or PRAM is a type of computer memory with the speed of RAM (random access memory), the retention of an SSD (solid stated drive), and which remembers data even after powering off the device.

Memory 632 and storage device 636 provide examples of non-transitory computer readable storage media that may be utilized to store and retrieve computer programs incorporating computer codes that implement the invention, data for use with the invention, and the like. Additionally or alternatively, a data signal embodied in a carrier wave (e.g., in a network including the Internet) may be another form of a computer readable storage medium. These various components of components of a mobile computing device 600 may be powered by a battery 638 that may be charged via a charging circuit (not shown).

The mobile computing device 600 may include one or more display adapters (not shown) that function in conjunction with a display 602 to, for example, provide a user interface (not shown) that accepts inputs and displays outputs. A mobile computing device 600 may include one or more ports 618 in some embodiments. For example, a mobile computing device 600 may include a serial port that includes a serial communication interface through which information transfers in or out sequentially one bit at a time and/or a parallel port that includes an interface allowing the mobile computing device 600 to transmit or receive data down multiple bundled cables to a peripheral device (e.g., a printer).

Additional or alternatively, these components inside the example mobile computing device 600 connected via the bus architecture 620 may include, for example without limitation, a screen 602, one or more cameras 604 (e.g., a front-facing camera, a rear-facing camera, and others), one or more indicator light 606, one or more physical or virtual buttons, or a combination, or switches 608, a speaker or an array of multiple speakers 610, one or more microphones 612 (e.g., an array of a plurality of microphones for beamforming, actively cancelling noises, controlling directional audio outputs, and others), one or more sensors 614 (e.g., proximity sensor, motion sensor, and others), one or more light sensors, photosensors, or photodiodes 616 to sense and collect one or more characteristics of light (e.g., color information, respective luminous intensity of a color component such as red, green, or blue of incident light, illuminance in the unit of lux such as the luminous flux as perceived by a surface, and others) and/or to convert perceived light to electricity in some embodiments.

These components inside the example mobile computing device 600 connected via the bus architecture 620 may additionally or alternatively include, for example without limitation, one or more external ports 618 (e.g., a lightning port, a Thunderbolt port, a USB-C port, and others) for interfacing with external devices as well as a plurality of networking or telecommunication modules such as respective modules for a mobile or cellular network 622, a Wi-Fi network 624, or a Bluetooth connection 626, and others.

Figure 7A:
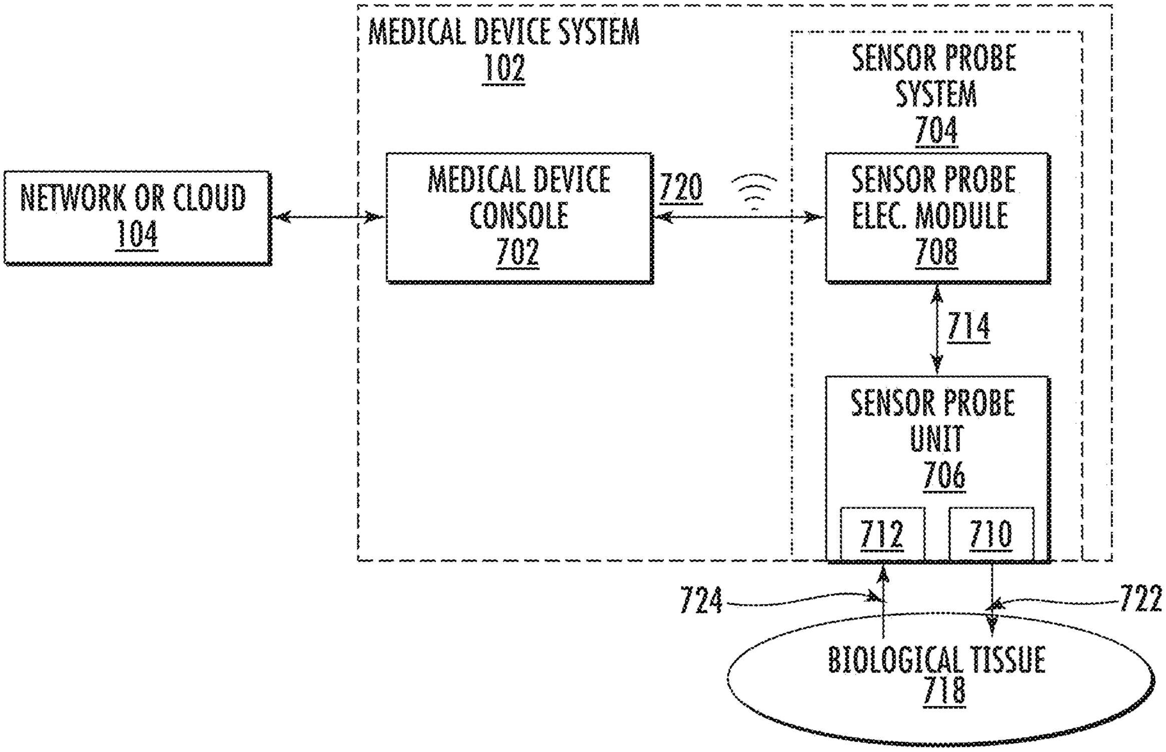
FIG. 7A shows a simplified schematic diagram of an example medical device system in which some of various techniques described herein may be implemented, according to some embodiments.

FIG. 7A shows a simplified schematic diagram of an example medical device system in which some of various techniques described herein may be implemented, according to some embodiments. More specifically, FIG. 7A shows a simplified schematic diagram of an example medical device system (e.g., medical device system 102 in FIG. 1). In these embodiments, a medical device may be connected to one or more other computing devices (e.g., another medical device system 102, a tablet computing device, a smartphone, a laptop computer, a desktop, a terminal connected to a server computer, and others) via the network or cloud 104 shown in FIG. 1.

In these embodiments, the medical device system 102 may include a medical device console 702 and a sensor probe system 704 that is connected to the medical device console 702 via a wired or wireless connection 720. In some embodiments, the connection 720 may be established with a standard protocol such as Bluetooth or other local wireless network (IoT protocols such as Zigbee wireless mesh network, Z-wave, Bluetooth Low Energy (BLE or Bluetooth LE) aka Bluetooth 4.1. More details about the medical device console 702 will be described below. Other IoT protocols that may also be used for the connection 720 include, for example, Advanced Message Queuing Protocol, AMQP, Cellular-2G, 3G, 4G/LTE, 5G, and others, Constrained Application Protocol or CoAP, Data Distribution Service or DDS, LoRa, LoRaWAN, Lightweight M2M (LWM2M) as a device management protocol designed for sensor networks and the demands of an M2M environment, Message Queuing Telemetry Transport or MQTT, Wi-Fi, XMPP Extensible Messaging and Presence Protocol for real-time human-to-human communication, Zigbee which has a longer range than BLE but a lower data rate than BLE, Z-Wave allowing smart devices to communicate with encryption and thereby providing a level of security to the IoT (Internet of Things) deployment, and others Bluetooth LE, colloquially BLE, formerly marketed as Bluetooth Smart) is a wireless personal area network technology. Bluetooth mesh profiles use Bluetooth Low Energy to communicate with other Bluetooth Low Energy devices in the network. Each device may pass the information forward to other Bluetooth Low Energy devices creating a mesh effect. The built-in encryption in, for example, BLE, Z-Wave, and others provide a first level of encryption to satisfy the FDA encryption requirements of encrypting patient monitoring data collected from medical devices with cryptographic protocols (e.g., AES (Advanced Encryption Standard)-256 implemented with the Wi-Fi Protected Access or WPA or WPA2 protocol). Some embodiments provide multiple levels of encryption to protect the confidentiality and security of the raw data collected from users as well as other derivative data (e.g., a functional oxygen saturation SO2 measuring the percentage of hemoglobin in red blood cells, a specific oxygen saturation StO2 (from tissue oximetry), a specific oxygen saturation SpO2 (from pulse oximetry), and others) that is derived from the raw data by, for example, using one or more cryptographic protocols for the transmission as well as storage of the aforementioned data.

In some embodiments, the medical device console 702 includes a computing device such as a tablet computer, a laptop, a smartphone, a desktop computer, or any other equivalent computing devices that have the capability of computing, charting, display of raw or derived data, networking and communication, and/or storage. In some of these embodiments, the medical device console 702 may be customized with at least one or more software applications that perform various computations, charting, data processing and management, and others described herein on the medical device console 702. In other embodiments, the medical device console 702 may be configured to connect to a cloud platform to invoke the services for various computations, charting, data processing and management, and others described herein. In some other embodiments, the medical device console 702 may handle and allocate various computations, charting, data processing and management, and others described herein between the medical device console and a cloud platform so that a task may be initiated or continued or resumed on the cloud platform. In some embodiments, a medical device console 702 may be responsible for some or all of the computing, data processing, and charting needs (e.g., computing oxygen saturation level with input measurement data from sensors) and is operatively, wirelessly coupled to an electronic module (e.g., a sensor probe electronic module 708 in FIG. 7A) to receive raw measurement data or processed measurement data from the electronic module that receives the measurement data from the one or more sensors. In some of these embodiments, the electronic module may be operatively connected to the one or more sensors with wired connections (e.g., a wired connection with a fiber optic cable). In other embodiments, the electronic module may be operatively connected to the one or more sensors with wireless connections (e.g., connections via Wi-Fi, Bluetooth, Bluetooth LE, or any other suitable wireless communication protocols and mechanisms). Yet in some other embodiments, the electronic module may be operatively connected to the one or more sensors with a combination of one or more wired connections and one or more wireless connections. In some embodiments, the aforementioned electronic module may include a display that is configured to present textual, numeric, or graphic information pertaining to the measurement data received from the one or more sensors connected to the electronic module.

In some embodiments, the electronic module may be implemented to incorporate some or all the functionalities of the medical device console (e.g., various functionalities including, without limitation, computations, charting, data processing and management, and others described herein) so that a separate medical device console is no longer needed. In some of these embodiments, an electronic module (e.g., a sensor probe electronic module 708 in FIG. 7A) perform all of the functionalities of a medical device console so that a separate medical device console is no longer needed. In some other embodiments, an electronic module (e.g., a sensor probe electronic module 708 in FIG. 7A) perform some but not all of the functionalities of a medical device console so that a separate medical device console is no longer needed. In these latter embodiments, the electronic module may pass or relay functionalities that are not performed or cannot be performed on or by the electronic module to a server or a cloud platform which in turn returns the processing results back to the electronic module for review or presentation to a user. In some of these embodiments, an electronic module may include a simplified display, rather than a conventional full-blown display device, to present some information or data to a user. For example, an electronic module may include a small display screen (e.g., a small LCD or LED display screen) for presenting numeric or textual data while more complex presentations such as charting may be relayed to another display (e.g., a tablet computing device) for presentation to a user.

In some embodiments, connection may be established via protocols such as 802.11x, 802.15 (e.g., 802.15.1 for WPAN/Bluetooth connections, 802.15.2 for coexistence connections, 802.15.3 for high-rate WPAN, 802.15.3b-2005, 802.15.3c-2009, 802.15.3d-2017, 802.15.3e-2017, 802.15.3f-2017, 802.15.4 for low-rate WPAN connections, 802.15.4a, 802.15.5, 802.15.6, 802.15.7 for Visible Light Communication, 802.15.8 for Peer Aware Communications, 802.15.9 for Key Management Protocol, 802.15.10 for Layer 2 Routing, 802.15.13 for Multi-Gigabit/s Optical Wireless Communications, and others), DASH7 Alliance Protocol, or Ultra-wideband (UWB) or ultraband.

The 802.15.1 protocol may be used for WPAN or Bluetooth connections. More particularly, task group one may be based on Bluetooth technology. The 802.15.1 protocol defines physical layer (PHY) and Media Access Control (MAC) specification for wireless connectivity with fixed, portable, and moving devices within or entering personal operating space. The 802.15.2 protocol is used where task group two addresses the coexistence of wireless personal area networks (WPAN) with other wireless devices operating in unlicensed frequency bands such as wireless local area networks (WLAN).

The 802.15.3 protocol for high-rate WPAN comprises a MAC and PHY standard for high-rate (11 to 55 megabits per second) WPANs. 802.15.3a was an attempt to provide a higher speed ultra-wideband PHY enhancement amendment to IEEE 802.15.3 for applications that involve imaging and multimedia. The 802.15.3b-2005 amendment was released on May 5, 2006. It enhanced 802.15.3 to improve implementation and interoperability of the MAC. This amendment includes many optimizations, corrected errors, clarified ambiguities, and added editorial clarifications while preserving backward compatibility.

The 802.15.3c-2009 amendment constitutes a millimeter-wave-based alternative physical layer (PHY) for the existing 802.15.3 Wireless Personal Area Network (WPAN) Standard 802.15.3-2003. IEEE 802.15.3d-2017: an alternative physical layer (PHY) at the lower THz frequency range between 252 GHz and 325 GHz for switched point-to-point links is defined in this amendment. Two PHY modes are defined that enable data rates of up to 100 gigabytes per second using eight different bandwidths between 2.16 gigahertz and 69.12 gigahertz. IEEE 802.15.3e-2017 constitutes an alternative physical layer (PHY) and a modified medium access control (MAC) layer is defined in this amendment. Two PHY modes have been defined that enable data rates up to 100 gigabytes per second using the 60 gigahertz band. MIMO and aggregation methods have been defined to increase the maximum achievable communication speeds. Stack acknowledgment has been defined to improve the medium access control (MAC) efficiency when used in a point-to-point (P2P) topology between two devices.

IEEE 802.15.3f-2017 extends the RF channelization of the millimeter wave PHYs to allow for use of the spectrum up to 71 GHz. IEEE 802.15.3f was initiated because several regulatory domains extended the licensed exempt 60 gigahertz bands up to 71 gigahertz. IEEE 802.15.4 for Low Rate WPAN connections deals with low data rate but very long battery life (months or even years) and very low complexity. The standard defines both the physical (Layer 1) and data-link (Layer 2) layers of the OSI model. IEEE 802.15.4a (formally called IEEE 802.15.4a-2007) is an amendment to IEEE 802.15.4 specifying additional physical layers (PHYs) to the original standard. The principal interest was in providing higher precision ranging and localization capability (1 meter accuracy and better), higher aggregate throughput, adding scalability to data rates, longer range, and lower power consumption and cost.

IEEE 802.15.5 provides the architectural framework enabling WPAN devices to promote interoperable, stable, and scalable wireless mesh networking. This standard is composed of two parts: low-rate WPAN mesh and high-rate WPAN mesh networks. The low-rate mesh is built on IEEE 802.15.4-2006 MAC, while the high-rate mesh utilizes IEEE 802.15.3/3b MAC. The common features of both meshes include network initialization, addressing, and multi-hop unicasting. In addition, the low-rate mesh supports multicasting, reliable broadcasting, portability support, trace route, and energy saving function, and the high-rate mesh supports multi-hop time-guaranteed service. IEEE 802.15.6 task group approved a draft of a standard for Body Area Network (BAN) technologies. The draft was approved on Jul. 22, 2011 by Letter Ballot to start the Sponsor Ballot process. Task Group 6 was formed in November 2007 to focus on a low-power and short-range wireless standard to be optimized for devices and operation on, in, or around the human body (but not limited to humans) to serve a variety of applications including medical, consumer electronics, and personal entertainment.

IEEE 802.15.7 may be used for visible light communication with several new PHY layers and MAC routines to support optical camera communications (OCC) and light fidelity (Li-Fi). In March 2017, the 802.15 Working Group decided to continue 802.15.7 with OCC only, which is broadcast only, and to create a new task group 802.15.13 to work on a new standard for Li-Fi, which obviously needed a significantly revised MAC layer, besides new PHYS.

DASH7 Alliance Protocol (D7A) is an open-source wireless sensor and actuator network protocol, which operates in the 433 megahertz, 868 megahertz, and 915 megahertz unlicensed ISM band or SRD band, or both. DASH7 provides multi-year battery life, range of up to 2 kilometers, low latency for connecting with moving things, a very small open-source protocol stack, AES 128-bit shared-key encryption support, and data transfer of up to 167 kilobits per second. The DASH7 Alliance Protocol is the name of the technology promoted by the non-profit consortium called the DASH7 Alliance. Ultra-wideband (UWB, ultra-wideband, ultra-wide band and ultraband) is a radio technology that can use a very low energy level for short-range, high-bandwidth communications over a large portion of the radio spectrum. UWB was proposed for use in personal area networks, and appeared in the IEEE 802.15.3a draft PAN standard.

The sensor probe system 704 may include a sensor probe electronic module 708 that is connected to a sensor probe unit 706. In some embodiments, each of the sensor probe electronic module 708 and the sensor probe unit 706 may be enclosed in an enclosure (housing, casing, case, encasement, and the like) and the two enclosures or housings are separate and independent of one another. The sensor probe unit 706 includes one or more light sources 710 (e.g., one or more emitter circuits or light emitter circuits) that emit light beams or signals 722 in one or more different wavelengths towards a biological tissue 718. Once entering the biological tissues, the light beams or signals 722 scatter within the biological tissue 718, and a part of the light beams or signals 722 is reflected or refracted back in the form of reflected light signals 724 that are collected by one or more detectors 712 for monitoring, detecting, or collecting characteristics, or a combination, or data of a biological tissue 718 (e.g., a patient's tissue). In some embodiments, a sensor probe unit 706 may include a total of four light sources (or emitter circuits) and a total of two light detectors (or detector circuits) where each pair of a single light source and a single detector corresponds to a different distance value so that the four light sources and two light detectors for a total of eight different distance values.

Figure 7B:
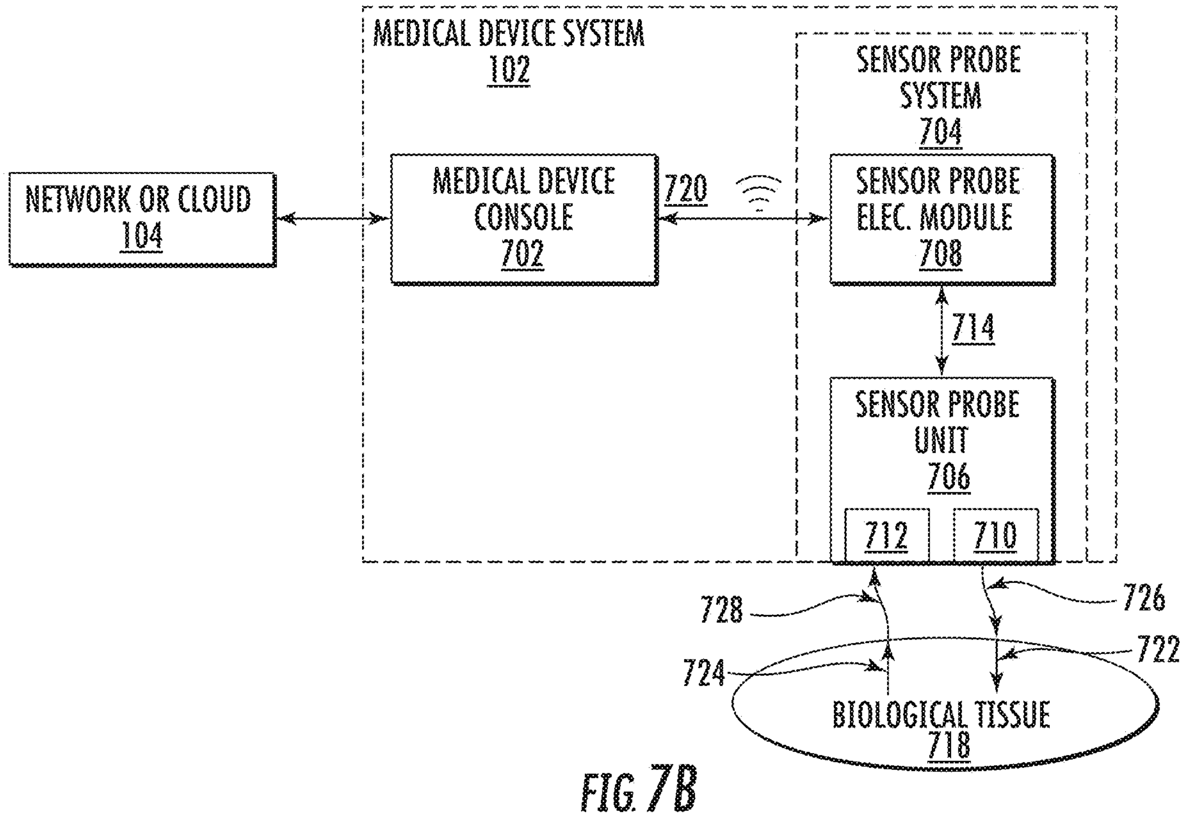
FIG. 7B shows another simplified schematic diagram of an example medical device system in which some of various techniques described herein may be implemented, according to some embodiments.

FIG. 7B shows another simplified schematic diagram of an example medical device system in which some of various techniques described herein may be implemented, according to some embodiments. The difference between the implementation shown in FIG. 7B and that shown in FIG. 7A is that the one or more light sources 710 emit respective light beams or signals 722 that are guided by one or more waveguides (e.g., a fiber optic cable) 726 that extend beyond the one or more light sources 710 to a point near (without contact) or at (with contact) the biological tissue 718.

The light beams or signals 722 exit the one or more waveguides 726 and shine on the biological tissue 718 so that a part of the light beams or signals 722 is absorbed into and scatter within the biological tissue 718 to cause reflected or refracted light signals 724. The reflected or refracted light signals 724 are then collected by and propagated through the one or more waveguides 728 (e.g., one or more separate fiber optic cables or a bundle of a plurality of optical fibers within an enclosure) so that one or more detectors 712 may detect and collect such reflected or refracted light signals 724.

Figure 7C:
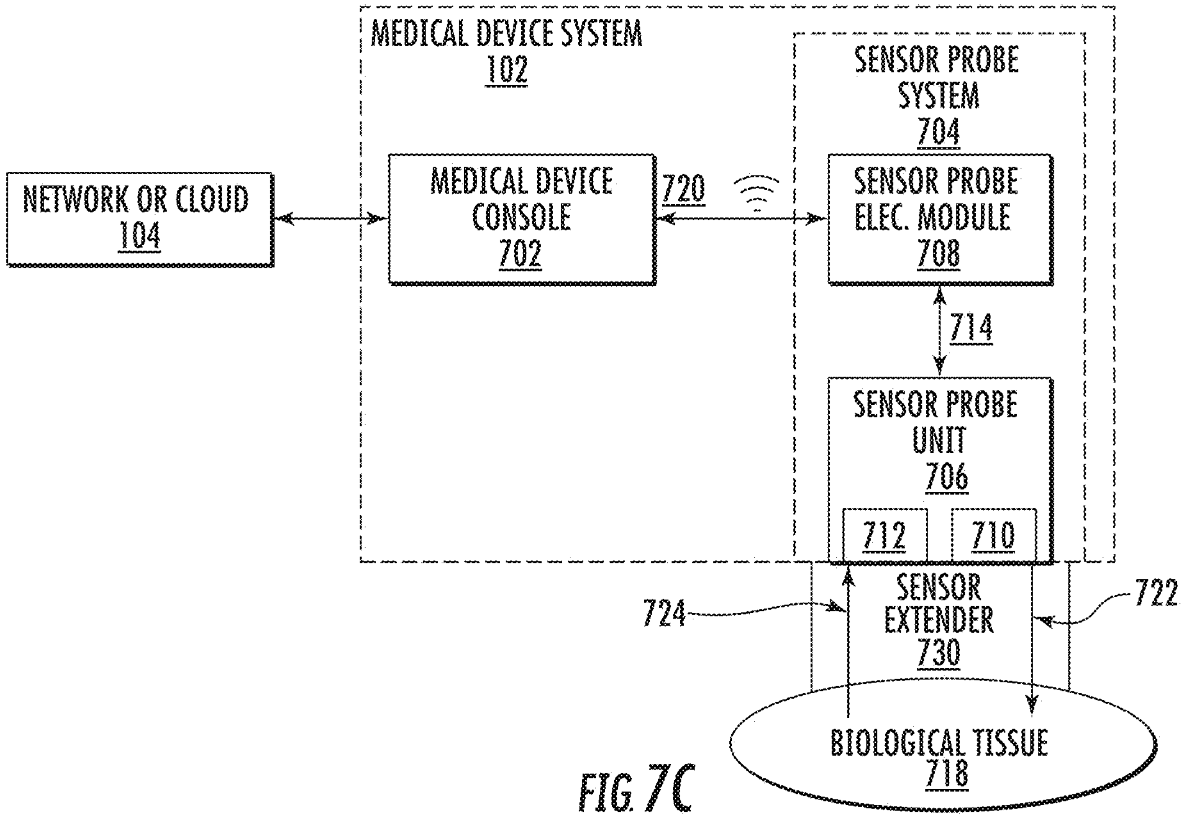
FIG. 7C shows another simplified schematic diagram of an example medical device system in which some of various techniques described herein may be implemented, according to some embodiments.

FIG. 7C shows another simplified schematic diagram of an example medical device system in which some of various techniques described herein may be implemented, according to some embodiments. The difference between the implementation shown in FIG. 7C and that in FIG. 7A or 7B is that the sensor probe unit 706 comprises or is further coupled with (e.g., in a detachable or non-detachable configuration) a sensor extender 730 through which the one or more light beams or signals 722 propagate to reach the biological tissue 718, and the scattered, reflected or refracted light signals 724 propagate to be collected by the one or more detectors 712.

A sensor extender 730 effectively extends the reach of the sensor probe unit and may comprise a variety of different form factors to fit different applications. In some embodiments, a sensor extender 730 may include one or more pairs of waveguides (e.g., one waveguide for incident light beams or signals 722 and the other waveguide for the reflected or refracted light signals 724) that guide the light beams or signals (e.g., 722 and 724) from the one or more light sources 710 and into one or more detectors 712. In an implementation, there are at least three waveguides, either two sources and one detector or two detectors and one source.

Figure 7D:
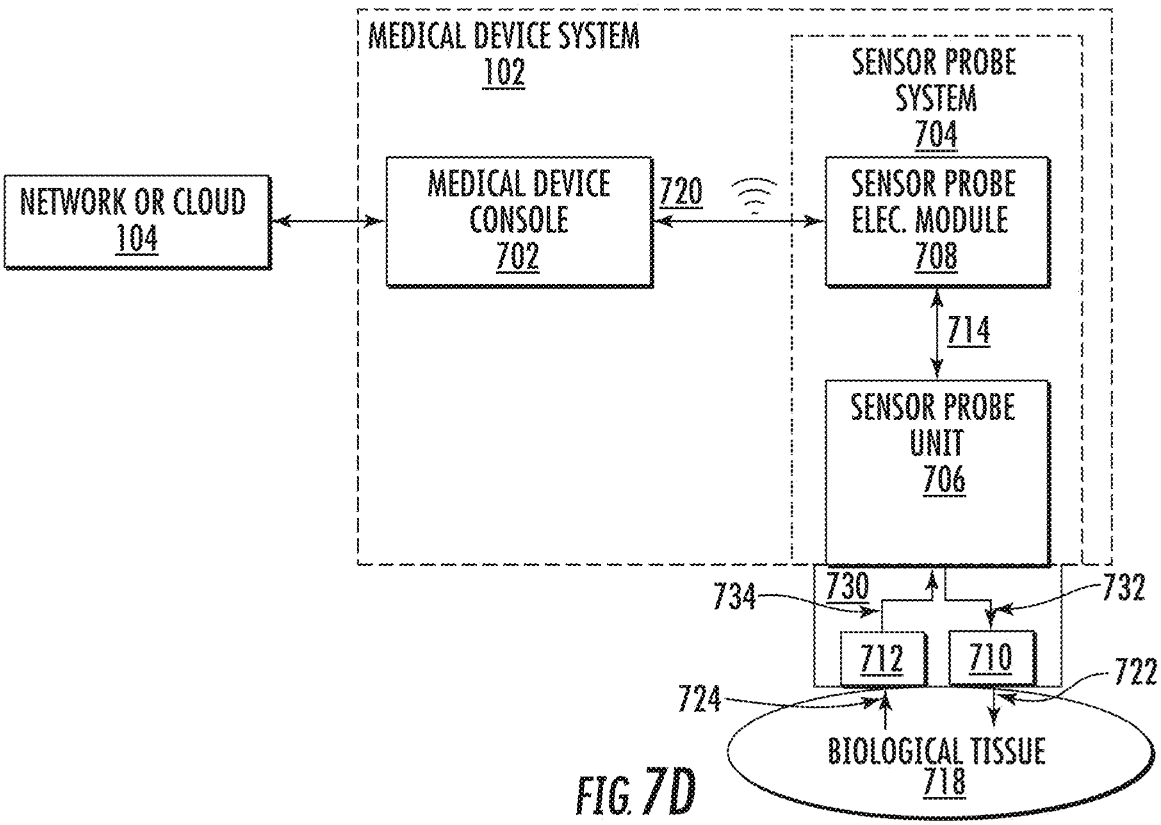
FIG. 7D shows another simplified schematic diagram of an example medical device system in which some of various techniques described herein may be implemented, according to some embodiments.

FIG. 7D shows another simplified schematic diagram of an example medical device system in which some of various techniques described herein may be implemented, according to some embodiments. The difference between the implementation shown in FIG. 7D and that in FIG. 7A, 7B, or 7C is that the sensor probe unit 706 may comprise or may be otherwise coupled with a sensor extender 730. Rather than having the one or more light sources 710 and the one or more detectors 712 within the sensor probe unit 706 (e.g., in the configurations shown in FIGS. 7A-7C), the one or more light sources 710 and/or the one or more detectors 712 may be located outside the sensor probe unit and may be connected to the sensor probe unit 706 (e.g., via one or more electrical cables).

For example, the one or more light sources 710 may be connected to the sensor probe unit 706 via one or more cables or incident conductors 732 to receive signals from the sensor probe unit so that the one or more light sources 710 may emit the one or more light beams or signals in a controlled manner (e.g., light beams or signals with a controlled duration, a controlled pattern, and/or controlled intensity, and others) Similarly, scattered, reflected or refracted light signals 724 may be collected by one or more detectors 712 that is also located in the sensor extender 730. The collected light signals 724 may be transmitted as analog signals via the return cable 734 back to the sensor probe unit 706 in some embodiments. In some other embodiments, the collected light signals 724 may be first converted into digital signals that are subsequently transmitted as digital signals via the return cable 734 back to the sensor probe unit 706. In these latter embodiments, the sensor extender 730 may include one or more analog-to-digital converters that convert incoming analog signals into digital signals.

In some of the various embodiments shown in FIG. 7D, the one or more light sources 710 and the one or more detectors 712 may be located at the end closer to the biological tissue 718. In some other embodiments, the one or more light sources 710 and/or the one or more detectors 712 may be located further away from the end closer to the biological tissue 718 so that the light beams or signals may be guided by respective waveguides (e.g., fiber optic cables) at least for a length of travel within the sensor extender (e.g., before finally exiting the external boundary of the sensor extender 730 for incident light beams or signals 722 or after entering the external boundary of the sensor extender 730 from the biological tissue 718 and before being collected by the one or more detectors or sensors 712 for the reflected or refracted light signals 724).

Figure 7E:
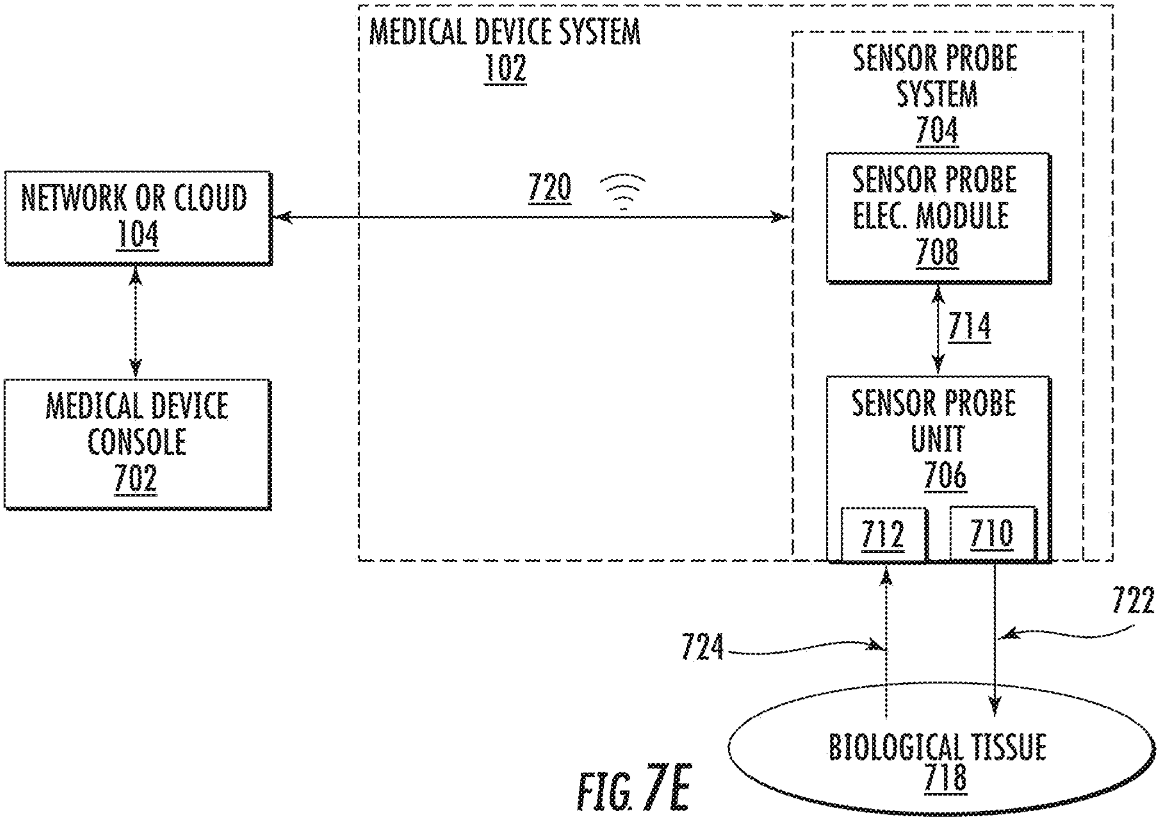
FIG. 7E shows another simplified schematic diagram of an example medical device system connected to an example medical device console via a network or cloud computing environment for facilitating the implementation of various techniques described herein may be implemented, according to some embodiments.

FIG. 7E shows another simplified schematic diagram of an example medical device system connected to an example medical device console via a network or cloud computing environment for facilitating the implementation of various techniques described herein may be implemented, according to some embodiments. The example implementation of the medical device system 102 including the sensor probe system 704 in FIG. 7E is similar to that shown in FIG. 7A although it shall be noted that the implementation in any of FIGS. 7B-7D may also be used in the implementation shown in FIG. 7E. In FIG. 7E, the medical device console 702 is no longer physically located within or near the physical confine or vicinity of the medical device system 102 yet is nevertheless connected to the medical device system 102 via the network or cloud 104 (e.g., 104 in FIG. 1). For example, the medical device system 102 including the sensor probe system may be physically located within a room (e.g., an operating room) while the medical device console may be physically located at a different location (e.g., a different room, a different building, a different geographical location, and others) and is connected to the medical device system 102 via network or cloud 104.

Figure 7F:
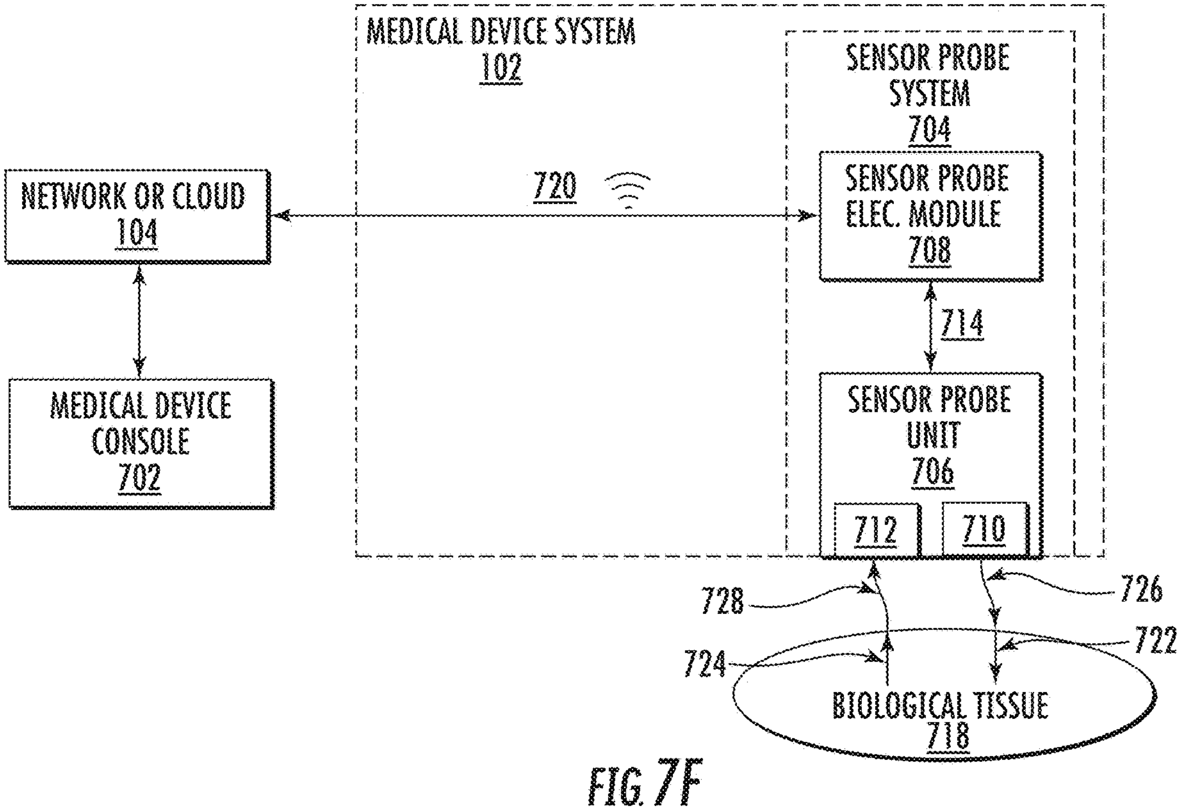
FIG. 7F shows another simplified schematic diagram of an example medical device system connected to an example medical device console via a network or cloud computing environment for facilitating the implementation of various techniques described herein may be implemented, according to some embodiments.

FIG. 7F shows another simplified schematic diagram of an example medical device system connected to an example medical device console via a network or cloud computing environment for facilitating the implementation of various techniques described herein may be implemented, according to some embodiments. The example implementation of the medical device system 102 including the sensor probe system 704 in FIG. 7F is similar to that shown in FIG. 7B although it shall be noted that the implementation in any of FIGS. 7A and 7C-7D may also be used in the implementation shown in FIG. 7F. In FIG. 7F, the medical device console 702 is no longer physically located within or near the physical confine or vicinity of the medical device system 102 yet is nevertheless connected to the medical device system 102 via the network or cloud 104 (e.g., 104 in FIG. 1). For example, the medical device system 102 including the sensor probe system may be physically located within a room (e.g., an operating room) while the medical device console may be physically located at a different location (e.g., a different room, a different building, a different geographical location, and others) and is connected to the medical device system 102 via network or cloud 104.

Figure 7G:
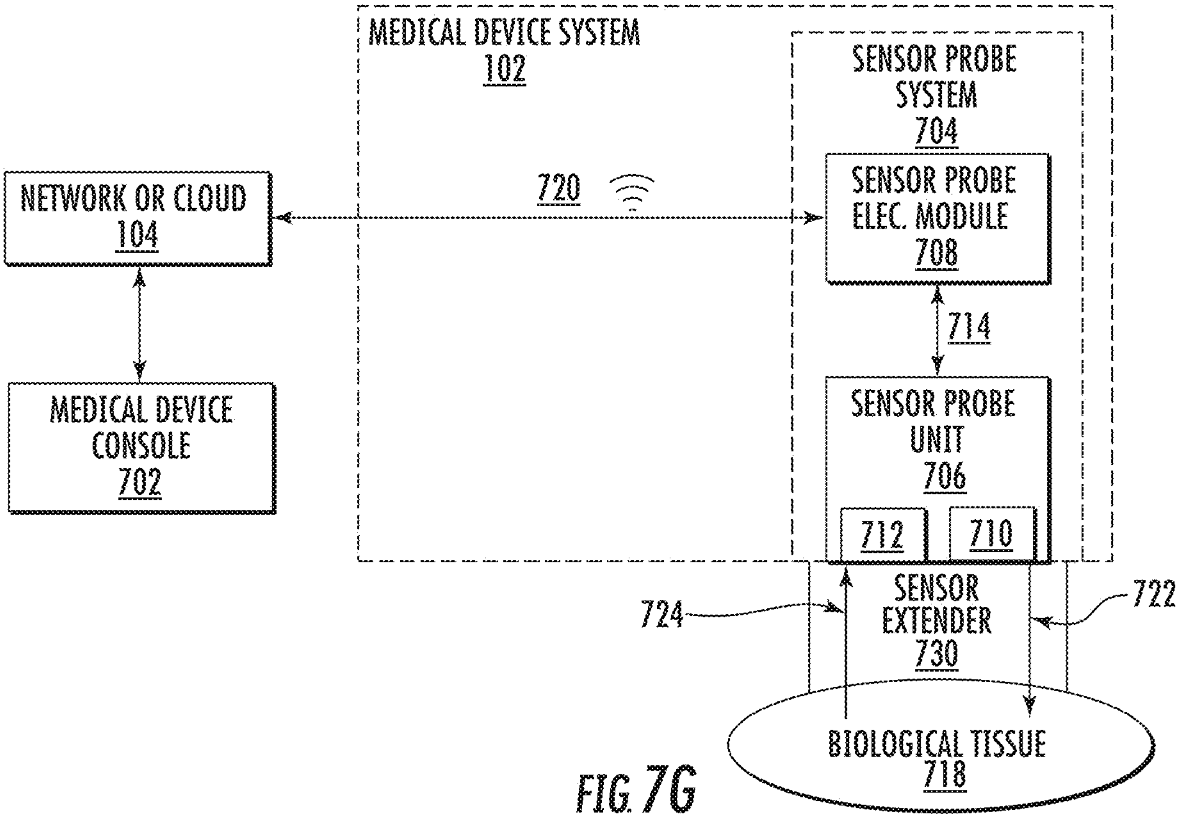
FIG. 7G shows another simplified schematic diagram of an example medical device system connected to an example medical device console via a network or cloud computing environment for facilitating the implementation of various techniques described herein may be implemented, according to some embodiments.

FIG. 7G shows another simplified schematic diagram of an example medical device system connected to an example medical device console via a network or cloud computing environment for facilitating the implementation of various techniques described herein may be implemented, according to some embodiments. The example implementation of the medical device system 102 including the sensor probe system 704 in FIG. 7G is similar to that shown in FIG. 7C although it shall be noted that the implementation in any of FIGS. 7A-B and 7D may also be used in the implementation shown in FIG. 7G. In FIG. 7G, the medical device console 702 is no longer physically located within or near the physical confine or vicinity of the medical device system 102 yet is nevertheless connected to the medical device system 102 via the network or cloud 104 (e.g., 104 in FIG. 1).

For example, the medical device system 102 including the sensor probe system may be physically located within a room (e.g., an operating room) while the medical device console may be physically located at a different location (e.g., a different room, a different building, a different geographical location, and others) and is connected to the medical device system 102 via network or cloud 104. The implementations shown in FIGS. 7E-7G may be configured in such a way that one or more medical device consoles 720 may be used to connect to a plurality of medical device systems 102 in a manner similar to that for Internet of Things (IoT) that describes devices with sensors (e.g., a sensor probe system 704), processing ability, software, and other technologies that connect and exchange data (e.g., data autonomously collected by sensor probe systems 704) with other devices and systems (e.g., one or more medical device consoles 702, client systems 108 in FIG. 1, and others) over the Internet or other communications networks.

Figure 7H:
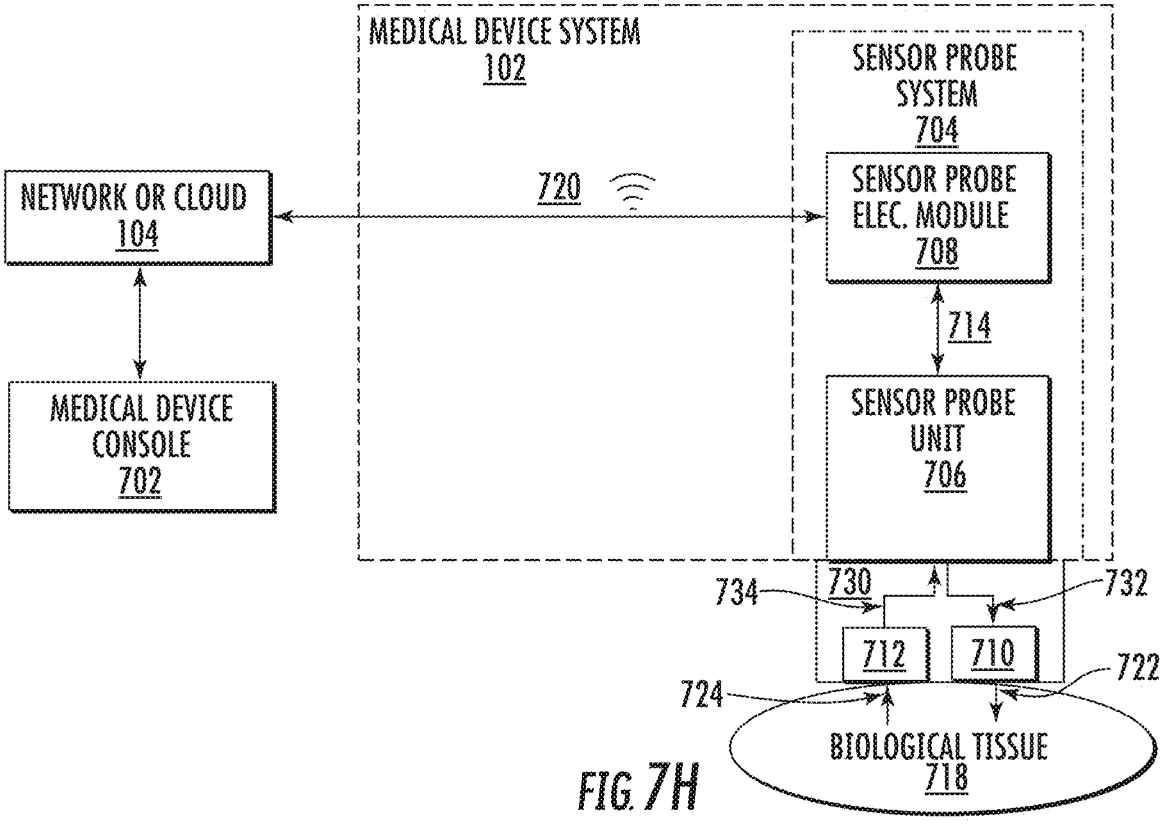
FIG. 7H shows another simplified schematic diagram of an example medical device system connected to an example medical device console via a network or cloud computing environment for facilitating the implementation of various techniques described herein may be implemented, according to some embodiments.

FIG. 7H shows another simplified schematic diagram of an example medical device system connected to an example medical device console via a network or cloud computing environment for facilitating the implementation of various techniques described herein may be implemented, according to some embodiments. The example implementation of the medical device system 102 including the sensor probe system 704 in FIG. 7H is similar to that shown in FIG. 7D although it shall be noted that the implementation in any of FIGS. 7A-7C may also be used in the implementation shown in FIG. 7H. In FIG. 7H, the medical device console 702 is no longer physically located within or near the physical confine or vicinity of the medical device system 102 yet is nevertheless connected to the medical device system 102 via the network or cloud 104 (e.g., 104 in FIG. 1).

For example, the medical device system 102 including the sensor probe system may be physically located within a room (e.g., an operating room) while the medical device console may be physically located at a different location (e.g., a different room, a different building, a different geographical location, and others) and is connected to the medical device system 102 via network or cloud 104. The implementations shown in FIG. 7H may be configured in such a way that one or more medical device consoles 720 may be used to connect to a plurality of medical device systems 102 in a manner similar to that for Internet of Things (IoT) that describes devices with sensors (e.g., a sensor probe system 704), processing ability, software, and other technologies that connect and exchange data (e.g., data autonomously collected by sensor probe systems 704) with other devices and systems (e.g., one or more medical device consoles 702, client systems 108 in FIG. 1, and others) over the Internet or other communications networks.

Figure 7I:
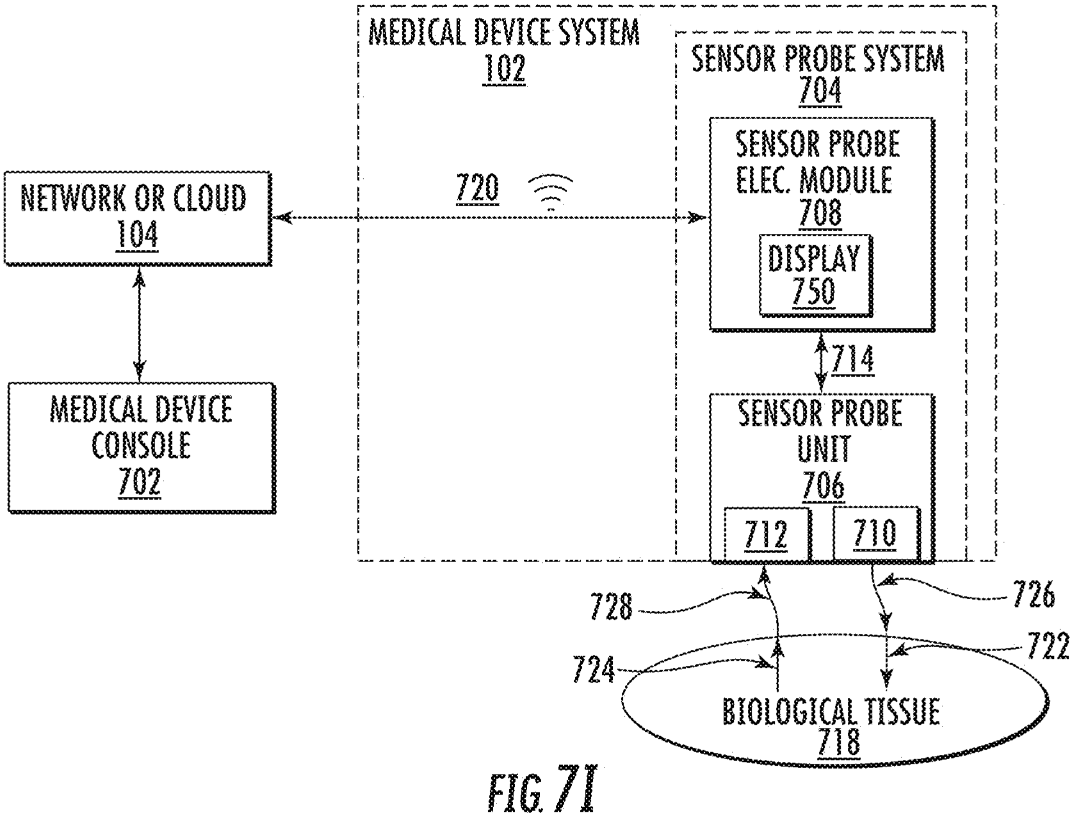
FIGS. 7I-7L show some other simplified schematic diagrams of example medical devices for facilitating the implementation of various techniques described herein may be implemented, according to some embodiments.

FIG. 7I shows another simplified schematic diagram of an example medical device connected to an example medical device console via a network or cloud computing environment for facilitating the implementation of various techniques described herein may be implemented, according to some embodiments. Compared with FIGS. 7A-7D, the example implementation of the medical device system in FIG. 7I does not include a medical device console (702) where some or all of the functionalities of the medical device in the example implementations of FIGS. 7A-7D are provided by the sensor probe electronic module 708. Moreover, compared with FIGS. 7A-7H, the sensor probe electronic module 708 includes a display 750.

In these embodiments shown in FIGS. 7I-7L, the sensor probe electronic module may be implemented to incorporate some or all the functionalities of the medical device console 702 (e.g., various functionalities including, without limitation, computations, charting, data processing and management, and others described herein) so that a separate medical device console is no longer needed. In some of these embodiments, an sensor probe electronic module perform all of the functionalities of a medical device console so that a separate medical device console is no longer needed as shown in FIGS. 7I-7L. In some other embodiments, a sensor probe electronic module performs some but not all of the functionalities of a medical device console so that a separate medical device console is no longer needed. In these latter embodiments, the sensor probe electronic module may pass or relay functionalities that are not performed or cannot be performed on or by the sensor probe electronic module to a server or a cloud platform which in turn returns the processing results back to the sensor probe electronic module for review or presentation to a user. In some of these embodiments, a sensor probe electronic module may include a simplified display, rather than a conventional full-blown display device, to present some information or data to a user. For example, an sensor probe electronic module may include a small display screen (e.g., a small LCD or LED display screen) for presenting numeric or textual data while more complex presentations such as charting may be relayed to another display (e.g., a tablet computing device) for presentation to a user.

Figure 7J:
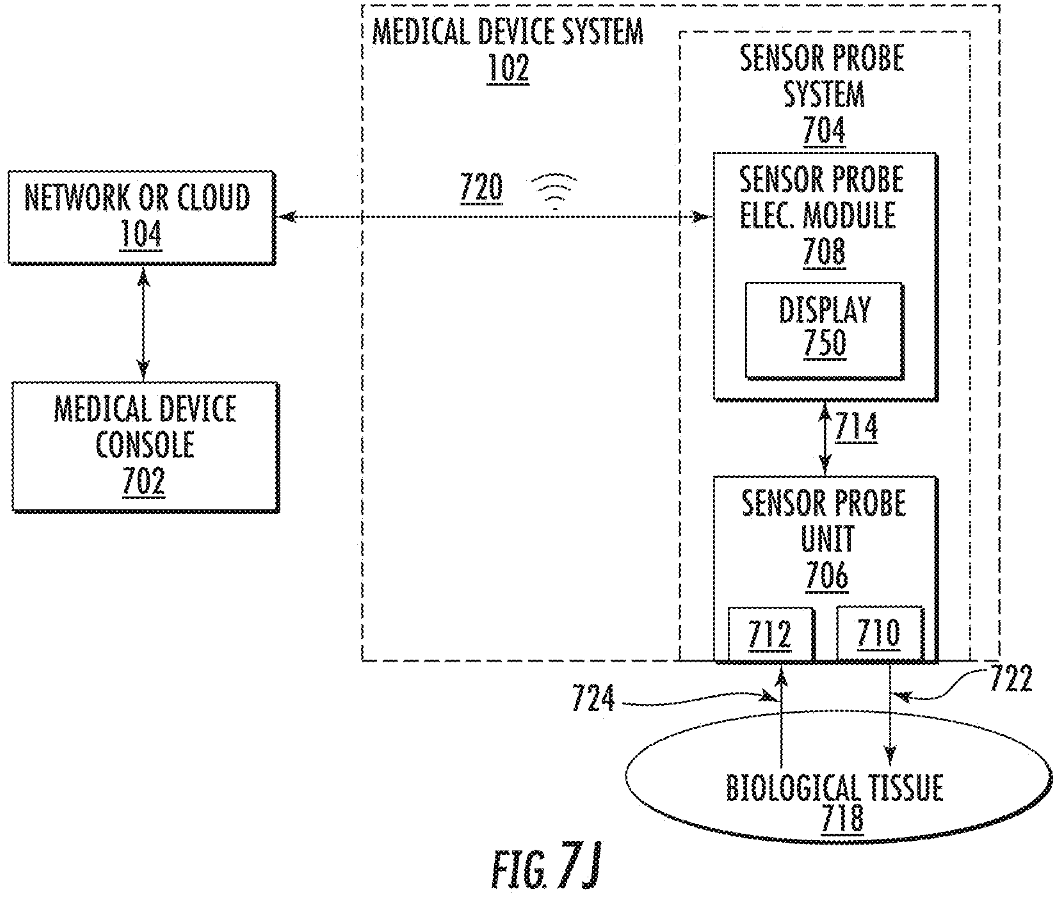

FIG. 7J shows another simplified schematic diagram of an example medical device connected to an example medical device console via a network or cloud computing environment for facilitating the implementation of various techniques described herein may be implemented, according to some embodiments. Compared with FIGS. 7A-7D, the example implementation of the medical device system in FIG. 7J does not include a medical device console (702) where some or all of the functionalities of the medical device in the example implementations of FIGS. 7A-7D are provided by the sensor probe electronic module 708. Moreover, the implementation shown in FIG. 7J is substantially similar to that in FIG. 7E, but the sensor probe electronic module 708 in FIG. 7J includes a display 750 that serves substantially purposes as described immediately above with reference to FIG. 7I.

Figure 7K:
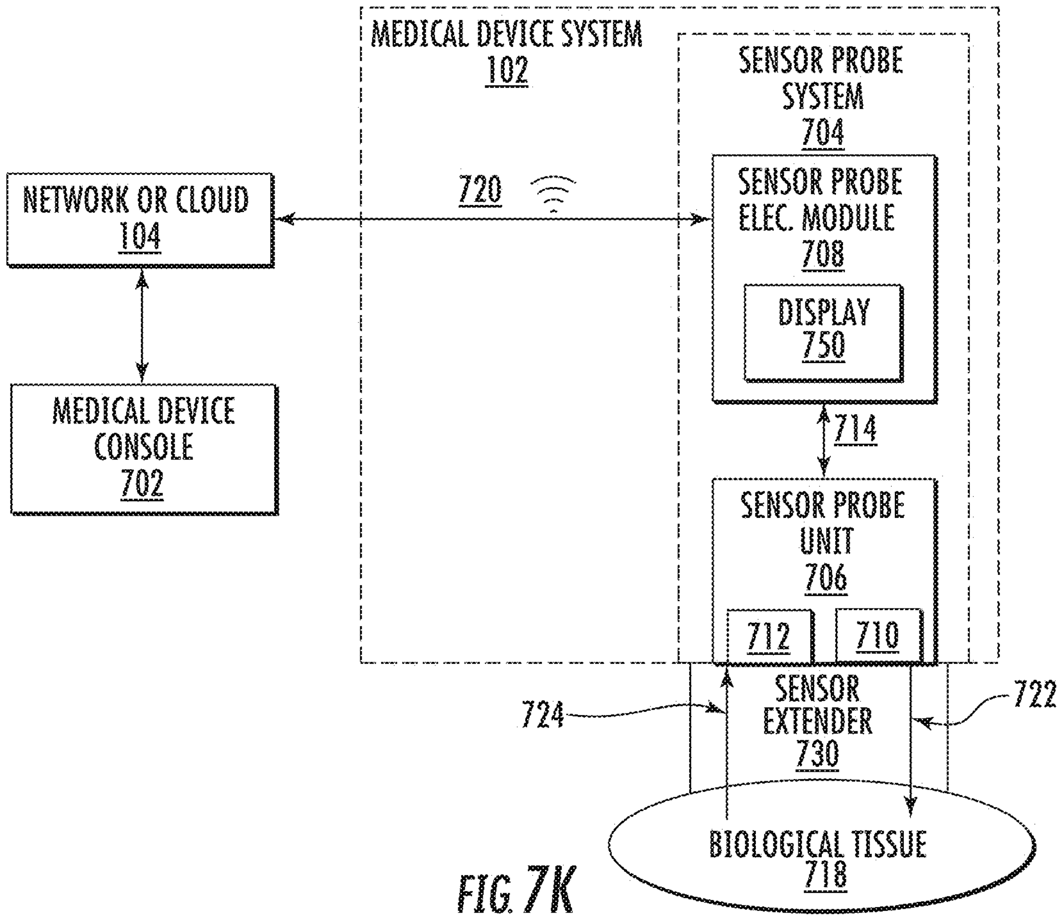

FIG. 7K shows another simplified schematic diagram of an example medical device connected to an example medical device console via a network or cloud computing environment for facilitating the implementation of various techniques described herein may be implemented, according to some embodiments. Compared with FIGS. 7A-7D, the example implementation of the medical device system in FIG. 7K does not include a medical device console (702) where some or all of the functionalities of the medical device in the example implementations of FIGS. 7A-7D are provided by the sensor probe electronic module 708. Moreover, the implementation shown in FIG. 7K is substantially similar to that in FIG. 7G, but the sensor probe electronic module 708 in FIG. 7K includes a display 750 that serves substantially purposes as described immediately above with reference to FIG. 7I.

Figure 7L:
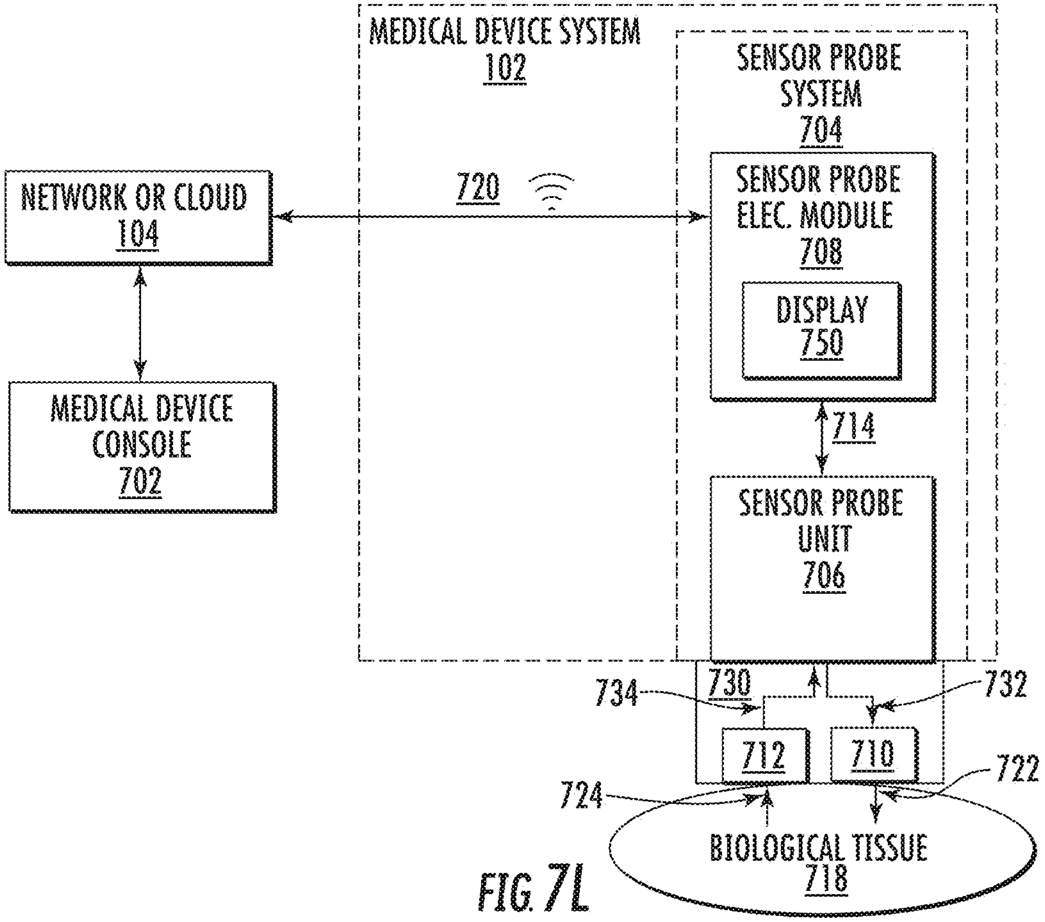

FIG. 7L shows simplified schematic diagram of an example medical device connected to an example medical device console via a network or cloud computing environment for facilitating the implementation of various techniques described herein may be implemented, according to some embodiments. Compared with FIGS. 7A-7D, the example implementation of the medical device system in FIG. 7L does not include a medical device console (702) where some or all of the functionalities of the medical device in the example implementations of FIGS. 7A-7D are provided by the sensor probe electronic module 708. Moreover, the implementation shown in FIG. 7L is substantially similar to that in FIG. 7H, but the sensor probe electronic module 708 in FIG. 7L includes a display 750 that serves substantially purposes as described immediately above with reference to FIG. 7J.

Figure 8:
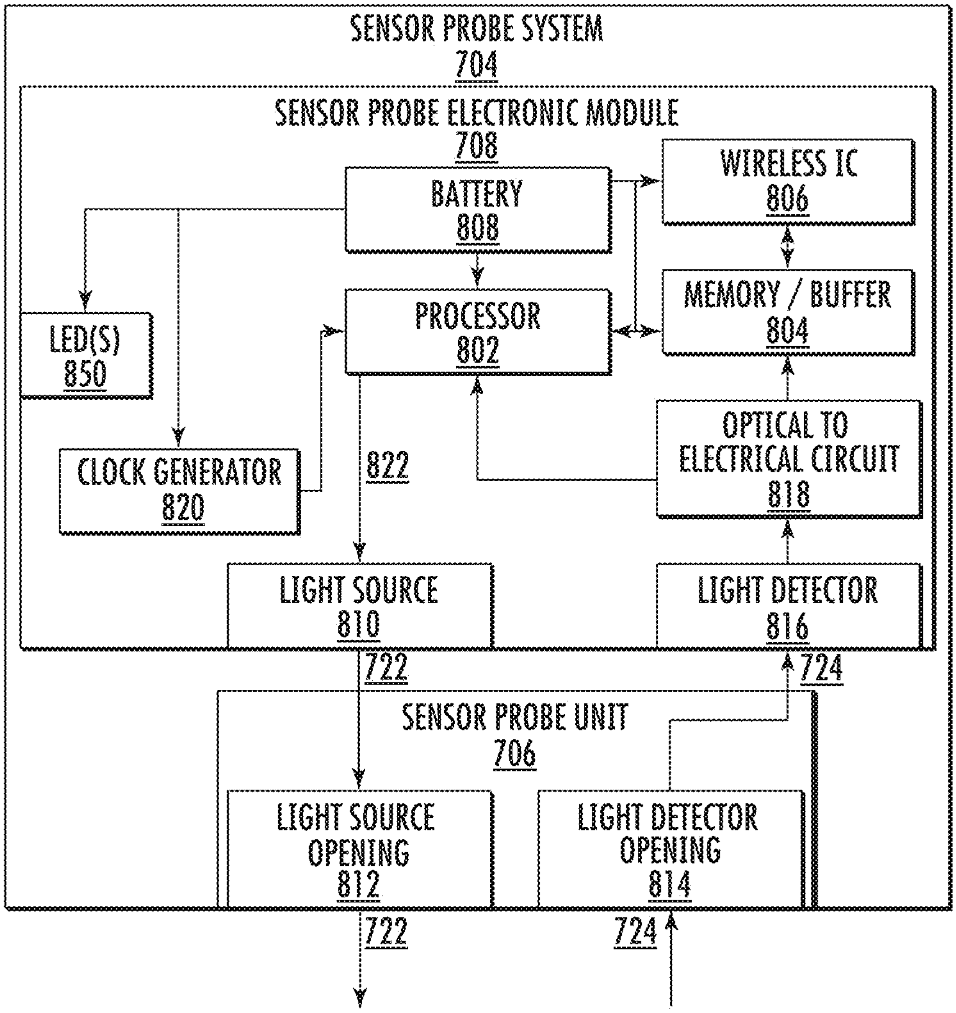
FIG. 8 shows a simplified schematic diagram of an example sensor probe system, according to some embodiments.

FIG. 8 shows a simplified schematic diagram of an example sensor probe system, according to some embodiments. In these embodiments, a sensor probe system 704 may include a sensor probe electronic module 708 that transmits one or more incident light beams or signals 722 to and receive one or more reflected or refracted light beams or signals 724 from a sensor probe unit 706. In these embodiments, one or more light sources 810 respectively emit the one or more incident light beams or signals 722 into the sensor probe unit 706 through one or more light source openings 812 of the sensor probe unit 706; and the one or more reflected or refracted light beams or signals 724 enter one or more light detector openings 814 of the sensor probe unit 706 and propagate back to one or more light detectors 816 of the sensor probe electronic module 708. Such a structure may be made of materials such as, without limitation, glass, plastic, or other suitable polymeric materials suitable for a waveguide. In some embodiments, a light source includes two single-wavelength light emitter circuits (e.g., two single-wavelength light emitting diodes) and corresponds to a single light source structure where a single detector also corresponds to a respective detector structure.

Some embodiments relate to a probe with a sensor (e.g., a sensor probe unit or a sensor probe system referred to herein) that supports light sources (e.g., source optical structures) and detectors (e.g., detector structures) such that the sources have a substantially nonsymmetric arrangement relative to the detectors. According to one aspect of these embodiments, a sensor arrangement that is suitable for use in an optical imaging system such as various systems described herein and is arranged to contact a body of a human such as tissue includes a first source structure, a second source structure, and a detector arrangement. The first source structure provides a first beam of light and the second source structure provides a second beam of light.

The detector arrangement includes detector structures and receives the first beam of light and the second beam of light after the first beam of light and the second beam of light are reflected off of the body. The detector arrangement is arranged to define a first axis, and a distance from the first source structure to the first axis is not equal to a distance from the second source structure to the first axis.

In one embodiment, a difference between the distance from the first source structure to the first axis and the distance from the second source structure is at least approximately 0.03 inches. In such an embodiment, the distance from the first source structure to the first axis may be approximately 0.020 inches and the distance from the second source structure to the first axis may be approximately 0.24 inches.

It shall be noted that various embodiments described herein may refer to some numeric values such as one or more dimensions or other types of numeric values, that such numeric values refer to the as-designed or as-specified nominal values yet are nevertheless subject to various variations such as manufacturing tolerances, slacks in one or more design features for manufacturability (e.g., ease of assembly or service), machine specifications (e.g., measurement accuracies), and others in various embodiments described herein. For example, the aforementioned distance from the first source structure to the first axis may be approximately 0.020 inches indicates that the aforementioned distance is designed to be 0.020 inches, yet the actual dimensions in an actual implementation may be subject to manufacturing tolerances that may be subject to the control of the design of the implementation and hence is described as "approximately 0.020 inches."

For example, a numeric value may be subject to a range of permissible manufacturing tolerances within which a feature is considered as within the specification of the design. Such a range may be expressed in absolute numeric values or percentage of the nominal value. For example, a nominal numeric value may be subject to a range of permissible tolerances of plus or minus 0.001 inches, plus or minus 0.002 inches, plus or minus 0.005 inches, plus or minus 0.010 inches, plus or minus 0.020 inches, and others, or tighter tolerance ranges such as plus 0 or minus 0.002 inches, plus 0.002 or minus 0 inches, plus 0.005 or minus 0 inches, plus 0 or minus 0.005 inches, and others. In some embodiments, the permissible tolerances may be a range of percentages of the nominal value to which the permissible tolerances apply.

For example, the aforementioned 0.020 inches may be subject to a permissible tolerance range such as plus or minus 5 percent, plus or minus 10 percent, plus or minus 20 percent, and others, or a tighter permissible tolerance range such as plus 0 percent or minus 5 percent, plus 0 percent or minus 2 percent, plus 5 percent or minus 0 percent, plus 2 percent or minus 0 percent, and others. A design slack denotes that is intentionally designed into a feature.

For example, a mating opening receiving a mating feature (e.g., a light source structure positioned relative to a light source to allow the light emitted from the light source to pass through the light source structure) may be designed to be, for example, 0.020 inches (or any other suitable dimensions) or 5 percent (or another suitable percentages) larger than the corresponding dimension of the light source to ensure that the light emitted from the light source to pass through the light source structure. Such a slack, when the components are finally assembled or integrated, may allow such mating components to move relative to each other and thus further cause deviations from the nominal, relative positions of these mating components.

Similarly, a device may be designed to operate to produce a nominal value of output based on a nominal value of input. Nonetheless, various intrinsic and/or extrinsic characteristics of the device or the components thereof may nevertheless subject to some tolerances. Some or all of the aforementioned tolerances and/or slacks may contribute to deviations of an actual feature as manufactured or measured to deviate from its nominal value. Any modifiers of a nominal numeric value (e.g., "about," "substantially," "approximately," "around," and others) thus refers to the numeric value as the as-designed or as-specified value that is subject to one or more of the aforementioned tolerances or slacks.

In an embodiment, a probe with a sensor or a sensor head that has source structures in a nonsymmetric orientation with respect to detector structures enables the sensor head to be utilized to monitor tissue with an underlying anatomy that is not substantially symmetric. The lack of symmetry also effectively loosens manufacturing tolerances associated with the manufacture of such sensor. Any attenuation associated with the offset orientation of optical optical structures that are coupled to light sources is typically compensated for through the use of software executing with respect to an optical imaging system. Hence, the amount of compensation applied may be relatively easily varied as needed to accommodate inaccuracies in the positioning of optical structures with respect to the sensor.

According to another aspect of the present disclosure, a sensor arrangement that is suitable for use in an optical imaging system includes a first source structure that is arranged to provide a first beam of light and a second source structure that is arranged to provide a second beam of light. The sensor arrangement also includes a detector arrangement that has a first detector structure and a second detector structure. The detector arrangement is arranged to receive the first beam of light and the second beam of light after the first beam of light and the second beam of light are reflected off of or transmitted through tissue. An orientation of the first source structure with respect to the detector arrangement is not symmetric relative to an orientation of the second source structure with respect to the detector arrangement.

According to yet another aspect of the present disclosure, a method for taking an oxygen saturation measurement of tissue using an optical system that utilizes a probe with a sensor head in which a first source structure and a second source structure are offset relative to detector structures involves positioning the sensor head in contact with the tissue and transmitting light into the tissue through the first source structure and the second source structure. The method also involves receiving reflected light from the tissue at the detector structures that includes attenuation characteristics, and processing the reflected light using a number of photodetectors. Processing the reflected light using the number of photodetectors includes compensating for the attenuation characteristics using an attenuation compensator.

In accordance with still another aspect of the present disclosure, a probe which may be used as a part of an optical system to monitor oxygen levels in tissue includes a coupling interface that allows the probe to be coupled to light sources and detectors. A sensor head of the probe is arranged to contact the tissue, and supports a first source structure, a second source structure, and a detector arrangement. The first source structure and the second source structure are coupled to the light sources via the coupling interface, while the detector arrangement is coupled to the detectors through the coupling interface. An orientation of the first source structure relative to the detector arrangement is not symmetric with respect to an orientation of the second source structure relative to the detector arrangement.

In one embodiment, the detector arrangement includes detector structures. In such an embodiment, the detector arrangement receives the first beam of light and the second beam of light after the first beam of light and the second beam of light are reflected off of or transmitted through the tissue. The detector arrangement defines a first axis that passes through each detector structure of the detector structures such that a distance from the first source structure to the first axis is unequal to a distance from the second source structure to the first axis.

One embodiment is directed to a probe including: a cable interface, the cable interface being adapted to allow the probe to be connected to at least two radiation sources and at least one photodetector, where the radiation sources and a first photodetector are external to the probe; and a sensor head including a first source structure, a second source structure, and a first detector structure, the first source structure and the second source structure being arranged to be connected to the radiation sources via the cable interface, the first detector structure being arranged to be connected to the first photodetector via the cable interface.

One embodiment is directed to a probe including: a cable interface, the cable interface being adapted to allow the probe to be connected to at least two radiation sources and a at least two photodetectors, where the radiation sources and a first and second photodetector are external to the probe; and a sensor head including a first source structure, a first detector structure, and a second detector structure, the first source structure being arranged to be connected to the radiation sources via the cable interface, the first detector structure being arranged to be connected to the first photodetector via the cable interface, the second detector structure being arranged to be connected to the second photodetector via the cable interface.

One embodiment is directed to a probe including: a cable interface, the cable interface being adapted to allow the probe to be connected to at least two radiation sources and at least one photodetector, where the radiation sources and a first, second, third, and fourth photodetector are external to the probe; and a sensor head including a first source structure, a second source structure, a first detector structure, a second detector structure, a third detector structure, and a fourth detector structure. The first source structure and the second source structure is arranged to be connected to the radiation sources via the cable interface, the first detector structure is arranged to be connected to the first photodetector via the cable interface, a second detector structure is arranged to be connected to a second photodetector via the cable interface, a third detector structure is arranged to be connected to a third photodetector via the cable interface, and a fourth detector structure is arranged to be connected to the fourth photodetector via the cable interface.

The controller, processor, processor core, or thread of execution 802 may control the one or more light sources 801 using a control signal 822. In some embodiments, the sensor probe system 704 provides digital intensity control where the intensity of a light source (e.g., 810) may be controlled via pulse width modulation (PWM), where the controller, processor, processor core, or thread 802 pulses a signal many times per second. The period and the amplitude of the PWM signal remain constant, but when adjusting the intensity, the width of the pulsed signal may be adjusted. In these embodiments, an electrical characteristic (e.g., the average voltage) over delta t may determine the intensity. For example, the longer the pulse, the higher the intensity.

One of the benefits of using PWM is that a light source is being strobed, allowing for more time to dissipate heat. There exists a linear relationship between the intensity and number of intensity steps, which makes setting the intensity easier. When strobing a light source 810 such as an LED (light emitting diode) light source, a controller may be configured to initiate a light pulse as soon as it receives an external trigger signal. This external trigger signal may come from a variety of components. After receiving the trigger, the controller, processor, processor core, or thread 802 turns on the LED light source for a short, pre-defined period of time.

In addition to the one or more light sources 810 and one or more light detectors 816, the sensor probe electronic module 708 may further include an optical electrical circuit 818 (e.g., transimpedance amplifier (TIA)) that may convert or otherwise process the analog reflected or refracted light signals 724 received at the light detector 816 into electrical or processed signals which may then be provided to a controller, processor, a processor core, or a thread of execution thereof 802 to further process the processed or electrical signals in one or more processor cycles that are generated by a clock generator 820 for synchronizing the operations of the sensor probe electronic module 708. In some embodiments, the clock generator 820 may be built into the processor or controller 802. The electrical signals may be analog in some embodiments or digital in some other embodiments. In some embodiments, the electrical signals may be further converted via an analog-to-digital converter (not shown) before being forwarded to the controller, processor, processor core, or thread 802 coupled to the memory or buffer 804 for further processing.

In some embodiments, the optical to electrical circuit 818 may include an analog front end (AFE) which may also be referred to as a front-end circuit and is a circuit that conditions analog signals and interfaces such analog signals with other systems and may include, for example but not limited to, one or more analog amplifiers, one or more filters, and/or application-specific integrated circuit (ASICs). In some of these embodiments, the optical to electrical circuit 818 (e.g., an AFE) may translate or convert analog signals from the sensor probe unit 706 for processing and/or transmission although the optical to electrical circuit 818 may process the received signals from the light source(s) 810 (e.g., filtering) and relay the processed, received optical signals to the processor or controller 802 for conversion into digital signals for wireless transmission via the wireless IC 806. In addition or in the alternative, an AFE may filter out unwanted or undesired noise with a programmable bandwidth to leave only the desired signals. In some embodiments, the optical to electrical circuit 818 may support a first number of light sources 810 (e.g., M light sources) and a second number of detectors 816 (e.g., N detectors) to support up to M×N signal phases where the optical to electrical conversion circuit 818 may acquire the signals from each phase in a synchronized manner and stored in a buffer (e.g., a first-in, first-out buffer) that may be read out by using, for example, an serial peripheral interface (SPI) or an inter-integrated circuit (I^2C or "I squared C") interface. In some embodiments, the sensor probe system 704 or the sensor probe electronic module 708 may include one or more light emitting diodes (LEDs) 850 which may be separately powered to indicate, for example, the respective operational states of the sensor probe system 704, a portion thereof (e.g., the sensor probe electronic module 708), or one or more components thereof (e.g., the light sources 810, the detectors 816, wireless IC 806, and others) For example, these one or more LEDs may indicate whether a specific component or a module is powered on, connection status and/or signal strength, operation state, battery state, and others. These one or more LEDs may be implemented in the sensor probe system 704, in the sensor probe electronic module 708, and/or the sensor probe unit 706.

The clock generator 820 may comprise a master clock that controls the synchronizations of both the sensor probe electronic module 708 and the sensor probe unit 706 in some embodiments. In some other embodiments, separate clock generators may be used to respectively control the synchronizations of both the sensor probe electronic module 708 and the sensor probe unit 706. In some embodiments, the clock generator 820 is located in an integrated circuit (e.g., a chipset) and is thus different and separate from clock generator that controls the speed at which the controller or processor 802 operates. Further, the processor and memory may be integrated into an integrated circuit referred to as a controller IC or chip, which would operate as part of a stored-program state machine or computer.

The controller, processor, processor core, or thread of execution 802 may be directly or indirectly coupled to a wireless integrated circuit 806 that may wirelessly transmit and receive data in the form of packets. For example, the sensor probe system 704 may transmit the collected reflected or refracted light signals 724 or a representation thereof to, for example, a medical device system (e.g., a medical device system 102 in FIG. 1) via the wireless integrated circuit 806.

The electrical signal may also be optionally forwarded to a memory or buffer 804 for temporary storage. For example, the electrical signals may be stored in memory for further processing by the controller, processor, processor core, or thread of execution 802. Various components described herein with reference to FIG. 8 may be powered via a battery 808. In some embodiments, the battery 808 comprises a one-time use battery or rechargeable battery. In some embodiments, the sensor probe system 704 may further optionally comprise a charging circuit that recharges the rechargeable battery.

Figure 9:
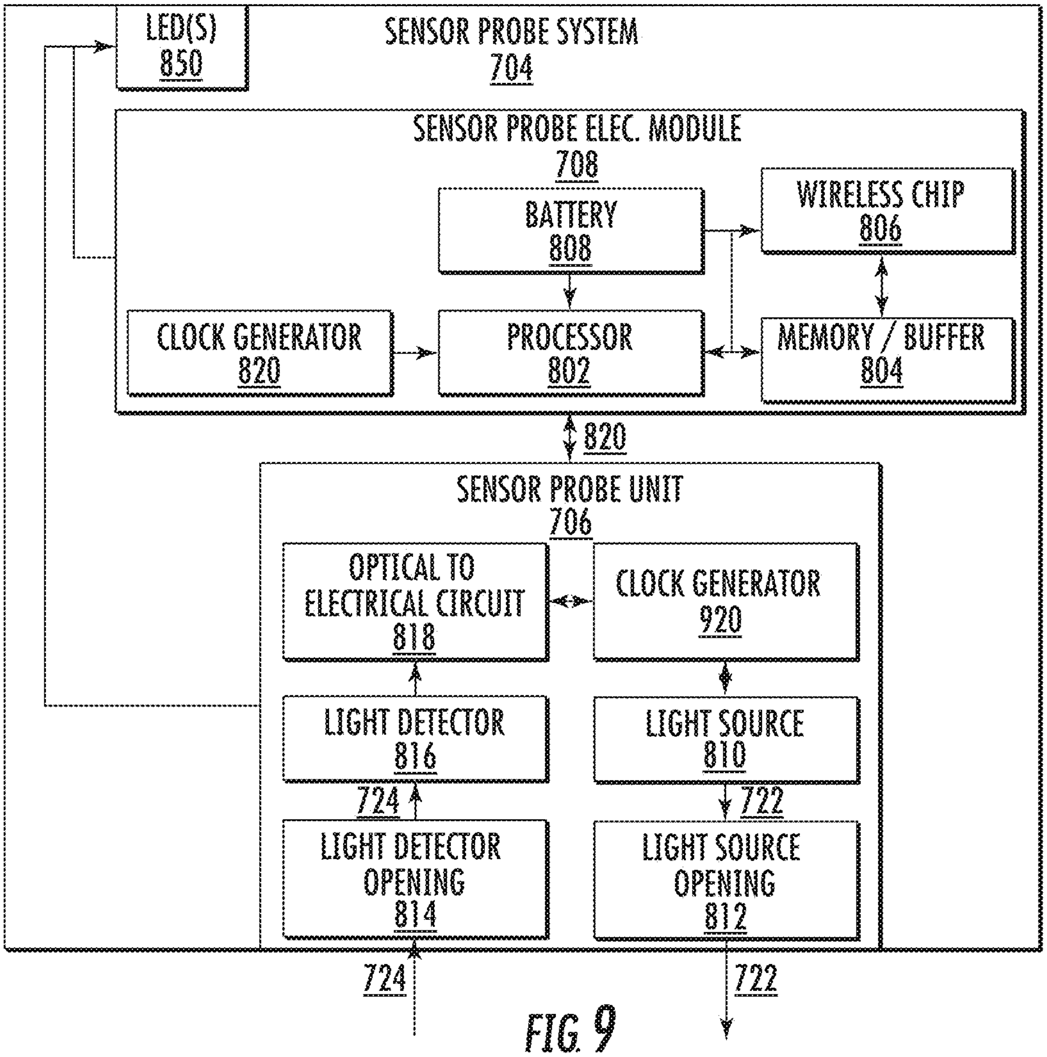
FIG. 9 shows another simplified schematic diagram of an example sensor probe system, according to some embodiments.

FIG. 9 shows another simplified schematic diagram of an example sensor probe system, according to some embodiments. In these embodiments shown in FIG. 9, various components shown therein perform identical or substantially similar functions as those described above with reference to FIG. 8. The example sensor probe system implementation 704 shown in FIG. 9 similarly comprises a sensor probe electronic module 708 and a sensor probe 706 that is connected to the sensor probe electronic module 708 via one or more electrical cables or wires 820 that transmit the control signals (not shown) from, for example, the controller, processor, processor core, or thread of execution 802 in the sensor probe electronic module 708 to the sensor probe unit 706. In some embodiments, the sensor probe electronic module 708 may include one or more LEDs (LEDs) 850 which may be separately powered to indicate, for example, the respective operational states of the sensor probe system 704, a portion thereof (e.g., the sensor probe electronic module 708), or one or more components thereof (e.g., the light source(s) 810, the detector(s) 816, wireless IC 806, and others) For example, these one or more LEDs may indicate whether a specific component or a module is powered on, connection status or signal strength, or both, operation state, battery state, and others.

The sensor probe electronic module 708 may comprise, for example yet without limitation, a memory (e.g., SRAM, DRAM, Flash, or others) or buffer 804, a controller, processor, processor core, or thread of execution 802 operatively coupled to the memory or buffer 804, and a clock generator 820 operatively coupled to the processor, processor core, or thread 802. The sensor probe electronic module 708 may also comprise a wireless integrated circuit 806 that is operatively coupled directly or indirectly to the memory or buffer 804 and the processor, processor core, or thread 802 to transmit and receive data in the form of data packets. The sensor probe electronic module 708 may be powered by a battery 808 that may comprise a one-time use or rechargeable battery to power the sensor probe electronic module 708. In some embodiments, the sensor probe unit 706 may also be powered by the battery 808 in the sensor probe electronic module 708.

The sensor probe unit 706 may comprise one or more light sources 810 and one or more light detectors 816 that may be respectively coupled to one or more light source openings 812 and one or more light detector openings 814 to transmit one or more incident light beams or signals 722 into and to receive one or more reflected or refracted light signals 724 from a biological tissue. The sensor probe unit 706 may optionally comprise another clock generator 920 that may be separate and distinct from the clock generator 820 in the sensor probe electronic module 708 in some embodiments. In these embodiments, the sensor probe electronic module 708 and the sensor probe unit 706 represent two independent state machines with their respective, individual clocks generated by corresponding clock generators (e.g., 820 for the sensor probe electronic module and 920 for the sensor probe unit 706). In some other embodiments, a master clock controls the synchronization of operations of the sensor probe electronic module 708 and the sensor probe unit 706 although it shall be noted that having the master clock in the sensor probe electronic module 708 and sending the clock signals therefrom to the sensor probe unit 706 may introduce skews and thus parasitics.

The collected, reflected, or refracted light signals 724 are in an analog form and may be converted to electrical signals by an optical to electrical circuit 818. In some embodiments, the optical to electrical circuit 818 may include an analog front end (AFE) which is a circuit that conditions analog signals and interfaces such analog signals with other systems and may include, for example but not limited to, one or more analog amplifiers, one or more filters, and/or application-specific integrated circuit (ASICs). In some of these embodiments, the optical to electrical circuit 818 (e.g., an AFE) translates or converts analog signals from the sensor probe unit 706 for processing or transmission, or both. In addition, an AFE may filter out unwanted or undesired noise with a programmable bandwidth to leave only the desired signal(s). In some embodiments, the optical to electrical circuit 818 may support a first number of light sources 810 (e.g., M light sources) and a second number of detectors 816 (e.g., N detectors) to support up to M×N signal phases where the optical to electrical circuit 818 may acquire the signals from each phase in a synchronized manner and stored in a buffer (e.g., a first-in, first-out buffer) that may be read out by using, for example, an serial peripheral interface (SPI) or an inter-integrated circuit (I^2C) interface. In some embodiments, the aforementioned optical to electrical circuit 818 may be located in the sensor probe unit 706 or in the sensor probe electronic module 708 in some other embodiments. In some embodiments, the optical to electrical circuit 818 may include the driver and a programmable current (e.g., a multibit programmable light source current) with an adjustable or programmable range (e.g., from 10 milliamps to 500 milliamps). In some of these embodiments, the optical to electrical circuit 818 may include multiple modes of operation. For example, the optical to electrical circuit 818 may provide a first mode to fire multiple light sources 810 in parallel, a second mode to fire one or more light sources 810 on-time or at a specific time point, a third model to simultaneously support all of the multiple light sources 810 for improved or optimized StO2 measurement, heart rate monitoring, or multiple wavelength heart rate monitoring, and others.

Figure 10:
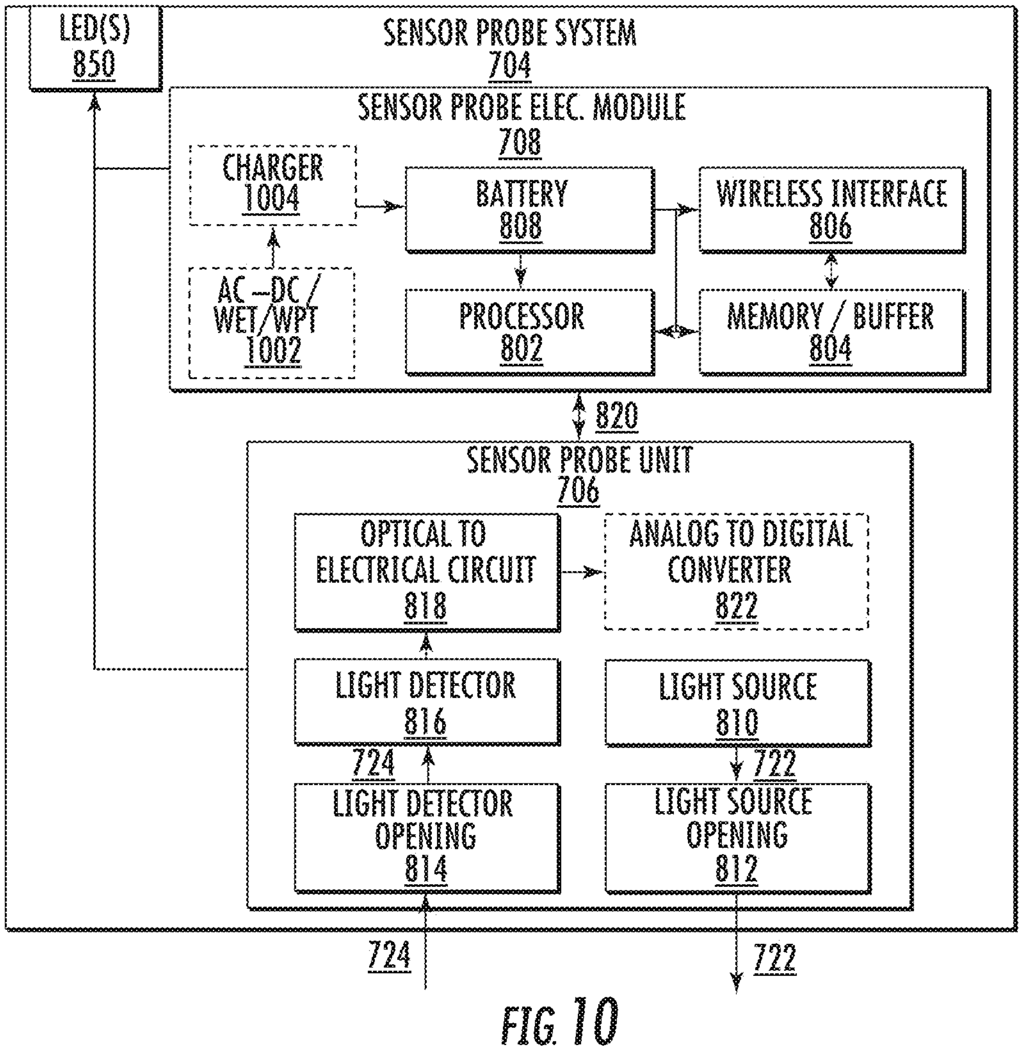
FIG. 10 shows another simplified schematic diagram of an example sensor probe system, according to some embodiments.

FIG. 10 shows another simplified schematic diagram of an example sensor probe system, according to some embodiments. In these embodiments shown in FIG. 10, various components shown therein perform identical or substantially similar functions as those described above with reference to FIG. 8 or FIG. 9. The example sensor probe system implementation 704 shown in FIG. 10 similarly comprises a sensor probe electronic module 708 and a sensor probe 706 that is connected to the sensor probe electronic module 708 via one or more electrical cables or wires 820 that transmit the control signals (not shown) from, for example, the processor, processor core, or thread of execution 802 in the sensor probe electronic module 708 to the sensor probe unit 706. In some embodiments, the sensor probe electronic module 708 may include one or more LEDs 850 which may be separately powered to indicate, for example, the respective operational states of the sensor probe system 704, a portion thereof (e.g., the sensor probe electronic module 708), or one or more components thereof (e.g., the light sources 810, the detectors 816, wireless circuit 806, and others) For example, these one or more LEDs may indicate whether a specific component or a module is powered on, connection status or signal strength, operation state, state of the battery 808, state of the charger 1004, and others.

The sensor probe electronic module 708 may comprise, for example yet without limitation, a memory (e.g., SRAM, DRAM, Flash, cache, or others) or buffer 804, a processor, processor core, or thread of execution 802 operatively coupled to the memory or buffer 804, and a clock generator 820 operatively coupled to the processor, processor core, or thread 802. The sensor probe electronic module 708 may also comprise a wireless integrated circuit 806 that is operatively coupled directly or indirectly to the memory or buffer 804 and the processor, processor core, or thread 802 to transmit and receive data in the form of data packets. The sensor probe electronic module 708 may be powered by a battery 808 that may comprise a one-time use battery or rechargeable battery to power the sensor probe electronic module 708. The battery 808 may be charged via a charger 1004 that may be operatively coupled to a wired AC-to-DC circuit, a wireless energy transfer (WET) circuit, or a wireless power transfer (WPT) circuit 1002. Either or both the charger 1004 and the AC-to-DC circuit, the WET circuit or the WPT circuit may be optional in the sensor probe electronic circuit 708.

The sensor probe unit 706 may comprise one or more light sources 810 and one or more light detectors 816 that may be respectively coupled to one or more light source openings 812 and one or more light detector openings 814 to transmit one or more incident light beams or signals 722 into and to receive one or more reflected or refracted light signals 724 from a biological tissue. The sensor probe unit 706 may optionally comprise another clock generator 920 that may be separate and distinct from the clock generator 820 in the sensor probe electronic module 708 in some embodiments. In these embodiments, the sensor probe electronic module 708 and the sensor probe unit 706 represent two independent state machines with their respective, individual clocks generated by corresponding clock generators (e.g., 820 for the sensor probe electronic module and 920 for the sensor probe unit 706 as shown in FIG. 9). In some other embodiments, a master clock controls the synchronization of operations of the sensor probe electronic module 708 and the sensor probe unit 706 although it shall be noted that having the master clock in the sensor probe electronic module 708 and sending the clock signals therefrom to the sensor probe unit 706 may introduce skews and thus parasitics.

The collected, reflected, or refracted light signals 724 are in an analog form and may be converted to electrical signals by an optical to electrical circuit 818. In some embodiments, the aforementioned optical to electrical circuit 818 may be located in the sensor probe unit 706 or in the sensor probe electronic module 708 in some other embodiments. The electrical signals may be of an analog form and may be further optionally converted via an analog-to-digital conversion circuit (e.g., a packetizer for packetization, a quantizer, a modulator, an encoder, and others) 822 into a digital form within the sensor probe unit 706 before being transmitted back to the sensor probe electronic module 708 via connection 820.

Figure 11:
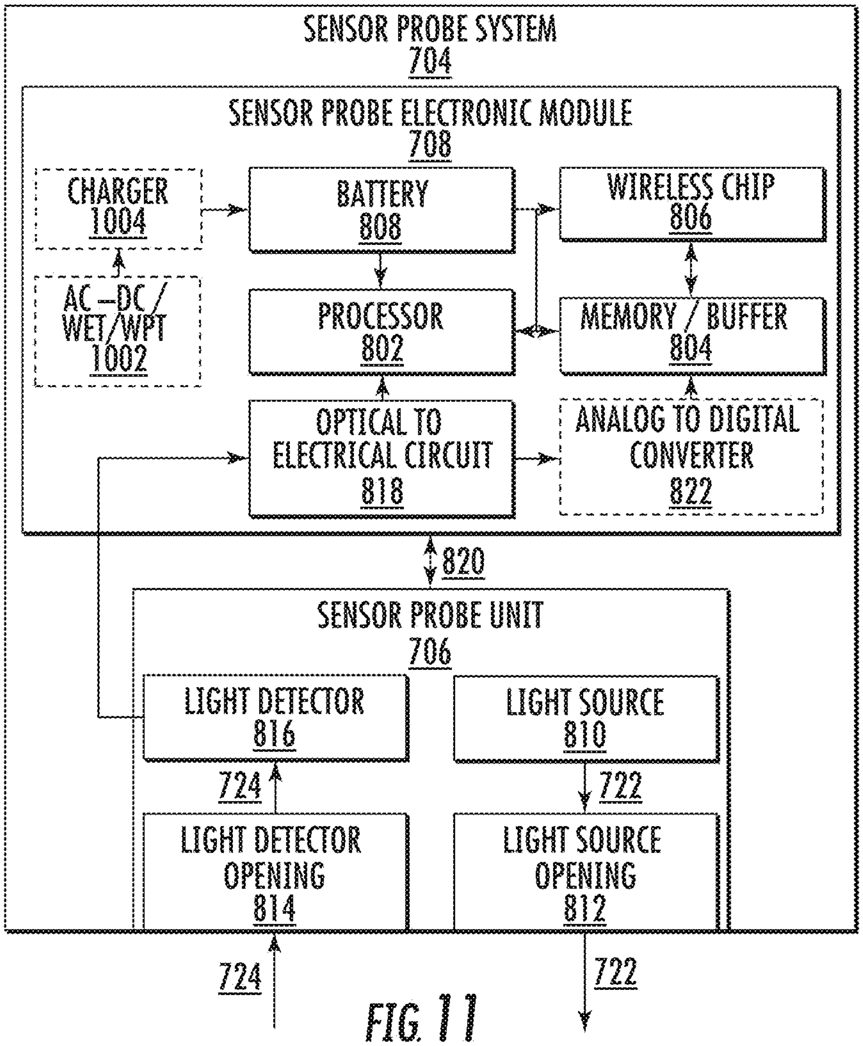
FIG. 11 shows another simplified schematic diagram of an example sensor probe system, according to some embodiments.

FIG. 11 shows another simplified schematic diagram of an example sensor probe system, according to some embodiments. In these embodiments shown in FIG. 11, various components shown therein perform identical or substantially similar functions as those described above with reference to FIG. 8, 9, or 10. The example sensor probe system implementation 704 shown in FIG. 11 similarly comprises a sensor probe electronic module 708 and a sensor probe 706 that is connected to the sensor probe electronic module 708 via one or more electrical cables or wires 820 that transmit the control signals (not shown) from, for example, the processor, processor core, or thread of execution 802 in the sensor probe electronic module 708 to the sensor probe unit 706.

The sensor probe electronic module 708 may comprise, for example yet without limitation, a memory (e.g., SRAM, DRAM, Flash, cache, or others) or buffer 804, a processor, processor core, or thread of execution 802 operatively coupled to the memory or buffer 804, and a clock generator 820 operatively coupled to the processor, processor core, or thread 802. The sensor probe electronic module 708 may also comprise a wireless integrated circuit 806 that is operatively coupled directly or indirectly to the memory or buffer 804 and the processor, processor core, or thread 802 to transmit and receive data in the form of data packets. The sensor probe electronic module 708 may be powered by a battery 808 that may comprise a one-time use or rechargeable battery to power the sensor probe electronic module 708. The rechargeable battery may be charged via a charger 1004 that may be operatively coupled to a wired AC-to-DC circuit, a wireless energy transfer (WET) circuit, or a wireless power transfer (WPT) circuit 1002. Either or both the charger 1004 and the AC-to-DC circuit, the WET circuit or the WPT circuit may be optional in the sensor probe electronic circuit 708.

The sensor probe unit 706 may comprise one or more light sources 810 and one or more light detectors 816 that may be respectively coupled to one or more light source openings 812 and one or more light detector openings 814 to transmit one or more incident light beams or signals 722 into and to receive one or more reflected or refracted light signals 724 from a biological tissue. The sensor probe unit 706 may optionally comprise another clock generator 920 that may be separate and distinct from the clock generator 820 in the sensor probe electronic module 708 in some embodiments. In these embodiments, the sensor probe electronic module 708 and the sensor probe unit 706 represent two independent state machines with their respective, individual clocks generated by corresponding clock generators (e.g., 820 for the sensor probe electronic module and 920 for the sensor probe unit 706 as shown in FIG. 9). In some other embodiments, a master clock controls the synchronization of operations of the sensor probe electronic module 708 and the sensor probe unit 706 although it shall be noted that having the master clock in the sensor probe electronic module 708 and sending the clock signals therefrom to the sensor probe unit 706 may introduce skews and thus parasitics.

The collected, reflected, or refracted light signals 724 are in an analog form and may be converted to electrical signals by an optical to electrical circuit 818. In some embodiments, the aforementioned optical to electrical circuit 818 may be located in the sensor probe electronic module 708. The electrical signals may be of an analog form and may be further optionally converted via an analog-to-digital conversion circuit (e.g., a packetizer for packetization, a quantizer, a modulator, an encoder, and others) 822 into a digital form within the sensor probe electronic module 708. In some embodiments, the sensor probe electronic module 708 may optionally comprise the aforementioned sensor probe electronic module 708.

Figure 12:
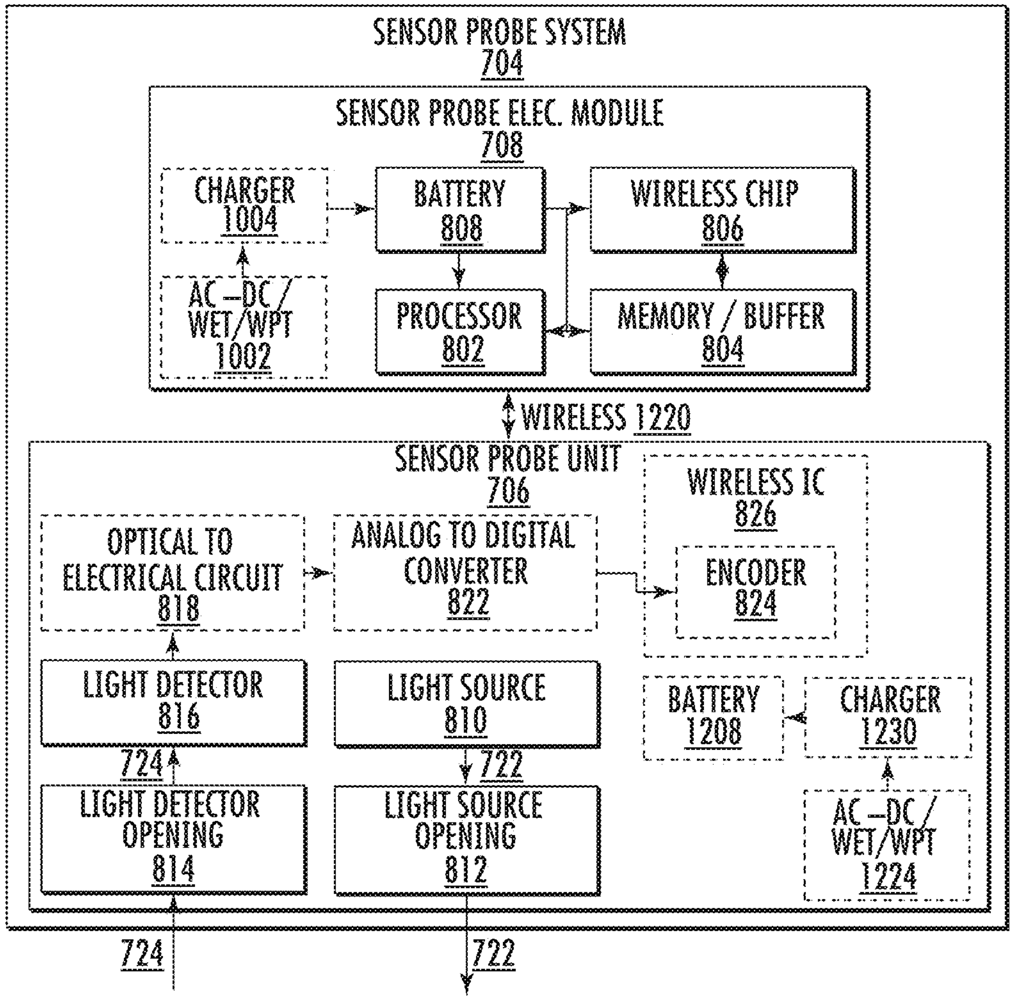
FIG. 12 shows a simplified schematic diagram of an example sensor probe system wirelessly connected to an example sensor probe unit, according to some embodiments.

FIG. 12 shows a simplified schematic diagram of an example sensor probe system wirelessly connected to an example sensor probe unit, according to some embodiments. In these embodiments shown in FIG. 12, various components shown therein perform identical or substantially similar functions as those described above with reference to FIG. 8, 9, 10, or 11. The example sensor probe system implementation 704 shown in FIG. 12 similarly comprises a sensor probe electronic module 708 and a sensor probe unit 706 that is connected to the sensor probe electronic module 708 via a wireless connection 1220 that transmit the control signals (not shown) from, for example, the processor, processor core, or thread of execution 802 in the sensor probe electronic module 708 to the sensor probe unit 706 and the collected, reflected or refracted light signals or a different form thereof (e.g., an electrical signal, a digital signal, and others).

The sensor probe electronic module 708 may comprise, for example yet without limitation, a memory (e.g., SRAM, DRAM, Flash, cache, or others) or buffer 804, a processor, processor core, or thread of execution 802 operatively coupled to the memory or buffer 804, and a clock generator (not shown) operatively coupled to the processor, processor core, or thread 802. The sensor probe electronic module 708 may also comprise a wireless integrated circuit 806 that is operatively coupled directly or indirectly to the memory or buffer 804 and the processor, processor core, or thread 802 to transmit and receive data in the form of data packets. The sensor probe electronic module 708 may be powered by a battery 808 that may comprise a one-time use (e.g., disposable or not rechargeable) or rechargeable battery to power the sensor probe electronic module 708. The rechargeable battery may be charged via a charger 1004 that may be operatively coupled to a wired AC-to-DC circuit, a wireless energy transfer (WET) circuit, or a wireless power transfer (WPT) circuit 1002. Either or both the charger 1004 and the AC-to-DC circuit, the WET circuit or the WPT circuit may be optional in the sensor probe electronic circuit 708. In various embodiments, a rechargeable battery may be physically removed from the sensor probe electronic module 708 and placed in an external charger for recharge.

The sensor probe unit 706 may comprise one or more light sources 810 and one or more light detectors 816 that may be respectively coupled to one or more light source openings 812 and one or more light detector openings 814 to transmit one or more incident light beams or signals 722 into and to receive one or more reflected or refracted light signals 724 from a biological tissue. The sensor probe unit 706 may optionally comprise another clock generator (not shown) that may be separate and distinct from the clock generator (also not shown) in the sensor probe electronic module 708 in some embodiments.

In some of these embodiments, the sensor probe unit 706 may comprise a wireless integrated circuit 826 that wirelessly transmits and receives data in the form of packets between the sensor probe unit 706 and the sensor probe electronic module 708. The wireless integrated circuit 826 may comprise an encoder 824 (or modulator, packetizer, quantizer, and others) that encode incoming signals into packets for transmission in some embodiments. For example, the reflected or refracted light signals 724 collected at the one or more light detectors 816 may be first converted into an electrical form by an optical to electrical circuit 818. An analog-to-digital conversion circuit 822 may further convert the electrical signals into digital form that may be forwarded to the wireless integrated circuit 826 for transmission to the sensor probe electronic module 708 in some embodiments.

In some embodiments, the sensor probe unit 706 may be optionally powered individually by a battery 1208. In some embodiments, the battery 1208 may comprise a rechargeable battery that may be charged by a charger 1230 that may be operatively coupled to an AC-to-DC conversion circuit, a WET module, or a WPT module 1224 where either or both the charger 1230 and the AC-DC conversion circuit, the WET module, or the WPT module 1224 may be physically located within or external to the sensor probe unit 706.

In these embodiments, the sensor probe electronic module 708 and the sensor probe unit 706 represent two independent state machines with their respective, individual clocks generated by corresponding clock generators. In some other embodiments, a master clock controls the synchronization of operations of the sensor probe electronic module 708 and the sensor probe unit 706 although it shall be noted that having the master clock in the sensor probe electronic module 708 and sending the clock signals therefrom to the sensor probe unit 706 may introduce skews and thus parasitics.

The collected, reflected, or refracted light signals 724 are in an analog form and may be converted to electrical signals by an optical to electrical circuit 818. In some embodiments, the aforementioned optical to electrical circuit 818 may be located in the sensor probe electronic module 708. The electrical signals may be of an analog form and may be further optionally converted via an analog-to-digital conversion circuit (ADC) (e.g., a packetizer for packetization, a quantizer, a modulator, an encoder, and others) 822 into a digital form within the sensor probe electronic module 708. In some embodiments, the sensor probe electronic module 708 may optionally comprise the aforementioned sensor probe electronic module 708.

Figure 13:
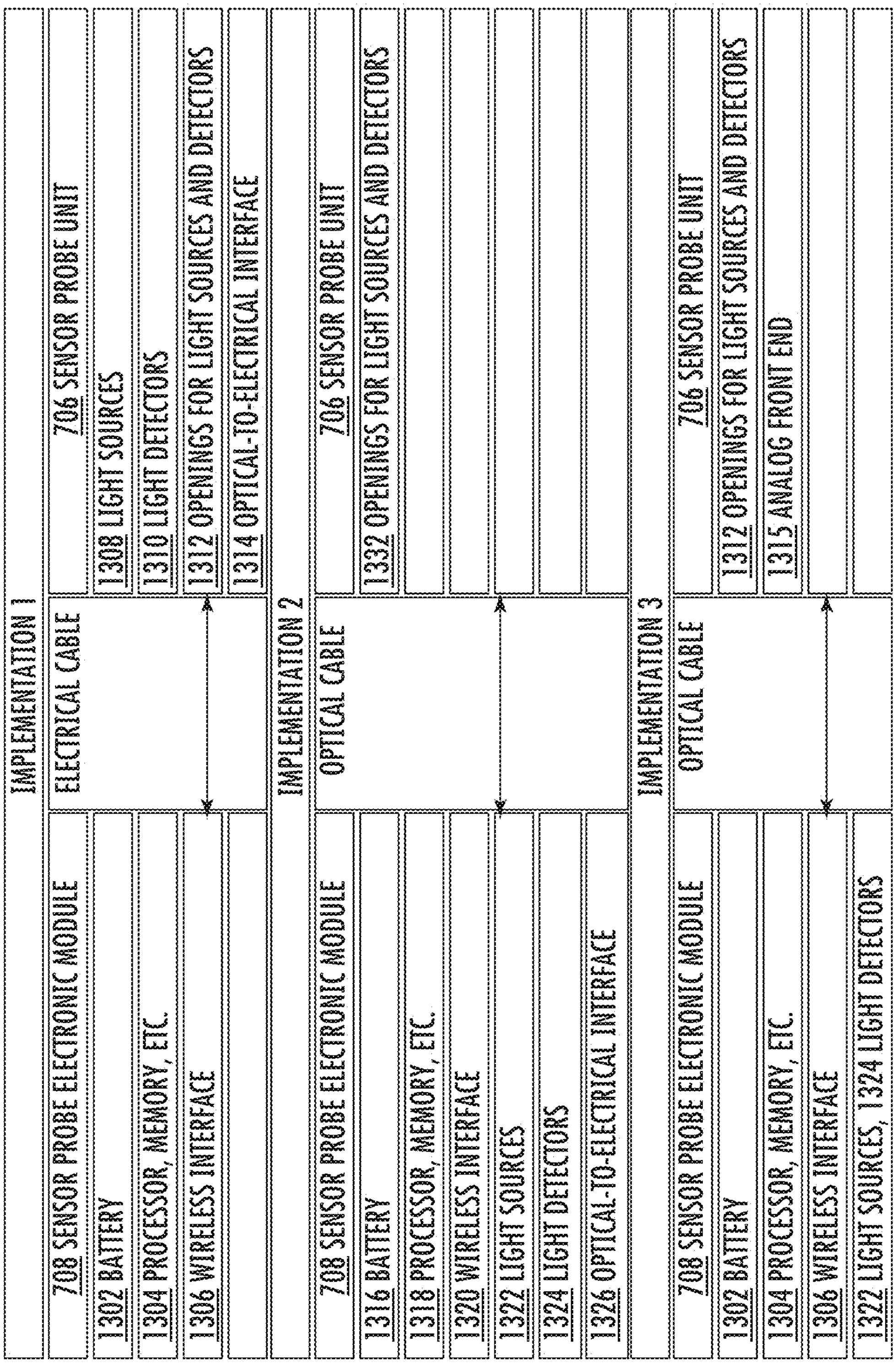
FIG. 13 shows some example implementations of a medical device console wirelessly connected to a sensor probe electronic module, according to some embodiments.

FIG. 13 shows some example implementations of a sensor probe unit connected to a sensor probe electronic module, according to some embodiments. In some of these embodiments, a sensor probe electronic module 708 may be connected to a sensor probe unit 706 via one or more electrical cables transmitting digital or analog electrical signals. In these embodiments, the sensor probe electronic module 708 may comprise, for example without limitation, a battery 1302, a processor, memory, computer bus, and others 1304, and a wireless integrated circuit or interface 1306.

Moreover, the aforementioned sensor probe unit 706 may comprise, for example without limitation, one or more light sources 1308 for emitting light beams, signals, or pulses with a plurality of different wavelengths, one or more light detectors 1310 for detecting reflected or refracted light signals from within or from the exterior surfaces the biological tissue, one or more incident light openings for the one or more light sources and one or more reflected or refracted light openings for the one or more light detectors 1312, and an optical-to-electrical interface or conversion circuitry 1314 for converting the reflected or refracted light signals detected at the one or more detectors into electrical signals (e.g., a current waveform, a voltage waveform, and others).

In some embodiments shown as "implementation 2," a sensor probe electronic module 708 may be connected to a sensor probe unit 706 via one or more electrical cables transmitting digital and/or analog electrical signals. In these embodiments, the sensor probe electronic module 708 may comprise, for example without limitation, a battery 1316, a processor, memory, computer bus, and others 1318, and a wireless integrated circuit or interface 1320, one or more light sources 1322 for emitting light beams, signals, or pulses with a plurality of different wavelengths, one or more light detectors 1324 for detecting reflected or refracted light signals from within or from the exterior surfaces the biological tissue, and an optical-to-electrical interface or conversion circuitry 1326 for converting the reflected or refracted light signals detected at the one or more detectors into electrical signals (e.g., a current waveform, a voltage waveform, and others).

Moreover, the aforementioned sensor probe unit 706 may comprise, for example without limitation, one or more incident light openings for the one or more light sources and one or more reflected or refracted light openings for the one or more light detectors 1332.

In some embodiments shown as "implementation 3," a sensor probe electronic module 708 may be connected to a sensor probe unit 706 via one or more electrical cables transmitting digital or analog electrical signals. In these embodiments, the sensor probe electronic module 708 may comprise, for example without limitation, a battery 1302, a processor (or controller), memory, computer bus, and others 1304, and a wireless integrated circuit or interface 1306. Moreover, the aforementioned sensor probe unit 706 may comprise, for example but not limited to, one or more incident light openings for the one or more light sources and one or more reflected or refracted light openings for the one or more light detectors 1312, and an analog front end 1315 for converting or otherwise processing the reflected or refracted light signals detected at the one or more detectors into electrical signals (e.g., a current waveform, a voltage waveform, and others). The one or more light sources 1322 for emitting light beams, signals, or pulses with a plurality of different wavelengths and the one or more light detectors 1324 for detecting reflected or refracted light signals from within or from the exterior surfaces the biological tissue may be implemented within the sensor probe unit 706 in some embodiments or within the sensor probe electronic module 708 in some other embodiments. In the former embodiments, the analog front end 1315 may convert optical signals into electrical or digital signals and can filter out undesired or unwanted signals (e.g., noise). In the latter embodiments where the light sources 1322 and the light detectors 1324 are implemented within the sensor probe electronic module 708, the analog front end 1315 may process the received signals (e.g., by filtering out undesired or unwanted signals from the received signals). In some embodiments, signal conversion tasks (e.g., analog to electrical, digital or electrical, or digital to analog) and signal processing tasks such as signal filtering tasks may be distributed between the processor and the analog front end 1315 (or the optical-to-electrical interface 1314 in "implementation 1" and "implementation 2").

In some embodiments, an analog front end (AFE) includes a circuit that conditions analog signals and interfaces such analog signals with other systems and may include, for example but not limited to, one or more analog amplifiers, one or more filters, or application-specific integrated circuit (ASICs), or a combination. In some of these embodiments, the AFE 1315 translates, converts, or otherwise processes analog signals from the one or more light detectors 1310 in the sensor probe unit 706 for processing and/or transmission. In addition, an AFE may filter out unwanted or undesired noise with a programmable bandwidth to leave only the desired signal or signals. In some embodiments, the AFE 1315 may support a first number of light sources 1308 (e.g., M light sources) and a second number of detectors 1310 (e.g., N detectors) to support up to M×N signal phases where the AFE 1315 may acquire the signals from each phase in a synchronized manner and stored in a buffer (e.g., a first-in, first-out buffer (FIFO)) that may be read out by using, for example, an serial peripheral interface (SPI) or an inter-integrated circuit (I^2C) interface. In some embodiments, the aforementioned AFE 1315 may be located in the sensor probe unit 706 or in the sensor probe electronic module 708 in some other embodiments. In some embodiments, the AFE 1315 may include the driver and a programmable current (e.g., a multibit programmable light source current) with an adjustable or programmable range (e.g., from 10 milliamps to 500 milliamps). In some of these embodiments, the AFE 1315 may include multiple modes of operation. For example, the AFE 1315 may provide a first mode to fire multiple light sources 810 in parallel, a second mode to fire one or more light sources 1308 on-time or at a specific time point, a third model to simultaneously support all of the multiple light sources 1308 for improved or optimized StO2 measurement.

Figure 14:
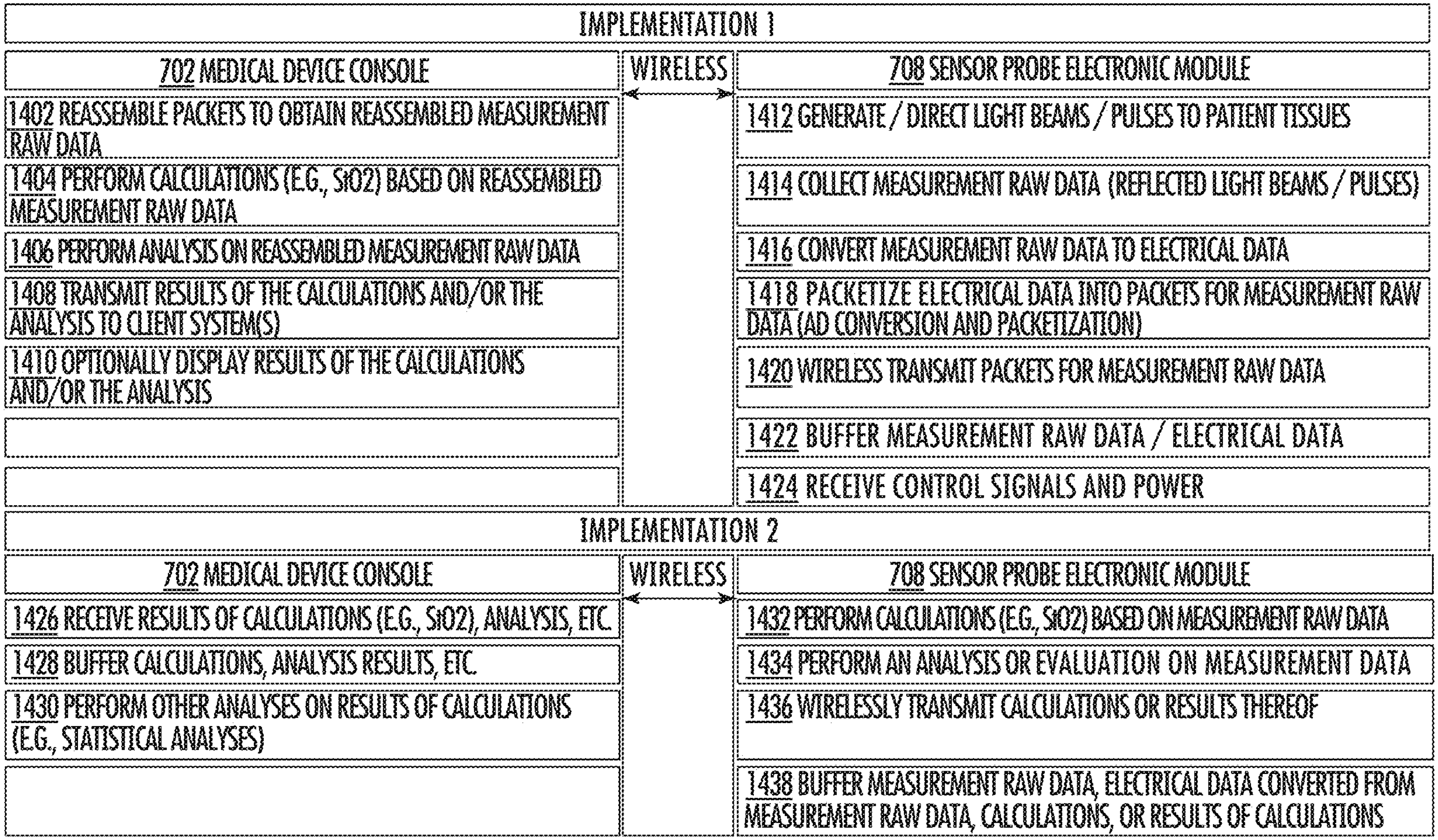
FIG. 14 shows some example implementations of a sensor probe unit connected to a sensor probe electronic module, according to some embodiments.

FIG. 14 shows some example implementations of a medical device console wirelessly connected to a sensor probe electronic module, according to some embodiments. In some of these embodiments, each medical device console 702 is wirelessly connected to a corresponding sensor probe electronic module 708 to have a one-to-one correspondence. In some other embodiments, a plurality of medical device consoles 702 may be wirelessly connected to a single sensor probe electronic module 708. Yet in some embodiments, a single medical device console 702 may be wirelessly connected to a plurality of sensor probe electronic module 708. As described above with reference to FIGS. 7A-7L, a sensor probe system in some embodiments may be self-contained so that the medical device system 102 may include only the sensor probe system (e.g., 704) without the medical device console 702. In these embodiments, the sensor probe electronic module 708 in FIG. 14 may be wirelessly connected to an external system or an external network (e.g., 104 in FIG. 7A), rather than to a medical device console 702 as shown in FIG. 14.

In some embodiments, the sensor probe electronic module 708 may also optionally buffer the measurement raw data or the converted electrical data at 1422. In order to collect the measurement raw data, the sensor probe electronic module 708 may receive a control signal at 1424 for the one or more light sources in the sensor probe electronic module 708 so that these one or more light sources emit one or more light beams, signals, or pulses some of which may be absorbed into the biological tissue of interest and scatter within or from the exterior surfaces the biological tissue so that one or more detectors may detect and collect the scattered, reflected or refracted light signals as measurement raw data.

The sensor probe electronic module 708 may generate or direct light beams, signals, or pulses to a biological tissue (e.g., a patient's tissue) at 1412 and collect or gather measurement raw data (e.g., reflected or refracted light signals, pulses, and others) at 1414. The collected measurement raw data is in the form of analog signals and may thus be converted into electrical data (e.g., voltage waveforms, and others) at 1416, and the electrical data may be packetized (or quantized, encoded, modulated, and others) at 1418 into a sequence of packets for transmission over a network by partitioning the measurement raw data into a sequence of payloads and further by encoding each packet with a unit of data representing a payload in the sequence. At 1420, this sequence of packets may be transmitted to the medical device console 702 which may then perform packet reconstruction to obtain the payload representing the measurement raw data.

In some embodiments, a medical device console 702 may include a process (e.g., a central processing unit (CPU), a network processor, a specific processor, or a general-purpose processor, and others) that executes a sequence of instructions to perform a set of acts. For example, after receiving incoming packets having payloads representing measurement raw data from the sensor probe electronic module 708, the medical device console 702 may be configured to reassemble packets to obtain reassembled measurement raw data at 1402. With the reassembled measurement data, the medical device console 702 may further execute instructions to analyze the reassembled measurement data at 1404. For example, the medical device console may perform one or more calculations (e.g., tissue oxygen saturation StO2) based at least in part upon the reassembled measurement data.

In addition, the medical device console 702 may perform an analysis on the measurement raw data at 1406 and transmit the results of the calculations from 1404 and/or the analysis from 1406 to one or more client systems (e.g., client system 108 in FIG. 1) at 1408, and the results of the calculations and/or the analysis may be optionally displayed at 1410 on a display device. For example, the medical device console 702 may analyze the reassembled raw measurement data to determine the effects of a temporary induced ischemia on intestinal or mesentery tissue oxygen saturation can be analyzed to determine whether the patient of interest is suffering from intestinal ischemia. A temporary ischemic period can be induced on an intestinal or mesentery tissue by using a device that constricts a mesenteric artery. Since the tissue continues to consume remaining oxygen from blood (with no or little influx of fresh arterial blood), tissue oxygen saturation will decline gradually during the temporary ischemic period. If the tissue is healthy and normal, then stopping or reducing the blood flow to the tissue will result in a significant reduction of measured oxygen saturation over time. If the intestinal or mesentery tissue already suffers from ischemia (e.g., due to clogged mesenteric arteries or infarct intestinal tissue), then stopping or reducing the arterial blood flow will not significantly reduce measured oxygen saturation of the tissue.

In one embodiment, the analysis at 1406 may include calculating a rate of change of oxygen saturation over a period of time. For example, a mesenteric artery supplying blood to the tissue can be clipped, and oxygen saturation of the tissue can be measured every 10 seconds, 30 seconds, one minute, two minutes, or other suitable time intervals. The blood supply to the tissue can be clipped for any suitable time period, as long as it does not negatively impact the patient's long-term health. For example, the blood supply may be clipped for a period anywhere between 1 minute, 2 minutes, 5 minutes, 10 minutes, 20 minutes, 30 minutes, or any other suitable time period. The measured oxygen saturation (e.g., in terms of percent) can be plotted against time. The rate of change may be calculated using any suitable method. For example, the rate of change can be measured and calculated around a midpoint of the induced ischemic period.

The rate of oxygen saturation change may be calculated, and compared to a threshold to determine whether the patient is suffering from intestinal or mesentery ischemia. A threshold can be set differently depending on various factors (e.g., the patient's age, health history, gender, and others). A threshold can be set at any suitable rate, e.g., at about 3, 5, 10, 20, 30, 40, 50, 60, 70, 80, 90, or 100 percent per minute. For example, if the threshold is set at a rate of 20 percent oxygen saturation change per minute and if the patient's rate of change is calculated to be about 5 percent oxygen saturation change per minute, then the patient is diagnosed as having intestinal ischemia or a hypoxia condition.

For example, the medical device console 702 may analyze the reassembled measurement raw data to determine changes in oxygen saturation of the biological tissue after an ischemia is induced in the intestinal or mesentery tissue by reducing or stopping the blood flow. The medical device console 702 may analyze changes in tissue oxygen saturation during the induced ischemic period at 1406 based at least in part upon a threshold. If the medical device console 702 determines that the changes do not meet the threshold, the medical device console 702 may preliminarily conclude that the patient may be diagnosed as suffering from intestinal ischemia and generate a visual alert, an audible alert, or a visible and audible alert.

In another embodiment, the analysis at 1406 may include determining either an absolute change or relative change in oxygen saturation level of the intestinal or mesentery tissue. Any suitable time point can be selected for measuring oxygen saturation level. For example, oxygen saturation can be measured before clipping the blood supply. After the blood supply to the intestinal or mesentery tissue is clipped, oxygen saturation can be measured at a selected time point (e.g., 5 minutes, 10 minutes, 20 minutes, 30 minutes, and others). Then the change in oxygen saturation level of the tissue can be recorded.

For example, at time zero (before clipping the mesenteric artery), the oxygen saturation value of a tissue is measured at 80 percent. At 10-minute time point after the mesenteric artery is clipped, the oxygen saturation of the same tissue is measured at 20 percent. Then the absolute change of oxygen saturation value may be recorded as being 60 percent. Alternatively, the relative change of oxygen saturation value may be recorded as being 75 percent (e.g., (80–20)/80). A healthy intestinal or mesentery tissue will have a higher absolute or relative change in oxygen saturation value (e.g., above 40 percent), whereas an intestinal or mesentery tissue that already suffers from ischemia will have a lower absolute or relative change in oxygen saturation value (e.g., below 40 percent).

The change in oxygen saturation level at a specific time point can be compared to a threshold. For example, ten minutes into the induced ischemic period can be selected as a time point to calculate the absolute change in oxygen saturation level of the intestinal or mesentery tissue, and a threshold may be selected at 40 percent. If a patient's oxygen saturation level changed less than 40 percent at ten-minute time point during the induced ischemic period, then the patient can be diagnosed as suffering from intestinal ischemia or a hypoxia condition. If the patient's oxygen saturation level changed more than 40 percent at the ten-minute time point during the induced ischemic period, then the patient can be diagnosed as being normal and healthy.

Figure 31:
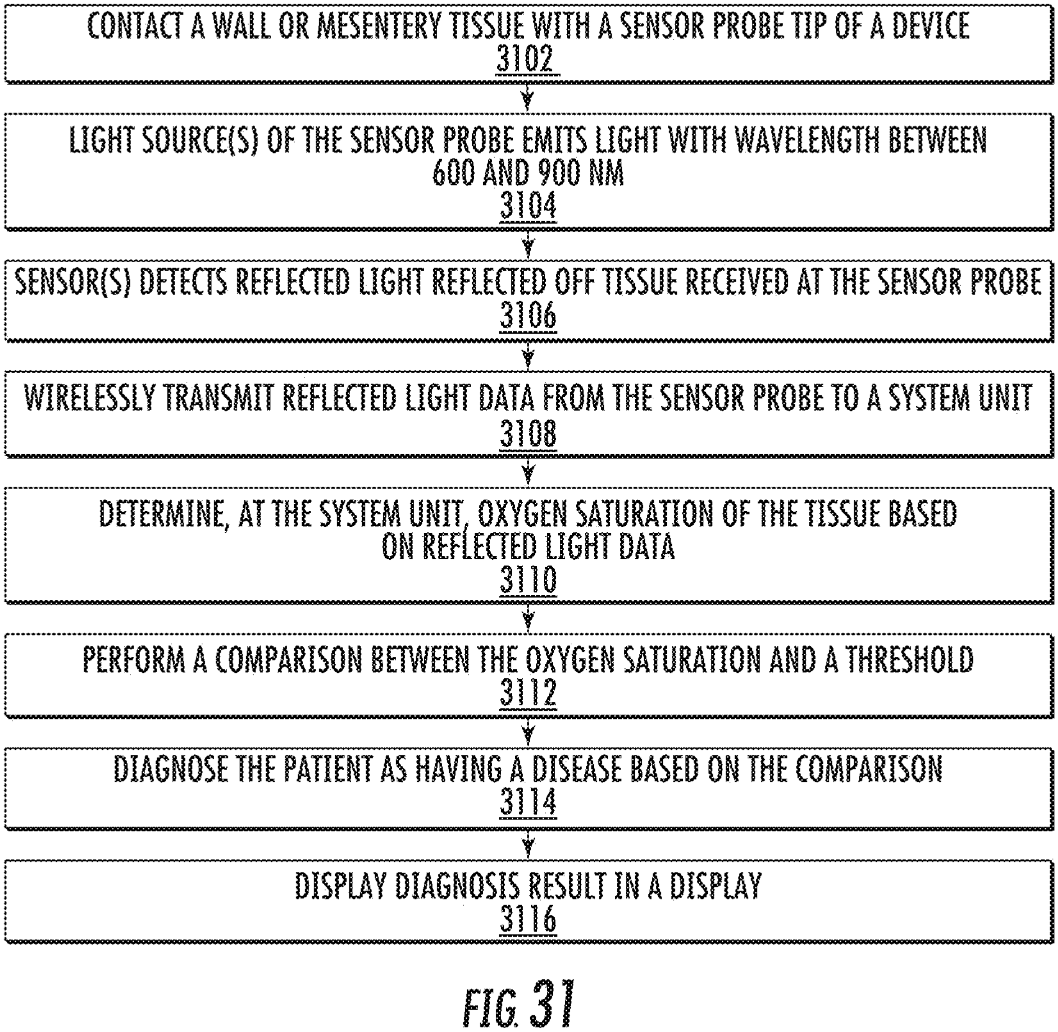
FIG. 31 shows a more detailed block diagram for diagnosing a patient based at least in part upon monitored viability of a biological tissue, according to some embodiments.

In addition to using the process shown in FIG. 31 as a diagnostic tool for intestinal ischemia, these actions shown in FIG. 31 may be repeated and applied to determine which portion of the intestine or mesentery is causing intestinal ischemia. Different mesenteric arteries may be pressed down or clipped, and different portions of the intestine or mesentery may be tested for their oxygen saturation level. The results of oxygen saturation change at different portions of the intestine can be used for resection or anastomosis procedures.

In some embodiments shown as "implementation 2", the sensor probe electronic module 708 may perform calculations (e.g., StO2) at 1432 based at least in part upon the measurement raw data collected by one or more detectors in response to the light beams, signals, or pulses emitted by one or more light sources. The sensor probe electronic module 708 may also perform an analysis or evaluation on the measurement raw data at 1434. For example, the sensor probe electronic module 708 may perform one or more of the aforementioned analyses performed by the medical device console 702 at 1406 in these embodiments. That is, the sensor probe electronic module 708, rather than the medical device console 702, may comprise compute power to analyze the collected measurement raw data to obtain the desired or requisite analysis results at 1434.

The sensor probe electronic module 708 may wirelessly transmit the calculations obtained at 1432 or the analysis results obtained at 1434 to, for example, a client device (e.g., client device 108 in FIG. 1) or a medical device console 702 in some embodiments. Various types of data may be (e.g., measurement raw data collected by the sensor probe electronic module 708, electrical data converted from the measurement raw data, the aforementioned calculations, the final and/or the intermediate results of the aforementioned analysis, and others) may be buffered or otherwise stored at 1438.

In these embodiments shown as "implementation 2" in FIG. 14, the medical device console 702 may receive the calculations or the analysis results determined by the sensor probe electronic module 708 at 1426 via, for example, the wireless connection between the medical device console 702 and the sensor probe electronic module 708. These types of data may be buffered at 1428. In some of these embodiments, the medical device console 702 may perform one or more other analyses on the calculations, analysis results, and others at 1430. For example, the medical device console 702 may perform a statistical analysis, a pattern analysis, and others. The oxygen saturation results can be displayed to the user via a screen of the medical device console.

In one embodiment, the one or more other analyses at 1430 may include calculating a rate of change of oxygen saturation over a period of time. For example, a mesenteric artery supplying blood to the tissue can be clipped, and oxygen saturation of the tissue can be measured every 10 seconds, 30 seconds, one minute, two minutes, or other suitable time intervals. The blood supply to the tissue can be clipped for any suitable time period, as long as it does not negatively impact the patient's long-term health. For example, the blood supply may be clipped for a period anywhere between 1 minute, 2 minutes, 5 minutes, 10 minutes, 20 minutes, 30 minutes, or any other suitable time period. The measured oxygen saturation (e.g., in terms of percent) can be plotted against time. The rate of change may be calculated using any suitable method. For example, the rate of change can be measured and calculated around a midpoint of the induced ischemic period.

In one embodiment, the one or more other analyses at 1430 may include determining an amount of time required for 80 percent recovery of oxygen saturation for the tissue after restoring the blood supply to the tissue. For a healthy, normal tissue, it typically takes less time to achieve 80 percent recovery of oxygen saturation for the tissue. By contrast, for a tissue which is suffering from intestinal ischemia, it typically takes longer time to achieve 80 percent recovery of oxygen saturation for the tissue. It shall be noted that these analyses are described herein as examples, without limitation, and that other types of analyses may also be performed based on the measurement data or any other data derived from the measurement data.

Figure 15:
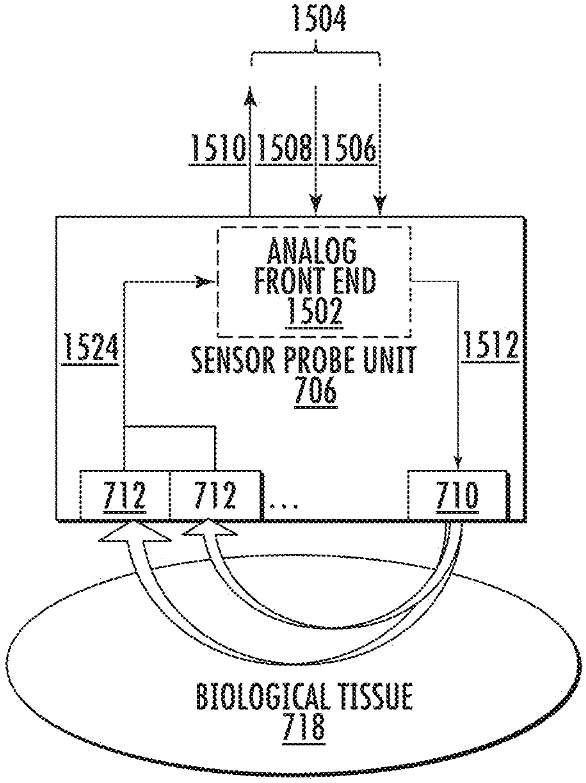
FIG. 15 shows a simplified schematic of an example sensor probe unit monitoring a biological tissue, according to some embodiments.

FIG. 15 shows a simplified schematic of an example sensor probe unit monitoring a biological tissue, according to some embodiments. More specifically, a sensor probe unit 706 may be positioned relative to a biological tissue 718 (e.g., a patient's tissue) for monitoring viability of the biological tissue 718. The sensor probe unit 706 may include an analog front end 1502 that receives power 1506 from, for example, an external power source or an internal power source such as a battery as well as one or more control signals 1508 from, for example, a processor or other controller.

In response to the one or more control signals 1508, the analog front end 1502 may then transmits one or more digital or optical or electrical signals 1512 to one or more light sources 710. These one or more digital and/or optical or electrical signals 1512 may be used to activate and control the one or more light sources 710 to emit one or more light beams, signals, or pulses having one or more wavelengths. For example, the one or more digital or optical or electrical signals 1512, or a combination, may control the intensity, duration of light emission, duty cycle, emission pattern, color, or wavelength, and others of the light beams, signals, or pulses.

Some of the incident light beams, signals, or pulses are absorbed into and scatter within or from the exterior surfaces the biological tissue 718, and a portion of such scattered light signals are detected and collected by a plurality of light detectors 712 of the sensor probe unit 706. The collected light signals 1524 may then be transmitted to the analog front end 1502 which may then relay a representation therefor 1510 through a cable connection 1504 to, for example, a medical device console in some embodiments.

Figure 16:
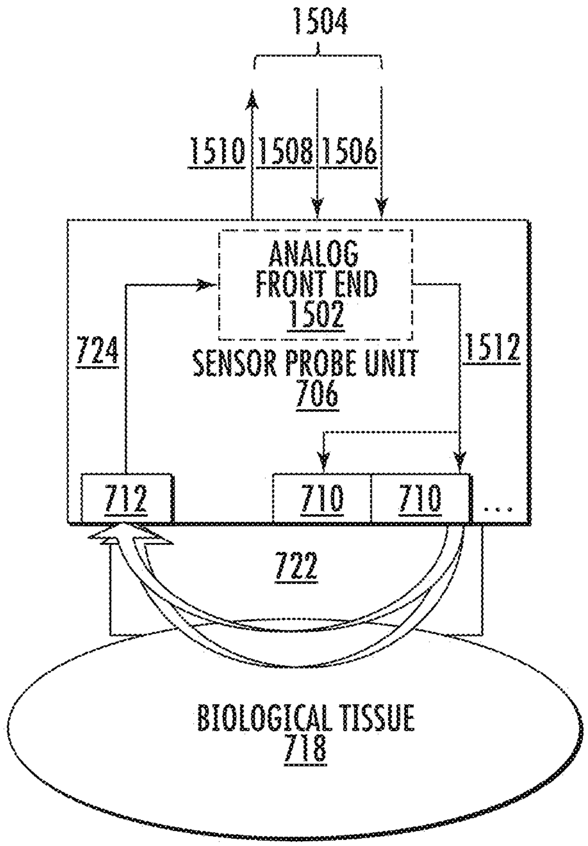
FIG. 16 shows a simplified schematic of another example sensor probe unit monitoring a biological tissue, according to some embodiments.

FIG. 16 shows a simplified schematic of another example sensor probe unit monitoring a biological tissue, according to some embodiments. Compared to the simplified schematic of the sensor probe unit shown in FIG. 15, the simplified schematic of the sensor probe unit 706 in FIG. 16 includes a plurality of light sources 710 and a single light detector 712. In addition, the sensor probe unit 706 may be positioned relative to the biological tissue 718 with an optional adapter, attachment, and others 722 that includes waveguides or passages that allow light beams, signals, or pulses to propagate through.

Figure 17:
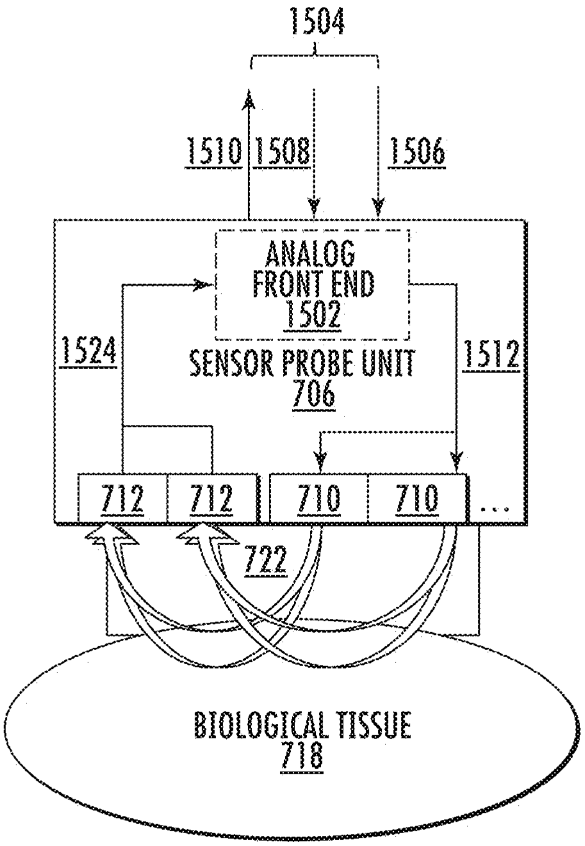
FIG. 17 shows a simplified schematic of another example sensor probe unit monitoring a biological tissue, according to some embodiments.

FIG. 17 shows a simplified schematic of another example sensor probe unit monitoring a biological tissue, according to some embodiments. Compared to the simplified schematic of the sensor probe unit shown in FIG. 16, the simplified schematic of the sensor probe unit 706 in FIG. 17 includes a plurality of light sources 710 and a plurality of light detectors 712 where the light beam, signal, or pulse from each light source 710 may be detected and collected by one or more light detectors 712 of the plurality of light detectors 712. Similar to that shown in FIG. 16, the sensor probe unit 706 may be positioned relative to the biological tissue 718 with an optional adapter, attachment, and others 722 that includes waveguides or passages that allow light beams, signals, or pulses to propagate through.

Figure 18:
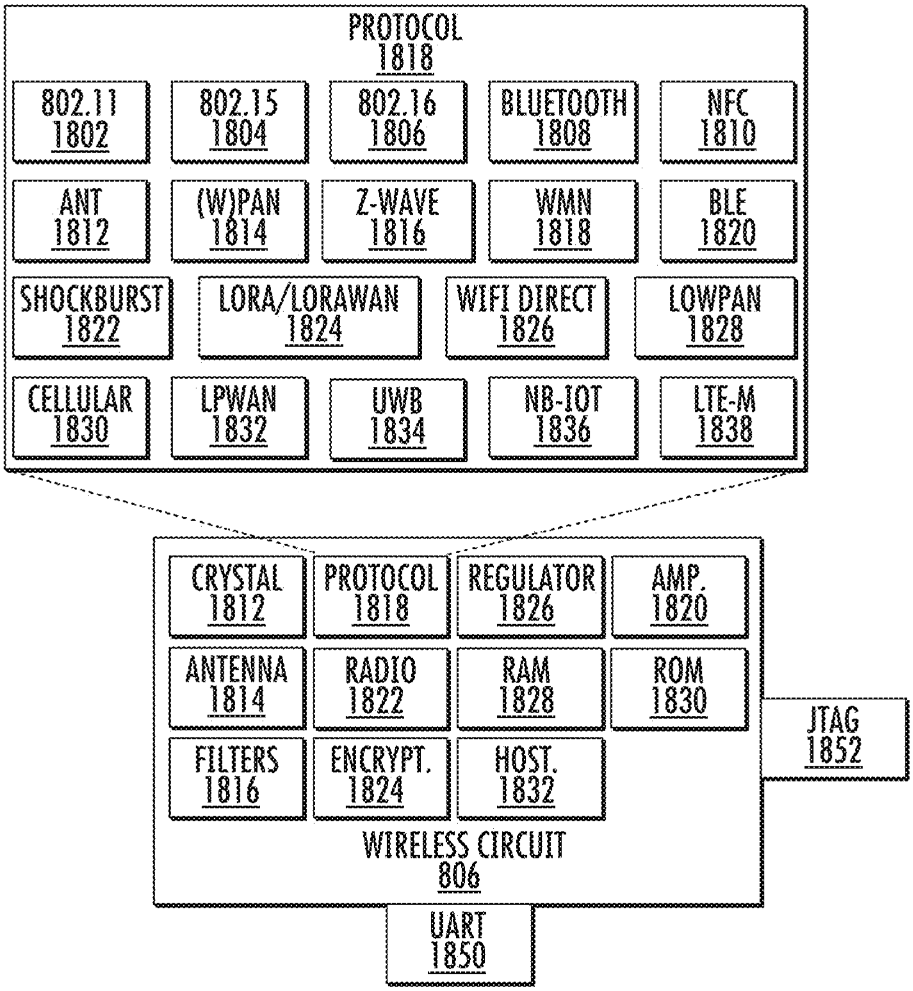
FIG. 18 shows an example wireless circuit comprising one or more protocols as well as some example protocols for the example wireless circuit, according to some embodiments.

FIG. 18 shows an example wireless circuit comprising one or more protocols as well as some example protocols for the example wireless circuit, according to some embodiments. FIG. 18 lists some example protocols 1818 that may be used for communication of data and signals between various systems, modules, or components described herein (e.g., between a sensor probe system 704 and a sensor probe electronic module 702, between a sensor probe unit 706 and a sensor probe electronic module 708, between a medical device system 102 and a client system 108, and others For example, these protocols 1818 may include, without limitation, one or more of the 802.11 protocols 1802, the 820.15 protocols 1804, the 820.16 protocols 1806, the Bluetooth protocols 1808 for building PAN; peer-to-peer wireless technology, the near-field communication or NFC protocols 1810, the ANT and/or ANT+ protocols 1812, the WPAN or PAN protocols 1814 for personal area network such as Zigbee or other 802.15.4, the Z-wave protocols 1816, the wired or wireless mesh type network protocol (WMN) 1818 for mesh type network with wired or wireless (WMN) connection using 802.11, the Bluetooth LE (low energy) or Bluetooth 5 protocols 1820, the ShockBurst network protocols 1822 for, e.g., Nike sports kit, a LoRa or LoRaWAN protocols 1824 that are some example protocols of LPWAN, a Wi-Fi Direct protocols 1826 for building WPAN; peer-to-peer wireless technology, a LoWPAN protocols 1828 for low-power long distance technologies such as low-power wide area network including LoRa or LoRaWAN, a cellular network protocols 1830 for long distance cellular technologies such as GPRS or general packet radio services, GSM or global system for mobile communication, 3G, WiMAX, 4G, LTE or Long-Term Evolution, 5G, or 6G, and others protocols, a LPWAN protocol 1832 for low power wide area network: including 1824, 1836, 1838, and others, an UWB or ultrawide band communication protocol 1834, an NB-IoT protocol 1836, an LTE-M protocol 1838, a Zigbee protocol, a fuleband SE BLE protocol used by Nike Plus, or any other similar or equivalent communication protocols.

These protocols may function in tandem with a wireless circuit or integrated circuit 806 that comprises, for example but without limitation, an oscillation crustal 1812, one or more protocols 1818, a regulator 1826, an amplifier 1820, an antenna 1814, a radio 1822, random-access memory or RAM 1828, read-only memory or ROM 1830, one or more filters 1816 such as an RF (radio-frequency) filter, an encryption module or circuitry 1824, and/or a host 1832. The wireless integrated circuit 806 may also function together with Joint task Action Group (JTAG) 1852 and a universal asynchronous receiver and transmitter (UART) 1850 that is one of the most used device-to-device hardware communication protocols among embedded systems, microcontrollers, and computing devices as various systems, devices, and components described herein. A purpose of a transmitter and receiver line for each device is to transmit and receive serial data intended for serial communication.

JTAG is an industry standard for verifying designs and testing printed circuit boards after manufacture. JTAG implements standards for on-chip instrumentation in electronic design automation as a complementary tool to digital simulation and is widely adopted in Internet of Things (IoT). For example, a designer can JTAG a Bluetooth chip and obtain the MAC ID, which could prove that a phone is paired with that device.

Figure 19A:
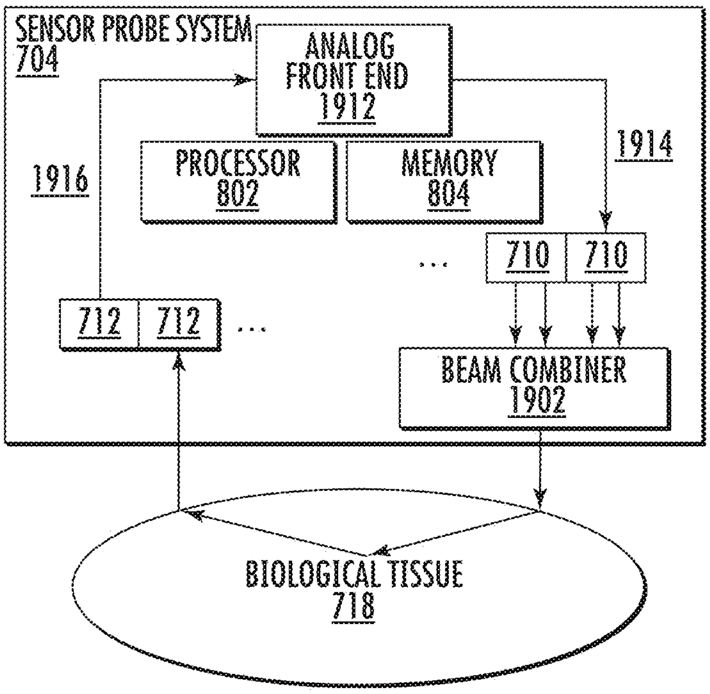
FIG. 19A shows a simplified schematic diagram of an example of an implementation of a sensor probe unit monitoring a biological tissue, according to some embodiments.

FIG. 19A shows a simplified schematic diagram of an example of an implementation of a sensor probe unit monitoring a biological tissue, according to some embodiments. Compared to the simplified schematic of the sensor probe unit shown in FIG. 17, the simplified schematic of the sensor probe unit 706 in FIG. 19 includes an optional processor, processor core, or thread of execution 802, an optional memory 804, a plurality of light sources 710, and a plurality of light detectors 712. Moreover, the plurality of light sources 710 may receive a control signal 1914 that causes the one or more light sources 710 to emit one or more light beams, signals, or pulses where the light beams, signals, or pulses from the plurality of light sources 710 may be first aggregated with an optional beam combiner 1902. In some embodiments, each pair of light sources emitting two different frequencies of light may be operatively coupled to a beam combiner 1902 where the reflected light via the physiological medium (e.g., the biological tissue 718) may be detected by all of a plurality of light detectors 712.

In some embodiments whether the one or more light sources 710 include more than one light source, the light beams, signals, or pulses emitted by these multiple light sources may include multiple, different wavelengths. In some embodiments, the one or more light sources 710 include only one single light source so that the optional beam combiner 1902 is no longer needed. In some of these embodiments, this single light source 710 may produce light at different frequencies (or wavelengths) allowing this single light source to emit multiple colors of light simultaneously. In some embodiments, the one or more light sources 710 may include multiple light sources whose respective light outputs may be time-multiplexed by using, for example, time division multiplexing that divides the transmission time for the multiple light sources into multiple time slots where each light source is assigned a different time slot. In these embodiments, the optional beam combiner 1902 may longer be needed in some embodiments. In some other embodiments that do employ an optional beam combiner 1902, the optional beam combiner 1902 may be used as a "pass-through" to allow the multiple light outputs from these multiple light sources 710 (albeit in different time slots) to exit a single opening of the sensor probe unit 706 (rather than having multiple openings each for a different light source 710) without actually combining multiple light outputs from multiple light sources 710.

The aggregated light beams, signals, or pulses may then be directed towards and scatter or from the exterior surfaces a biological tissue 718. Some of the scattered light signals may then be detected and collected by a single or a plurality of light detectors 712 that in turn transmit the collected, reflected, or refracted light signals 1916 to the analog front end 1912. Unlike that shown in FIG. 16, the sensor probe unit 706 may be positioned relative to the biological tissue 718 without using an optional adapter, attachment, and others 722 that includes waveguides and/or passages that allow light beams, signals, or pulses to propagate through. In some embodiments, the single or plurality of light detectors 712 may include a multispectral sensor or detector (e.g., a Buried Quad Junction or BQJ photodetector or any other sensors or detectors with sufficiently high spectral discrimination ability). As a result, some embodiments employ a single LED 710 (e.g., a single-wavelength or multi-wavelength LED) and a single light detector 712 (e.g., a multi-spectral sensor or detector) to reduce a significant portion of inaccuracies or imprecisions related to the scattering phenomena and LED deterioration. There typically needs to be at least two unique wavelengths for a proper measurement of oxygen saturation. However, a single-wavelength LED can technically work, if that single-wavelength LED were spectrally broad (e.g., based on its specification).

Figure 19B:
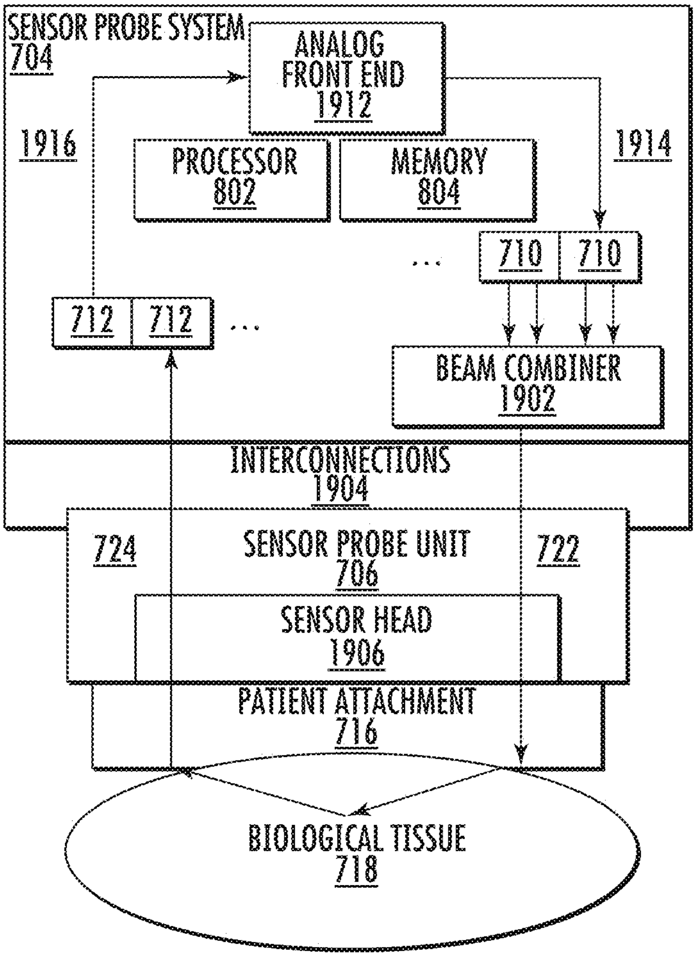
FIG. 19B shows another simplified schematic diagram of another example of an implementation of a sensor probe unit monitoring a biological tissue, according to some embodiments.

FIG. 19B shows another simplified schematic diagram of another example implementation of a sensor probe unit monitoring a biological tissue, according to some embodiments. Compared to FIG. 19A, the analog front end 1912, the optional processor, processor core, or thread of execution 802, the optional memory 804, the light sources 710, the light detectors 712, and the beam combiner 1902 may be implemented in a separate module (e.g., a sensor probe electronic module 708 in FIG. 7 or other appropriate module) that is physically separate from a sensor probe unit 706 and is interconnected with the sensor probe unit 706 having a sensor head 1906 via a wired or wireless interconnection 1904. The sensor probe unit 706 may be attached to or otherwise coupled with a biological tissue 718 via a patient attachment 716.

Figure 20A:
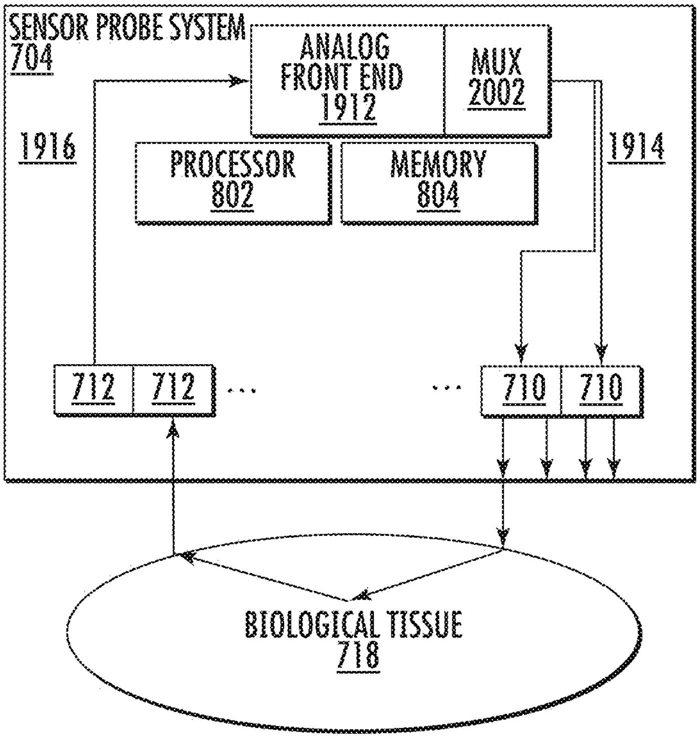
FIG. 20A shows another simplified schematic diagram of an example of an implementation of a sensor probe unit monitoring a biological tissue, according to some embodiments.

FIG. 20A shows another simplified schematic diagram of an example of an implementation of a sensor probe unit monitoring a biological tissue, according to some embodiments. Compared to the simplified schematic of the sensor probe unit shown in FIG. 19, the simplified schematic of the sensor probe system 704 in FIG. 20 includes a processor, processor core, or thread of execution 802, a memory 804, a plurality of light sources 710, and a plurality of light detectors 712 that may be arranged in a sensor probe electronic subsystem or module (e.g., 708) and a sensor probe unit (e.g., 706). Moreover, the plurality of light sources 710 may receive a control signal 1914 (e.g., a current signal) that causes the one or more light sources 710 to emit one or more light beams, signals, or pulses where the light beams, signals, or pulses may be emitted from the plurality of light sources 710 subject to the respective control signals or drive signals (e.g., electrical currents), or a combination, that are generated by the analog front end 1912 and selected and forwarded by an optional multiplexer 2002.

In some embodiments, the multiplexer 2002 may include an electrical multiplexer that selects an electrical signal (e.g., a control signal from time-division multiplexing, a drive signal for a particular light source, and others.) from a plurality of input signals and output the selected electrical signal to the corresponding light source 710. In some embodiments that include the optional multiplexer 2002, the optional multiplexer 2002 may be implemented as a part of the analog front end 1912 that in and of itself performs the time-division multiplexing to fire up each light source individually. In some of these embodiments where a light source includes a multi-spectral light source (e.g., a single multiple-color light emitting diode) or multiple light emitting diodes emitting light each emitting light having a different wavelength, the multiple-spectral light source or the multi-LEDs may be driven individually to emit light having a single wavelength at a time by using, for example, time-division multiplexing. In some other embodiments, the multiplexer 2002 may be a separate component of the sensor probe system 704 and is operatively connected to the analog front end 1912 to receive input signals.

In some other embodiments, the multiplexer 2002 may include a wavelength division multiplexing (WDM) multiplexer (mux) such as a coarse wavelength division multiplexing mux (CWDM mux), a dense wavelength multiplexing mux (DWDM mux), and others. A WDM mux combines multiple optical signals of different wavelengths while a WDM demux separates optical signals of different wavelengths into multiple optical signals each having a single wavelength. In these embodiments, the optional WDM multiplexer may be placed after the plurality of light sources that provide their respective output light to the WDM multiplexer. A WDM mux allows for transmission of multiple optical signals of different frequencies over a single optical fiber. A CWDM mux differs from a DWDM mux in the wavelength steps between channels where CWDM mux may have tens of nanometers for the wavelength step, and DWDM mux hay have one nanometer or smaller wavelength steps. With an optional WDM multiplexer, a single optical fiber may be used in transmitting optical signals of multiple light sources 710 onto the biological tissues 718 so that the reflected light off the biological tissue 718 may be detected by the light detectors 712.

The output light beams, signals, or pulses may then be directed towards and scatter within or from the exterior surfaces a biological tissue 718. Some of the scattered light signals may then be detected and collected by a plurality of light detectors 712 that in turn transmit the collected, reflected, or refracted light signals 1916 to the analog front end 1912. Like that shown in FIG. 19, the sensor probe system 704 may be positioned relative to the biological tissue 718 without using an optional adapter, attachment, and others 722 that includes waveguides and/or passages that allow light beams, signals, or pulses to propagate through.

Figure 20B:
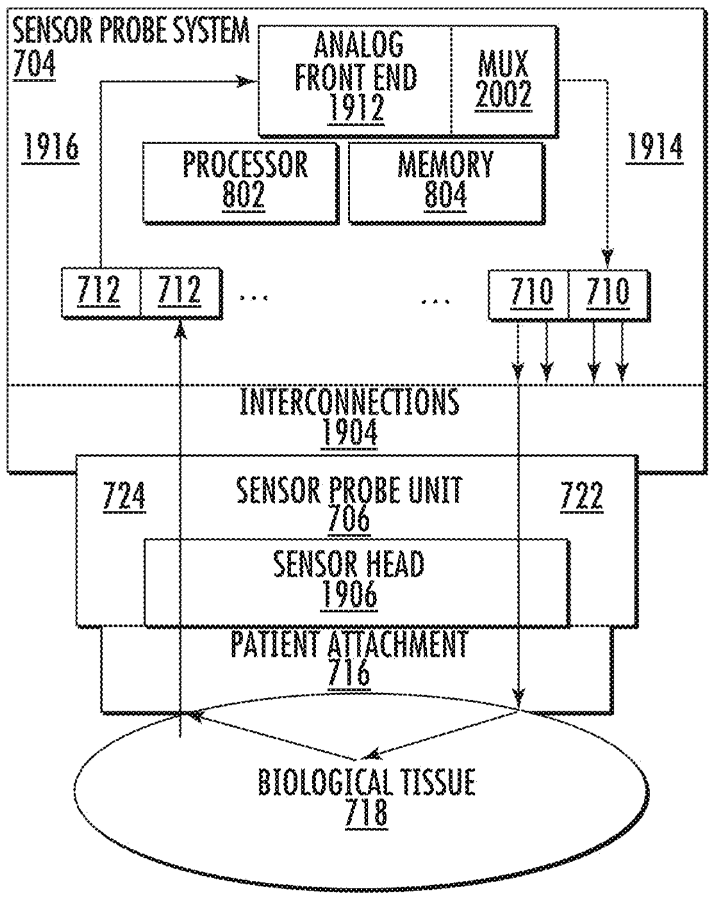
FIG. 20B shows another simplified schematic diagram of an example of an implementation of a sensor probe unit monitoring a biological tissue, according to some embodiments.

FIG. 20B shows another simplified schematic diagram of another example implementation of a sensor probe system 704 monitoring a biological tissue, according to some embodiments. Compared to FIG. 20A, the analog front end 1912, the processor, processor core, or thread of execution 802, the memory 804, the light sources 710, the light detectors 712, and the optional multiplexer 2002 may be implemented in a separate module (e.g., a sensor probe electronic module 708 in FIGS. 7A-7H or other appropriate module) that is physically separate from a sensor probe unit 706 and is interconnected with the sensor probe unit 706 having a sensor head 1906 via a wired or wireless interconnection 1904. The sensor probe unit 706 or a portion thereof in the sensor probe system 704 may be attached to or otherwise coupled with a biological tissue 718 via a patient attachment 716 in some embodiments.

Figure 21A:
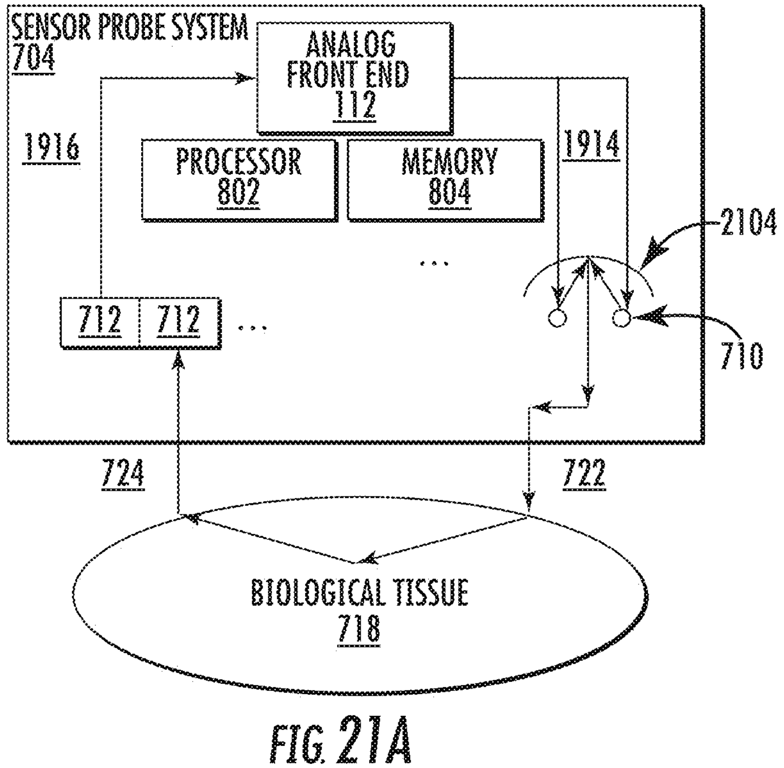
FIG. 21A shows another simplified schematic diagram of an example of an implementation of a sensor probe unit monitoring a biological tissue, according to some embodiments.

FIG. 21A shows another simplified schematic diagram of an example of an implementation of a sensor probe system 704 monitoring a biological tissue, according to some embodiments. Compared to the simplified schematic of the sensor probe system 704 shown in FIG. 20, the simplified schematic of the sensor probe system 704 in FIG. 21 includes a processor, processor core, or thread of execution 802, a memory 804, a plurality of light sources 710, and a plurality of light detectors 712. Moreover, the plurality of light sources 710 may receive respective control or drive signals 1914 (e.g., a current signal) that cause the one or more light sources 710 to emit one or more light beams, signals, or pulses where the light beams, signals, or pulses from the plurality of light sources 710 may be directed towards an optical element 2104 (e.g., a concave mirror, a spherical mirror, a convex lens, and others) which then optically converges the incident light beams, signals, or pulses from the plurality of light sources 710 via reflection or refraction.

The output light beams, signals, or pulses 722 from the curved optical element 2002 may then be directed towards and scatter or reflect within or from the exterior surfaces a biological tissue 718. Some of the scattered light signals 724 may then be detected and collected by a plurality of light detectors 712 that in turn transmit the collected, reflected or refracted light signals 1916 to the analog front end 1912. Like that shown in FIG. 20, the sensor probe system 704 or the sensor probe unit 708 thereof may be positioned relative to the biological tissue 718 without using an optional adapter, attachment, and others 722 that includes waveguides and/or passages that allow light beams, signals, or pulses to propagate through.

Figure 21B:
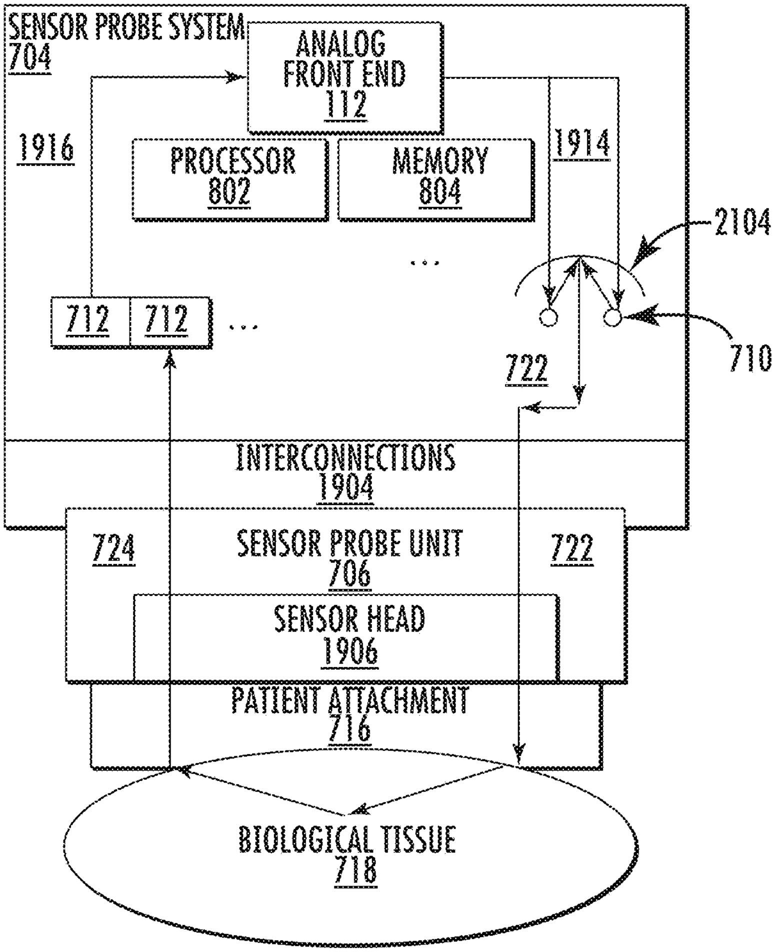
FIG. 21B shows another simplified schematic diagram of an example implementation of a sensor probe unit monitoring a biological tissue, according to some embodiments.

FIG. 21B shows another simplified schematic diagram of another example of an implementation of a sensor probe system 704 monitoring a biological tissue, according to some embodiments. Compared to FIG. 21A, the analog front end 1912, the processor, processor core, or thread of execution 802, the memory 804, the light sources 710, the light detectors 712, and the optical element 2104 (e.g., a concave mirror, a spherical mirror, a convex lens, and others) may be implemented in a separate module (e.g., a sensor probe electronic module 708 in FIGS. 7A-7H or other appropriate module) where the separate module is physically separate from a sensor probe unit 706 and is interconnected with the sensor probe unit 706 having a sensor head 1906 via a wired or wireless interconnection 1904. The sensor probe unit 706 may be attached to or otherwise coupled with a biological tissue 718 via a patient attachment 716.

Figure 22B:
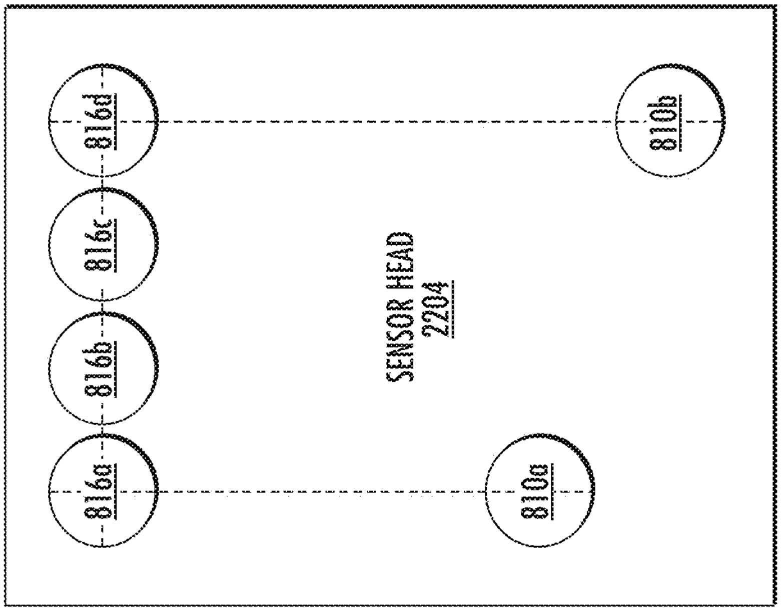
FIGS. 22A-22B show some simplified examples of a sensor head of a sensor probe unit with respective configurations of light emitters and light detectors, according to some embodiments.
Figure 22A:
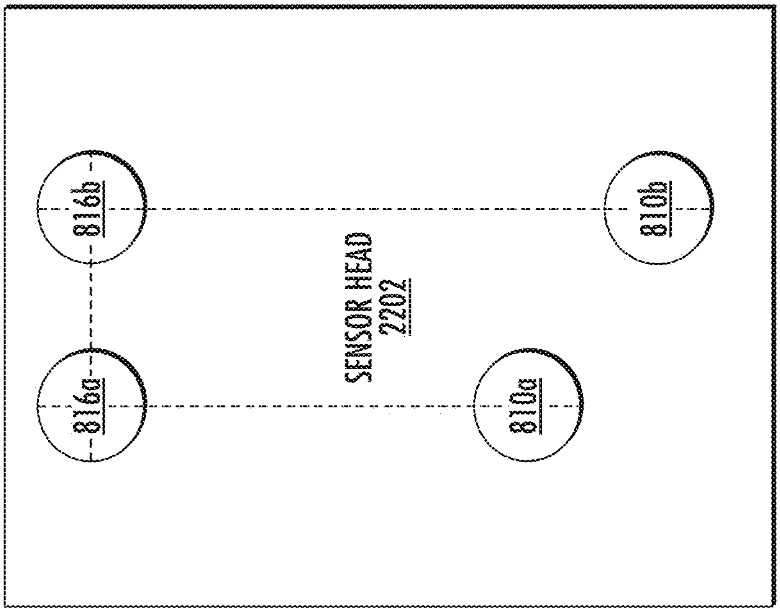

FIGS. 22A-22B show some simplified examples of a sensor head of a sensor probe unit 706 with respective configurations of light emitters and light detectors, according to some embodiments. More specifically, FIG. 22A shows a representation of an orientation of optical structures that are coupled to light sources and light detectors in accordance with an embodiment of the present invention. A sensor head 2202 includes two light detector optical structures 816*a* and 816*b* and two light source optical structures 810*a* and 810*b*. Although two source optical structures 810*a* and 810*b* and two light detector optical structures 816*a* and 816*b* are shown, it should be appreciated that the number of source optical structures and detector optical structures may vary widely. The positioning of source optical structures 810*a* and 810*b* relative to the light detector optical structures 816*a* and 816*b* may also vary, e.g., light source optical structures 810*a* and 810*b* may generally have either a symmetric or a non-symmetric (e.g., asymmetric) orientation with respect to detector optical structures 816*a* and 816*b*. As shown in FIG. 22A, the two detectors 816*a* and 816*b* are arranged alone a first line, and the two light sources 810*a* and 810*b* are arranged alone a second line that is not parallel with the first line. Further, the sensor head may have an arrangement that is a mirror image of that shown in FIG. 22A-22B, such as left and right mirror image.

In some embodiments, one or more light sources (e.g., 810*a*, 810*b*, and others) and a plurality of light detectors (e.g., 816*a*, 816*b*, 816*c*, 816*d*, and others) may be arranged on an exterior surface of the enclosure or housing of the sensor probe unit (or referred to as a sensor head). In these embodiments, each light source corresponds to a respective light source structure (e.g., an opening, an opening with a window, an opening with a filled in or covered transparent or translucent optical component such as a piece of polymeric material, or glass, or any other materials suitable for optical structures or optical fiber, and others. that allows light to pass through). Similarly, each light detector corresponds to a respective light detector structure (e.g., an opening, an opening with a window, an opening with a filled in or covered transparent or translucent optical component such as a piece of polymeric material or glass, and others) that allows reflected light (e.g., light emitted from a light source, is reflected by the biological tissues) to be detected by a detector. A light detector may be positioned relative to its corresponding light detector structure in such a way that the light detector receives all or most of incoming, reflected light through its corresponding light detector structure, and reflected light passing through one or more other light detector structures or at least a sufficient portion thereof (e.g., sufficient reflected light through another light detector structure to cause inaccuracy in the detection by the light detector) does not end up being detected by the light detector (e.g., by scattering) to cause inaccuracy in reflected light detection by the light detector. For example, a light detector may be positioned sufficiently close to its corresponding light detector structure so that all or at least most of the reflected light detected by the light detector is through its corresponding light detector structure. Similarly, a light source may be positioned relative to a respective light source structure so that all or most of the emitted light from the light source passes through the respective light source structure without entering and passing through one or more other light source structures, if any. For example, a light source may be positioned sufficiently close to its corresponding light source structure so that all or at least most of the emitted light emitted by the light source passes through its corresponding light source structure.

In general, as previously mentioned, light provided through source optical structures 810*a* and 810*b* reflects off of tissue and underlying layers when sensor head 2202 is in contact with or in close proximity of a surface of the biological tissue. Once the light reflects, the reflected or refracted light is gathered by detector optical structures 816*a* and 816*b*. Moreover, although the two light sources 810*a* and 810*b* as well as the two light detector optical structures 816*a* and 816*b* appear to be arranged along a rectilinear arrangement along respective straight-line segments in FIG. 22A, either the light sources or the light detectors or both may be arranged in a curvilinear arrangement, rather than a straight-line arrangement in some embodiments.

Further, the spacing value between two adjacent light sources or between two adjacent light detectors may or may not be constant so long as any two pairs of light source and light detector do not result in the same distance between the light source and the light detector. For example, the light source optical structures or the light detector optical structures in the sensor head 2204 may be arranged to create two (representing the total number of light source optical structures) times two (representing the total number of light detector optical structures) or four different distances. As shown in FIG. 22B, the four detectors 816*a*-816*d* are arranged alone a first line, and the two light sources 810*a* and 810*b* are arranged alone a second line that is not parallel or collinear with the first line.

FIG. 22B further shows another sensor head 2204 that includes two light source optical structures 810*a* and 810*b* as well as four light detector optical structures 816*a*-816*d*. As described above, although the two light sources 810*a* and 810*b* as well as the two light detector optical structures 816*a*-816*d* appear to be arranged along a rectilinear arrangement along respective straight-line segments in FIG. 22B, either the light sources or the light detectors or both may be arranged in a curvilinear arrangement, rather than a straight-line arrangement in some embodiments.

Further, the spacing value between two adjacent light sources or between two adjacent light detectors may or may not be constant so long as any two pairs of light source and light detector do not result in the same distance between the light source and the light detector. For example, the light source optical structures and the light detector optical structures in the sensor head 2204 may be arranged to create two (representing the total number of light source optical structures) times four (representing the total number of light detector optical structures) or eight different distances.

Moreover, although the sensor head 2202 and 2204 are represented as having rectangular shapes, it shall be noted that sensor heads may have any geometric profiles in various embodiments. Further, the light sources and light detectors are represented as circular shapes for the sole purpose and ease of illustration and explanation while light sources and light detectors as well as their respective openings as described herein may also have various different geometric profiles.

In some embodiments, the orientation of the light source optical structures with respect to the light detector optical structures will be described in accordance with an embodiment of the present invention. A sensor head (e.g., 2202 or 2204), which may be of substantially any shape or size, is a part of a probe that is a part of an overall system that measures oxygen saturation levels in tissue. Sensor head 200 is arranged to accommodate light source arrangements 810*a* and 810*b*, and light detector arrangements 816*a* and 816*b* in the sensor head 2202 (or 816*a-d* in 2204). For ease of discussion, although the light source arrangements 810*a* and 810*b* are generally optical structures (including fiber optic cables or optical fibers and others) coupled to light sources and light detector arrangements 810*a*-810*b* and 816*a*-816*d* are generally optical structures optically coupled (e.g., via positioning) to photodetectors, the light source arrangements 810*a*-810*b* are referred to in this application as light sources, and detector arrangements 816*a*-816*b* or 816*a*-816*d* are referred to in this application as light detectors.

Light sources 810*a*-810*b* are arranged such that they are in an offset arrangement relative to light detectors 816*a*-816*d*. That is, light source 810*a* and source 810*b* are not equidistant to detectors 816*a* and 816*b* relative to at least one axis. Light detectors 816*a*-816*b* are arranged such that a centerline of detectors 816*a* and 816*b* is approximately parallel to an x-axis (e.g., the horizontal axis in FIG. 22A or 22B). Typically, a centerline passes through a center point of each light detector 816*a* and 816*b*. Light sources 810*a* and 810*b* are arranged such that a centerline of light source 810*a* is parallel to a centerline of light source 810*b*, but is not coincident with centerline passing through the light source 810*b*. The centerline passes through a center point of source 810*a* and is parallel to the x-axis, while another centerline passes through a center point of source 810*b* and is parallel to the x-axis (e.g., the horizontal axis in FIG. 22A or 22B).

A distance y1 the y-axis (e.g., the vertical axis in the orientation of FIG. 22A or 22B) between the horizontal centerline passing through light detectors 816*a* or 816*b* and the horizontal centerline passing through the light source 810*a* along differs from a distance y2 between the horizontal centerline passing through the light detector 816*a* or 816*b* and the horizontal centerline passing through the light source 810*b*. Although distance y2 is shown as being greater than distance y1, it should be appreciated that distance y1 may instead be greater than y2. The difference between distance y2 and distance y1 is generally characteristic of the offset arrangement, or substantially unbalanced arrangement, of light sources 810*a* and 810*b* relative to detectors 816*a* and 816*b*. In other words, there is effectively a lack of symmetry in the placement of light sources 810*a* and 810*b*. In of embodiments, there are no intervening light sources or light detectors between each of the two light sources and each of the plurality of light detectors.

In general, more than two detectors may be used in conjunction with a pair of detectors to monitor oxygen saturation in tissue. By way of example, three or four detectors may be used to detect light that is provided by a pair of sources and is reflected or refracted off of a tissue surface. It should be appreciated that some of the light may be reflected or refracted from tissue at various depths beneath the tissue surface. That is, light may be reflected or refracted off the tissue surface and off of tissue that underlies the surface. The tissue that underlies the surface and allows light to be reflected or refracted may be as deep as approximately one centimeter below the surface of the tissue. As shown in FIG. 22A, the two detectors 816*a* and 816*b* are arranged alone a first line, and the two light sources 810*a* and 810*b* are arranged alone a second line that is not parallel or collinear with the first line. In some embodiments, this implementation shown in FIG. 22A provides four pairs each containing a source and a detector that is spaced apart from the corresponding source at a distance value. In some of these embodiments, these four pairs provide four different distance values at least some of which are used in the determination of oxygen saturation. It shall be noted that a sensor probe unit (or a sensor head) may contain any number of light sources and any number of light detectors. For example, a sensor probe unit (or a sensor head) may contain two light sources (e.g., 810*a* and 810*b*) and three light detectors to provide six light source-detector distance values.

FIG. 22B further shows a sensor head 2204 which is arranged to include a pair of light sources 810*a* and 810*b* or, more specifically, light source arrangements and four detectors 816*a*-816*d* or, more specifically, light detector arrangements, in accordance with an embodiment of the present invention. A sensor head 2204 includes four light detectors 816*a*-816*d* which are arranged such that the center points of light detectors 816*a*-816*d* are substantially aligned along the horizontal centerline that passes through light detectors 816*a*-816*d* and is substantially parallel to an x-axis (e.g., the horizontal axis in the orientation of FIG. 22A or 22B). Sensor head 2204 also includes sources 810*a* and 810*b* each of which includes a center point. A horizontal centerline that passes through light source 810*a* of 2204 is parallel to the horizontal x-axis, and a horizontal centerline that is parallel to the horizontal x-axis passes through the center point of light source 810*b* of 2204.

In the described embodiment, a distance y1 along the vertical y-axis between the centerline passing through light detectors 816*a*-816*d* and the horizontal centerline passing through light source 810*a* of 2204 is not equal to a distance y2 along the vertical y-axis between the centerline passing through the light detectors 816*a*-816*d* and the centerline passing through light source 810*b*. Distance y1 may be approximately 0.2 inches, as for example approximately 0.197 inches, while distance y2 may be approximately 0.24 inches, as for example 0.236 inches. It should be appreciated that distance y1 and distance y2 may vary widely depending upon any number of factors. The factors include, but are not limited to, the overall size of light sources 810*a*-810*b* and light detectors 816*a*-816*d*, the overall size of sensor head 2204, and the application for which sensor head 2204 is intended. While distance y2 is shown as being greater than distance y1, distance y1 may instead be greater than distance y2. In general, the difference between distance y2 and distance y 1 is at least approximately 0.3 inches. For example, distance y2 and distance y1 may differ by approximately 1.0 inches.

The positioning of light sources 810*a*-810*b* and light detectors 816*a*-810*d* may vary widely. By way of example, for an embodiment in which light sources 810*a* and 810*b* and light detectors 816*a*-816*d* are each approximately 1 millimeter in diameter, the center points of light sources 810*a* and 810*b* may be separated by a distance d2 that is approximately 0.22 inches relative to the horizontal x-axis and by a distance y4 that is approximately 0.04 inches. Light detectors 816*a*-816*d* may be arranged such that the horizontal center line passing through the light detectors 816*a*-816*d* is offset from a top edge of sensor head 2204 by a distance y3 that is approximately 0.06 inches, and such that adjacent light detectors 816*a*-816*d* are separated by a distance d1 that is between approximately 0.06 inches to approximately 0.07 inches. Sensor head 2204 may have a width of approximately 0.34 millimeters along the horizontal x-axis and a height of approximately 0.49 millimeters along the vertical y-axis when light detectors 816*a*-816*d* and light sources 810*a* and 810*b* are spaced as described above. However, sensor head 2204 generally has dimensions that may vary widely, e.g., dimensions which may vary depending upon the application for which sensor head 2204 is intended.

While a lack of symmetry in the positioning of sensors relative to detectors has been described as being such that distances between sensors and detectors are not equal relative to the vertical y-axis, a lack of symmetry may instead or additionally have a lack of symmetry relative to an x-axis. As shown in FIG. 22B, the four detectors 816*a*-816*d* are arranged alone a first line, and the two light sources 810*a* and 810*b* are arranged alone a second line that is not parallel or collinear with the first line. In some embodiments, this implementation shown in FIG. 22B provides eight pairs each containing a source and a detector that is spaced apart from the corresponding source at a distance value. In some of these embodiments, these eight pairs provide eight different distance values at least some of which are used in the determination of oxygen saturation. It shall be noted that a sensor probe unit (or a sensor head) may contain any number of light sources and any number of light detectors. For example, a sensor probe unit (or a sensor head) may contain two light sources (e.g., 810*a* and 810*b*) and three light detectors to provide six light source-detector distance values.

Figure 23B:
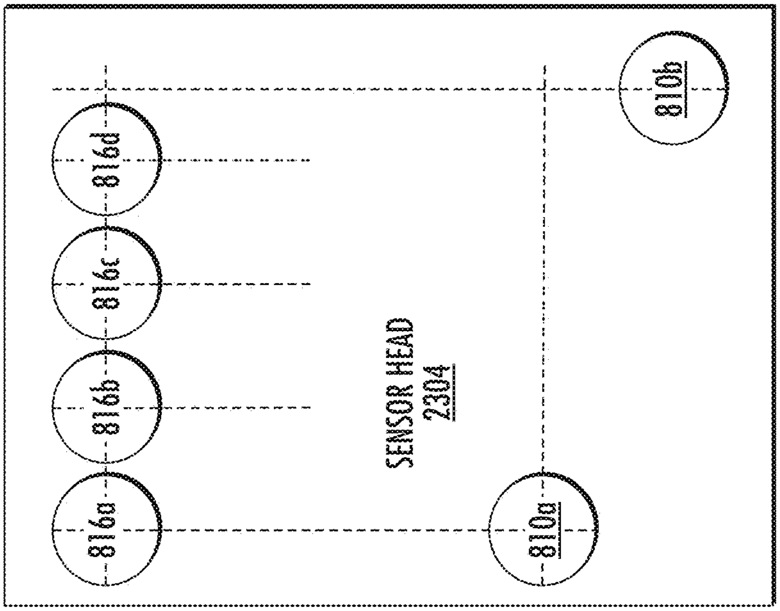
FIGS. 23A-23B show some other simplified examples of another sensor head of a sensor probe unit with respective configurations of light emitters and light detectors, according to some embodiments.
Figure 23A:
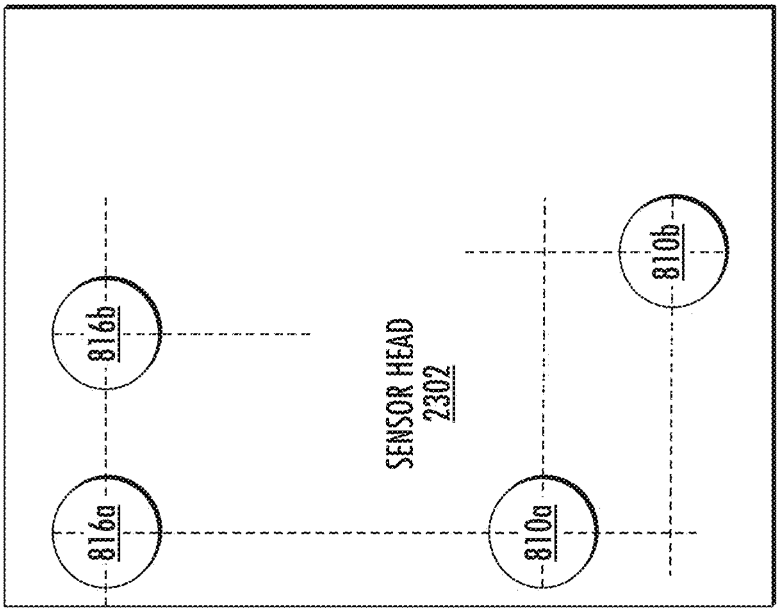
Figure 24A:
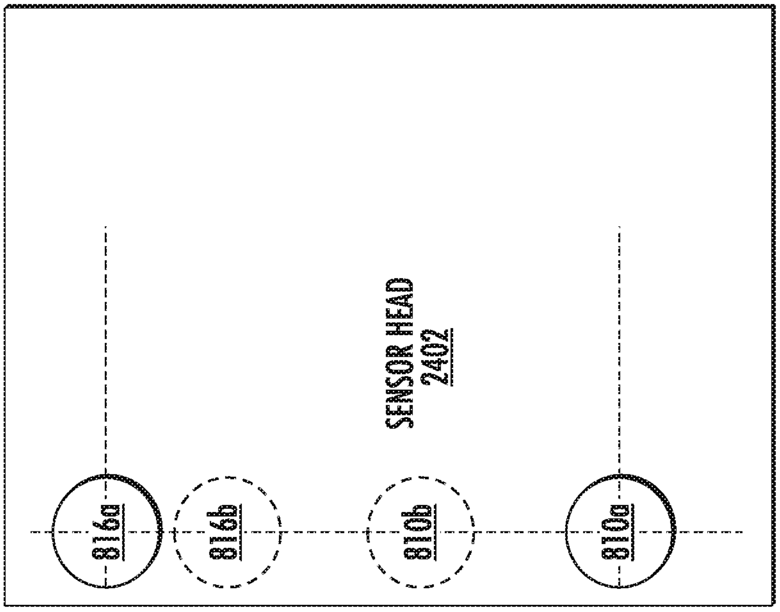
FIGS. 24A-24B show some other simplified examples of another sensor head of a sensor probe unit with respective configurations of light emitters and light detectors, according to some embodiments.

FIG. 23A shows some other simplified examples of another sensor head of a sensor probe unit (706 in one or more of FIGS. 7A-7L and 8-14) with respective configurations of light emitters and light detectors, according to some embodiments. More specifically, FIG. 23A shows a representation of an orientation of optical structures that are coupled to light sources and light detectors in accordance with an embodiment of the present invention. A sensor head 2302 includes two light detector optical structures 816*a* and 816*b* and two light source optical structures 810*a* and 810*b*. Although two source optical structures 810*a* and 810*b* and two light detector optical structures 816*a* and 816*b* are shown, it should be appreciated that the number of source optical structures and detector optical structures may vary widely. The positioning of source optical structures 810*a* and 810*b* relative to the light detector optical structures 816*a* and 816*b* may also vary, e.g., light source optical structures 810*a* and 810*b* may generally have either a symmetric or a nonsymmetric (e.g., asymmetric) orientation with respect to detector optical structures 816*a* and 816*b*. As shown in FIG. 23A, the two detectors 816*a* and 816*b* are arranged alone a first line, and the two light sources 810*a* and 810*b* are arranged alone a second line that is not parallel or collinear with the first line. In some embodiments, this implementation shown in FIG. 24A provides four pairs each containing a source and a detector that is spaced apart from the corresponding source at a distance value. In some of these embodiments, these four pairs provide four different distance values at least some of which are used in the determination of oxygen saturation. It shall be noted that a sensor probe unit (or a sensor head) may contain any number of light sources and any number of light detectors. For example, a sensor probe unit (or a sensor head) may contain two light sources (e.g., 810*a* and 810*b*) and three light detectors to provide six light source-detector distance values.

In general, as previously mentioned, light provided through source optical structures 810*a* and 810*b* reflects off of tissue and underlying layers when sensor head 2302 is in contact with or in close proximity of a surface of the biological tissue. Once the light reflects, the reflected or refracted light is gathered by detector optical structures 816*a* and 816*b*. Moreover, although the two light sources 810*a* and 810*b* as well as the two light detector optical structures 816*a* and 816*b* of 2302 appear to be arranged along a rectilinear arrangement along respective straight-line segments in FIG. 23A, either the light sources or the light detectors or both may be arranged in a curvilinear arrangement, rather than a straight-line arrangement in some embodiments.

Further, the spacing value between two adjacent light sources or between two adjacent light detectors may or may not be constant so long as any two pairs of light source and light detector do not result in the same distance between the light source and the light detector. For example, the light source optical structures and the light detector optical structures in the sensor head 2304 in FIG. 23B may be arranged to create two (representing the total number of light source optical structures) times two (representing the total number of light detector optical structures) or four different distances. As shown in FIG. 23B, the four detectors 816*a*-816*d* are arranged alone a first line, and the two light sources 810*a* and 810*b* in the sensor head 2304 are arranged alone a second line that is not parallel or collinear with the first line. In some embodiments, this implementation shown in FIG. 23B provides eight pairs each containing a source and a detector that is spaced apart from the corresponding source at a distance value. In some of these embodiments, these eight pairs provide eight different distance values at least some of which are used in the determination of oxygen saturation.

FIG. 23B further shows another sensor head 2304 that includes two light source optical structures 810*a* and 810*b* as well as four light detector optical structures 816*a*-816*d*. As described above, although the two light sources 810*a* and 810*b* as well as the two light detector optical structures 816*a*-816*d* appear to be arranged along a rectilinear arrangement along respective straight-line segments in FIG. 23, either the light sources or the light detectors or both may be arranged in a curvilinear arrangement, rather than a straight-line arrangement in some embodiments.

Further, the spacing value between two adjacent light sources or between two adjacent light detectors may or may not be constant so long as any two pairs of light source and light detector do not result in the same distance between the light source and the light detector. For example, the light source optical structures or the light detector optical structures in the sensor head 2304 may be arranged to create two (representing the total number of light source optical structures) times four (representing the total number of light detector optical structures) or eight different distances.

A sensor head 2302 or 2304 that includes a pair of light sources which are in an offset arrangement relative to a set of four detectors with respect to the horizontal x-axis will be described. A sensor head 2304 includes four light detectors 816*a*-816*d*, although the number of light detectors 816*a*-*d* may vary. Light detectors 816*a*-816*d* are arranged such that a horizontal centerline is substantially parallel to the horizontal x-axis and passes through the center point of each light detector 816*a*-816*d*. A first light detector 816*a* and a last light detector 816*d* (e.g., the light detectors which are farthest apart relative to the horizontal x-axis, are used to define a central bisecting line equally dividing the distance between light detectors 816*a* and 816*d*. This central bisecting line is parallel to the vertical y-axis, and is arranged such that a distance x3 from the center point of detector 816*a* to the central bisecting line is substantially equal to a distance x4 from the center point of light detector 816*d* to the central bisecting line equally dividing the distance between light detectors 816*a* and 816*d*. That is, central bisecting line equally dividing the distance between light detectors 816*a* and 816*d* is arranged to pass through a central midpoint between the center point of light detector 816*a* and the center point of light detector 816*d* such that central bisecting line equally dividing the distance between light detectors 816*a* and 816*d* is substantially perpendicular to horizontal centerline passing through the center of at least one of light detectors 816*a-d*.

As shown, a center point of a first source 810*a* and the center point of first detector 816*a* are aligned along a centerline that is substantially parallel to the vertical y-axis. Similarly, a center point of a second light source 810*b* and the center point of the last detector 816*d* are aligned along a centerline that is substantially parallel to the vertical y-axis. It should be appreciated, however, that centerline may not necessarily pass through the center point of the first detector 816*a*, and the centerline may not necessarily pass through the center point of last detector 816*d*. That is, the vertical centerline passing through the center point of the light source 810*a* and/or the center point of the light detector 816*a* is effectively a line that is substantially parallel to the vertical y-axis and passes through the first light source 810*a*, while the vertical centerline passing through the light source 810*b* is effectively a line that is substantially parallel to the vertical y-axis.

A distance x1 between the centerline passing through light source 810*a* or light detector 816*a* and the central bisecting line equally dividing the distance between light detectors 816*a* and 816*d* is not equal to a distance x2 between the vertical centerline passing through light source 810*b* and the central bisecting line equally dividing the distance between light detectors 816*a* and 816*d*. In other words, first source 810*a* and the second source 810*b* are not equidistant from the central bisecting line equally dividing the distance between light detectors 816*a* and 816*d*. Hence, light sources 810*a* and 810*b* are positioned in an offset or unbalanced orientation relative to the horizontal x-axis.

Light sources are typically arranged to emit light of specific wavelengths. As discussed above, light of a lower wavelength emitted by a source may have a wavelength of approximately 690 nanometers, while light of a higher wavelength emitted by the source may have a wavelength of approximately 830-nanometers. In some embodiments, a first light source (e.g., 810*a* or 810*b*) may include a laser diode or a light emitter diode that produces light at a wavelength of approximately 690 nanometers as well as a laser diode that produces light at a wavelength of approximately 830 nanometers. Similarly, a second source may include a laser diode that produces light at a wavelength of approximately 690 nanometers as well as a laser diode that produces light at a wavelength of approximately 830 nanometers.

FIG. 24A shows some other simplified examples of another sensor head of a sensor probe unit with respective configurations of light emitters and light detectors, according to some embodiments. In some embodiments, sensor head 2402 includes one or more light sources 810*a* and 810*b* as well as one or more light detectors 816*a* and 816*b* that are arranged as shown in FIG. 24A. In some embodiments where sensor head 2402 includes two light sources and two light detectors, the arrangement of these light sources 810*a*-810*b* and light detectors 816*a*-816*b* is devised so that this arrangement produces four different distances between each of the light sources 810*a*-810*b* and each of the light detectors 816*a*-816*b*. As shown in FIG. 24A, the two detectors 816*a* and 816*b* are arranged along a first line, and the two light sources 810*a* and 810*b* are arranged along a second line that is collinear with the first line. In some embodiments, this implementation shown in FIG. 24A provides four pairs each containing a source and a detector that is spaced apart from the corresponding source at a distance value. In some of these embodiments, these four pairs provide four different distance values at least some of which are used in the determination of oxygen saturation.

Figure 24B:
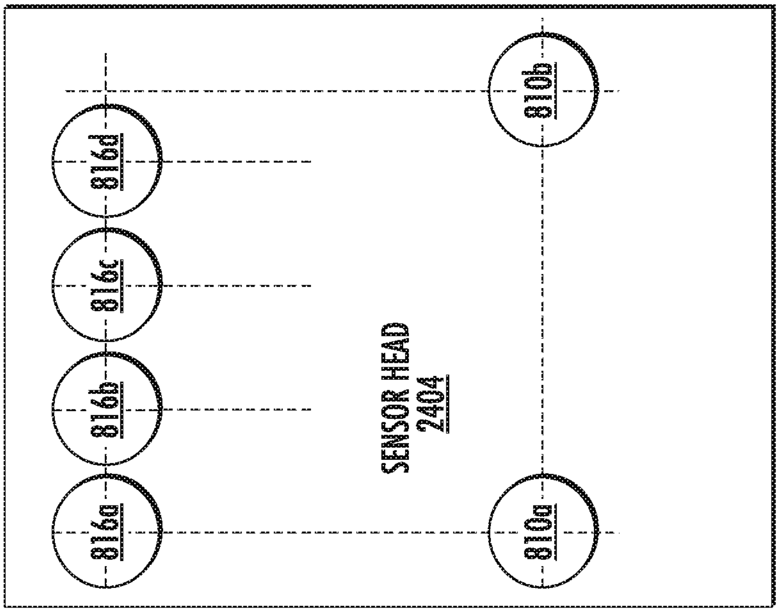

FIG. 24B shows another example sensor head 2404, according to some embodiments. A sensor head 2404 includes four light detectors 816*a*-816*d*, although the number of light detectors 816*a*-816*d* may vary. Light detectors 816*a*-816*d* are arranged such that a horizontal centerline is substantially parallel to the horizontal x-axis and passes through the center point of each light detector 816*a*-816*d*. A first light detector 816*a* and a last light detector 816*d* (e.g., the light detectors which are farthest apart relative to the horizontal x-axis), are used to define a central bisecting line equally dividing the distance between light detectors 816*a* and 816*d*. This central bisecting line is parallel to the vertical y-axis, and is arranged such that a distance x3 from the center point of detector 816*a* to the central bisecting line is substantially equal to a distance x4 from the center point of light detector 816*d* to the central bisecting line equally dividing the distance between light detectors 816*a* and 816*d*. That is, central bisecting line equally dividing the distance between light detectors 816*a* and 816*d* is arranged to pass through a central midpoint between the center point of light detector 816*a* and the center point of light detector 816*d* such that central bisecting line equally dividing the distance between light detectors 816*a* and 816*d* is substantially perpendicular to horizontal centerline passing through the center of at least one of light detectors 816*a*-816*d*. As shown in FIG. 24B, the four detectors 816*a*-816*d* are arranged alone a first line, and the two light sources 810*a* and 810*b* are arranged alone a second line that is parallel with the first line. In some embodiments, this implementation shown in FIG. 24B provides eight pairs each containing a source and a detector that is spaced apart from the corresponding source at a distance value. In some of these embodiments, these eight pairs provide eight different distance values at least some of which are used in the determination of oxygen saturation.

As shown, a center point of a first source 810*a* and the center point of first detector 816*a* are aligned along a centerline that is substantially parallel to the vertical y-axis. Nonetheless, a center point of a second light source 810*b* is offset both horizontally and vertically from the center point of the last detector 816*d*. It should be appreciated, however, that centerline may not necessarily pass through the center point of the first detector 810*a*, and the centerline may not necessarily pass through the center point of last detector 816*d*. That is, the vertical centerline passing through the center point of the light source 810*a* and/or the center point of the light detector 816*a* is effectively a line that is substantially parallel to the vertical y-axis and passes through the first light source 810*a*, while the vertical centerline passing through the light source 810*b* is effectively a line that is substantially parallel to the vertical y-axis.

A distance x1 between the centerline passing through light source 810*a* or light detector 816*a* and the central bisecting line equally dividing the distance between light detectors 816*a* and 816*d* is not equal to a distance x2 between the vertical centerline passing through the light source 810*b* and the central bisecting line equally dividing the distance between light detectors 816*a* and 816*d*. In other words, first source 810*a* and second source 810*b* are not equidistant from the central bisecting line equally dividing the distance between light detectors 816*a* and 816*d*. Hence, light sources 810*a* and 810*b* are positioned in a balanced orientation along the horizontal x-axis.

Light sources are typically arranged to emit light of specific wavelengths. As discussed above, light of a lower wavelength emitted by a source may have a wavelength of approximately 690 nanometers, while light of a higher wavelength emitted by the source may have a wavelength of approximately 830-nanometers. In some embodiments, a first light source (e.g., 810*a* or 810*b*) may include a laser diode that produces light at a wavelength of approximately 690 nanometers as well as a laser diode that produces light at a wavelength of approximately 830 nanometers. Similarly, a second source may include a laser diode that produces light at a wavelength of approximately 690 nanometers as well as a laser diode that produces light at a wavelength of approximately 830 nanometers.

Figure 25:
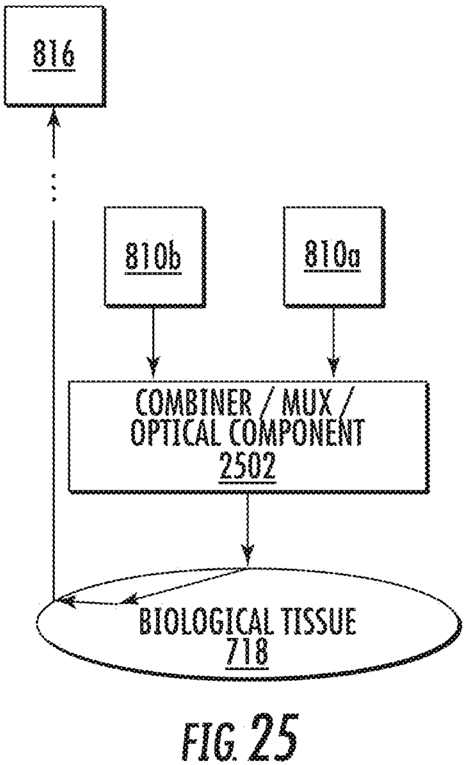
FIG. 25 shows a simplified schematic diagram of a sensor probe unit comprising light emitters and a light detector, according to some embodiments.

FIG. 25 shows a simplified schematic diagram of a sensor probe unit comprising light emitters and a light detector, according to some embodiments. More specifically, FIG. 25 shows two light sources 810*a* and 810*b* that respectively emit light beams, signals, or pulses into a combiner, a multiplexer, or an optical element (e.g., a convex lens, a concave mirror, and others) 2502 which then relays the light beams, signals, pulses to a biological tissue 718. A portion of the light beams, signals, pulses are reflected or refracted off or from within the biological tissue 718 and collected by one or more light detectors 816.

Figure 26:
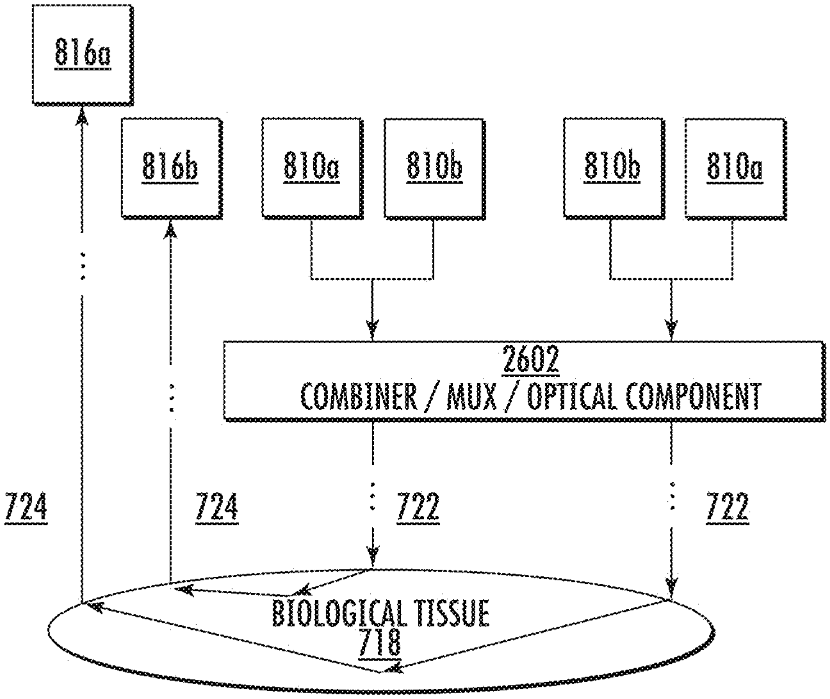
FIG. 26 shows another simplified schematic diagram of another sensor probe unit comprising light emitters and a light detector, according to some embodiments.

FIG. 26 shows another simplified schematic diagram of another sensor probe unit comprising light emitters and a light detector, according to some embodiments. More specifically, the example sensor probe unit shown in FIG. 26 includes one or more pairs of light sources 810*a* and 810*b*. In some embodiments, each pair of light sources emits a plurality of light beams, signals, or pulses of a plurality of different wavelengths and may be implemented as a multi-frequency laser that emits light beams, signals, or pulses at different wavelengths.

These one or more light sources (each emitting light beams, signals, or pulses of a plurality of wavelengths) respectively emit light beams, signals, or pulses that are forwarded into a combiner, multiplexer, or optical component 2602 which the relays the combined, multiplexed, or converged light beams, signals, or pulses 722 towards the biological tissue 718. The combined, multiplexed, or converged light beams, signals, or pulses 722 reflect off the exterior surfaces or from within the biological tissue 718, and at least a portion of the reflected or refracted light beams, signals, or pulses 724 is then detected and collected by one or more light detectors (e.g., 816*a* or 816*b* in FIG. 26).

In some embodiments, each light source emitting light beams, signals, or pulses 724 with a plurality of different wavelengths may be separately combined, multiplexed, or converged into a corresponding combined, multiplexed, or converged light beam, signal, or pulse 722 that separately reflects off the exterior surfaces or from within the biological tissue 718 to form a reflected or refracted light beam, signal, or pulse 724. In some other embodiments, two or more light sources each emitting light beams, signals, or pulses 724 with a plurality of different wavelengths may be jointly combined, multiplexed, or converged into a corresponding combined, multiplexed, or converged light beam, signal, or pulse 722.

Figure 27:
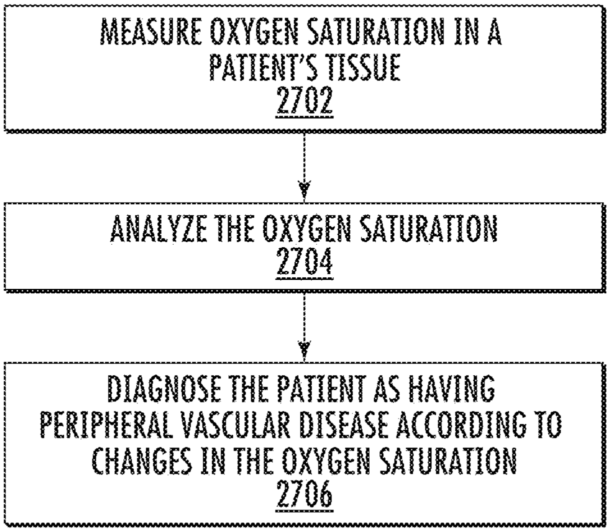
FIG. 27 shows a high-level block diagram for diagnosing a patient at least by monitoring viability of a biological tissue, according to some embodiments.

FIG. 27 shows a high-level block diagram for diagnosing a patient at least by monitoring viability of a biological tissue, according to some embodiments. At 2702, oxygen saturation in tissue of a patient during recovery from ischemia is measured. The oxygen saturation in the tissue during the recovery is analyzed at 2704.

At 2706, the patient is diagnosed as having peripheral vascular disease according to changes in the oxygen saturation during the recovery. The changes in oxygen saturation can be measured in various ways. In one embodiment, the changes in oxygen saturation are measured by the rate of change of oxygen saturation during recovery from ischemia or from an exercise challenge.

Figure 28:
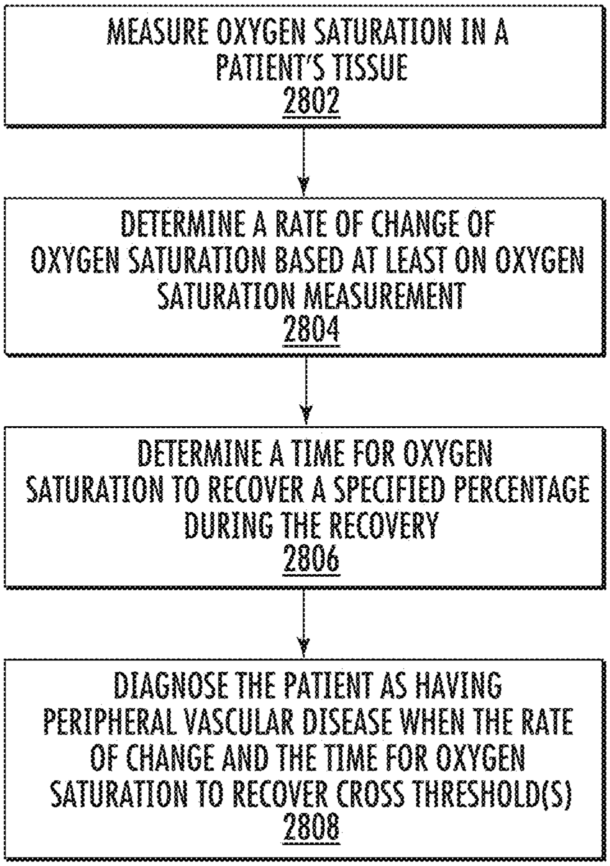
FIG. 28 shows another high-level block diagram for diagnosing a patient at least by monitoring viability of a biological tissue, according to some embodiments.

FIG. 28 shows another high-level block diagram for diagnosing a patient at least by monitoring viability of a biological tissue, according to some embodiments. At 2802, oxygen saturation in tissue of a patient during recovery from ischemia is measured. A rate of change of oxygen saturation during the recovery from an ischemia challenge or an exercise challenge may be determined based at least in part upon the oxygen saturation measurement at 2804. The rate of change may be determined as described previously. At 2806, a time for oxygen saturation to recover a specified percentage during the recovery is determined. The time may be determined as discussed previously with reference to, for example, FIG. 27.

At 2808, the patient may be diagnosed as having peripheral vascular disease if the rate of change and the time for oxygen saturation to recover cross thresholds. By utilizing multiple methods of measuring changes in oxygen saturation during recovery, greater accuracy in diagnosing peripheral vascular disease can be obtained.

Figure 29:
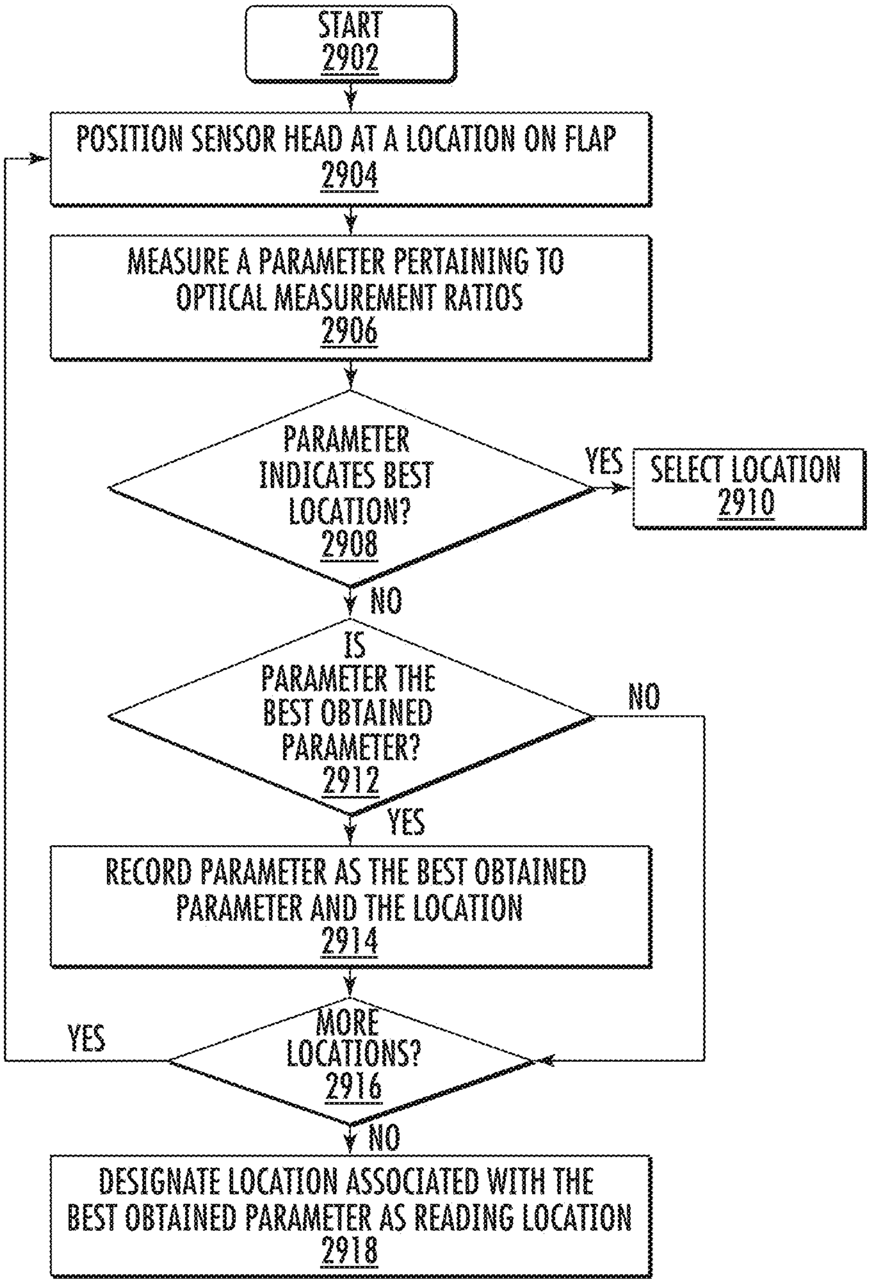
FIG. 29 shows a more detailed block diagram for positioning a sensor probe unit for monitoring viability of a biological tissue, according to some embodiments.

FIG. 29 shows a more detailed block diagram for positioning a sensor probe unit for monitoring viability of a biological tissue, according to some embodiments. More specifically, FIG. 29 shows a method of identifying a location (e.g., a better or substantially best location) for obtaining oxygen saturation level readings in accordance with an embodiment of the present invention. A process of identifying a location begins at 2902 and proceeds to 2094 in which a sensor head is positioned at a location on flap. It should be appreciated that although the flap may generally be a transplanted flap, the flap may instead be a potential flap which has not yet been procured. Additionally, in lieu of a flap, the tissue onto which a sensor head is positioned may instead be a transplanted digit.

Once the sensor head is positioned at a location, light is sent through the sensor head and reflected or refracted through the flap back into the sensor head, and a measurement of a parameter (e.g., a Q factor) pertaining to optical measurement ratios may be obtained at 2906. In some embodiments, a parameter that is constructed from optical measurement data obtained through the sensor head may be obtained. A Q factor comprises a parameter associated with the ratios of optical measurements taken using the sensor head.

Generally, the better or best approximate location for obtaining measurements of oxygen saturation levels may be a location in which a plurality of ratios of optical measurements all substantially equal one. By way of example, for a system with two sources and four detectors, a Q factor may be defined as follows for each wavelength at which light is transmitted by the sources.

Factors include wavelength, an optical measurement at a detector DI when a source S1 with a wavelength, and optical measurement at detector D1 when source S2 with a wavelength, and so forth. When each of the ratios has an approximate value of one, the location at which that occurs may be considered to be a best approximate location for obtaining measurements. The indication is that the sensor head is in good contact with tissue, that the tissue is highly homogenous, and that the oximeter of which the sensor head is a part is in good working order. It should be appreciated that for each wavelength, there may be a corresponding Q factor. Hence, for a system in which there are two wavelengths of light produced by light sources, there are two Q factors.

After a Q factor or Q factors are measured at 2906, the process flow proceeds to 2908 in which it is determined whether the Q factor or Q factors indicate that the current location of the sensor head is a best approximate location. For example, it is determined whether a Q factor has a value of approximately one (1). If the indication is that the sensor head is in a best approximate location, the location at which the sensor head is positioned is selected 2910 as the location to be used in reading oxygen saturation levels. Once the location is selected, the process of selecting a location is completed.

Alternatively, if it is determined 2908 that the Q factor does not indicate a best approximate location, the implication is that the Q factor has a value that is not approximately equal to one (1). In some embodiments, it is determined at 2912 whether the Q factor is the best obtained Q factor. Such a determination may be based on whether the Q factor obtained via measurements at 2906 has a value that is closest to one of all previously obtained Q factors. If it is determined that the Q factor is the best obtained Q factor, then it is noted at 2914 that the Q factor is the best obtained Q factor. Further, the location associated with the Q factor is noted, e.g., stored in a memory. Then, at 2916, a determination is made as to whether there are more locations to test, e.g., to identify a best approximate location for obtaining readings of oxygen saturation levels.

If the determination at 2916 is that there are more locations to test, then process flow returns to 2904 in which the sensor head is positioned at a new location on the flap. Alternatively, if it is determined that there are no more locations to test, the location associated with the best Q factor is selected at 2918 as the location to be used in reading oxygen saturation levels. After the location is selected, the process of selecting a location is completed.

Returning to 2912, if it is determined that the Q factor obtained at 2906 is not the best obtained Q factor, the indication is that a previously obtained Q factor identified a better location for obtaining readings than the current location at which the sensor head is placed. Accordingly, process flow moves directly to 2916 and a determination of whether there are more locations to test.

When there is an adequate blood supply provided to a transplanted flap, the survivability of the transplanted flap is generally increased. Blood is supplied via an artery or arteries to the transplanted flap. In order for blood to be supplied to a flap after transplant surgery, the flap itself is generally coupled to at least one artery that is, in effect, severed when the flap is removed from a donor site.

Figure 30:
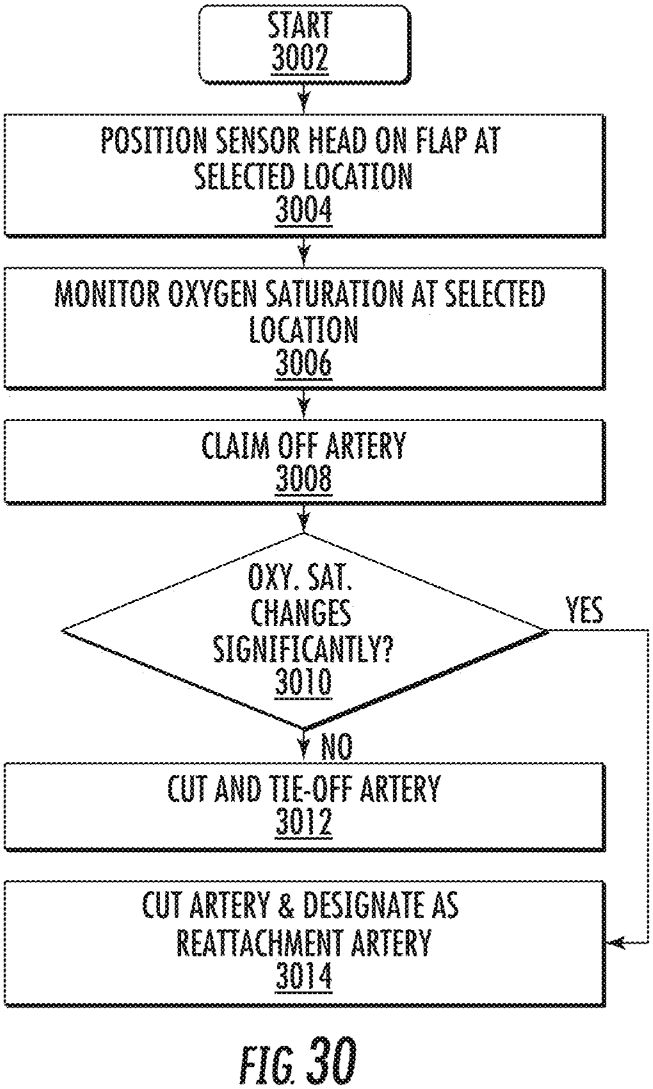
FIG. 30 shows a more detailed block diagram for operating on a patient based at least in part upon monitored viability of a biological tissue, according to some embodiments.

FIG. 30 shows a more detailed block diagram for operating on a patient based at least in part upon monitored viability of a biological tissue, according to some embodiments. More specifically, FIG. 30 shows a method of utilizing an oximeter to characterize an artery in a flap that is to be removed from a host site of a body will be described in accordance with an embodiment of the present invention. The process of characterizing an artery begins at 3002 and proceeds to 3004 in which a sensor head, e.g., a sensor head associated with an oximeter apparatus, is placed on a potential flap at a selected location. The selected location may be substantially any suitable location. Suitable locations may include, but are not limited to, a location on the flap at which a Q factor has a value of approximately one or a location that is relatively distant from an artery that is believed to provide significant blood supply to the flap. 3006, the oxygen saturation level at the selected location is monitored, as for example substantially continuously by maintaining contact between the sensor head and a top surface of the flap.

After the oxygen saturation level at the selected location is monitored, e.g., monitored long enough to determine a substantially steady-state oxygen saturation level, an artery that supplies blood to the flap is clamped off or otherwise pinched off at 3008. Once the artery is clamped off, and blood flow to the flap via the artery is effectively terminated, it is determined at 3010 whether the monitored oxygen saturation level changes significantly. For example, a determination is made as to whether there is a significant drop in the monitored oxygen level at the selected location. In general, a drop of approximately twenty percent or more in an oxygen saturation level, e.g., from approximately fifty percent to approximately thirty percent, is considered to be a significant drop, though the percentage drop may vary.

If it is determined that there is a significant change in the oxygen saturation level, the indication is that the artery is likely to supply a significant amount of blood to the flap. As such, the artery may be appropriate as an artery to use as a reattachment artery, e.g., as an artery that may be attached to another artery near a transplant site to provide a blood supply to the flap, when the flap is transplanted. Hence, 3014, the artery is cut and is designated as a reattachment artery. After the artery is cut, the process of characterizing the artery is completed.

Returning to 3010, if it is determined that the oxygen saturation level at the selected location does not change significantly in response to the artery being clamped off, the implication is that the artery is not a significant provider of blood to the flap. Therefore, process flow moves from 3010 to 3012 in which the artery is cut and tied off. Once the artery is cut and tied off, the process of characterizing the artery is completed.

FIG. 31 shows a more detailed block diagram for diagnosing a patient based at least in part upon monitored viability of a biological tissue, according to some embodiments.

More specifically, FIG. 31 shows a method of measuring oxygen saturation level of the intestine, brain, muscle, kidney, or other parts suitable for measurements using a device in accordance with the present invention and determining if the patient suffers from intestinal ischemia in these embodiments. A specific flow is presented, but it should be understood that the invention is not limited to the specific flows and steps presented. A flow of the invention may have additional acts (not necessarily described in this application), different acts which replace some of the steps presented, fewer steps or a subset of the steps presented, or steps in a different order than presented, or any combination of these. Further, the acts in other implementations of the present invention may not be exactly the same as the steps presented and may be modified or altered as appropriate for a particular application or based on the data.

To measure oxygen saturation values of a tissue (e.g., a mucosal surface of the intestine), a doctor inserts a catheter device or endoscopic device into a gastrointestinal tract of a patient, either through the mouth or anus. Alternatively, to measure oxygen saturation values of a serosal surface of the intestine or mesentery, the doctor punctures an outer tissue (e.g., skin) with a needle sensor device into an abdominal cavity. The device may be guided inside the body cavity with an aid of ultrasound, MRI, or light delivering element of the endoscopic device as described above.

At 3102, when the tip of the device reaches a desired location in the intestine or mesentery, the sensor probe at the tip of the device may be manipulated to contact a target tissue. When the sensor probe makes a proper contact with the target tissue, then the computer which is connected to the sensor probe via optical structures will indicate that the signal quality factor is acceptable or within a normal range.

At 3104, once the tip of the sensor probe makes a proper contact with the target tissue, a computer (e.g., console) directs a signal emitter (connected to the sensor probe and the computer) to transmit light to the sensor probe, and into the target tissue. After the light is transmitted into the tissue, some of the light is reflected or refracted off of the tissue. Typically, the signal emitter transmits light having a wavelength between about 600 nanometers to about 900 nanometers. In a specific implementation, the signal emitter transmits an optical signal having two or more different wavelengths to be transmitted through the sensor probe, where a first wavelength is about 690 nanometers, and a second wavelength is about 830 nanometers.

At 3106, a detector (connected to the sensor probe and the computer) detects the light reflected or refracted off of the target tissue. The reflected or refracted light or data therefor may be wirelessly transmitted at 3108 from the sensor probe to a system unit (e.g., a medical device system (e.g., 102 in FIG. 1).

At 3110, the computer or the system unit determines the oxygen saturation of the target tissue based at least in part upon this reflected or refracted light or data therefor.

At 3112, the system unit or the computer performs a comparison between the measured oxygen saturation of the target tissue and a threshold value.

A normal range of oxygen saturation for the intestine or mesentery may vary between about 60 and 90 percent. Thus, a threshold value for determining if a region in the intestine is suffering from ischemia may be set at 60 percent or below. For example, the threshold value may be set at 59, 55, 50, 45, 40, 35, 30, 25, 20, 15, 10, 5, 0 percent, or any other numbers in this range. The threshold value can vary depending on which region of the intestine was tested for oxygen saturation level. Accordingly, depending on the intestinal region being tested or other factors, the threshold value may be set at a different level.

The process flow shown in FIG. 31 may be repeated after moving the sensor probe to different locations in the intestine or mesentery.

At 3114, if a patient presents various symptoms described above and if the oxygen saturation measurements from one or more regions of the patient's intestine or mesentery are lower than a threshold value, then the patient may be diagnosed as having intestinal ischemia. Because embodiments of the present invention directly assess the oxygenation state of the intestine and mesentery, a doctor may make a more definitive diagnosis of intestinal ischemia in a patient.

The flow diagram shown in FIG. 31 may also be applied in monitoring oxygen saturation level of the intestine or mesentery during a surgical procedure. If symptoms of intestinal ischemia are severe in a patient and the doctor suspects that a portion of the intestine is infracted (dead), the doctor may decide to perform a resection of a dead tissue followed by an anastomosis. In determining which intestinal tissue may be viable or nonviable, the doctor can use the devices of the present invention, rather than relying on subjective criteria such as color of the intestine.

In determining which intestinal tissue is viable or nonviable during a surgery, the doctor can follow steps 3102 through 3112 in the flow diagram provided in FIG. 31. As stated above, the threshold value for viability of a tissue may differ depending on tissue type, age of the patient, or the patients' medical history. For example, a threshold value for viability of the colon may be selected at 40 percent oxygen saturation level, where a threshold value for viability of the small intestine may be selected at 35 percent oxygen saturation level.

Furthermore, the flow diagram shown in FIG. 31 may be used to monitor oxygen saturation level of the intestine or mesentery after surgery or other treatment. Even after an anastomosis procedure, there is a risk that rejoined portions of the intestine may fail if there is too much strain or limited vascular supply to the rejoined portions. Because the devices of the present invention can monitor the oxygenation state of the intestine noninvasively, they may be applied to determine if the joined portions of the intestine are adequately oxygenated and healthy.

In another aspect of the invention, the method in accordance with the present invention includes marking a portion in the intestine or mesentery after a sensor probe makes oxygen saturation measurements. Prior to a surgical procedure, the doctor may desire to notate a portion of the intestine that is viable or nonviable based on oxygen saturation measurements of the tissue. The devices with a marking mechanism in accordance with the present invention may be used to mark either viable or nonviable portions of the intestine prior to a resection procedure. By clearly marking the tissue prior to or during the surgery, the doctor can clearly view which portion of the intestine needs to be resected or treated. At 3116, the diagnosis result may be displayed in a display of a computing device.

Figure 32:
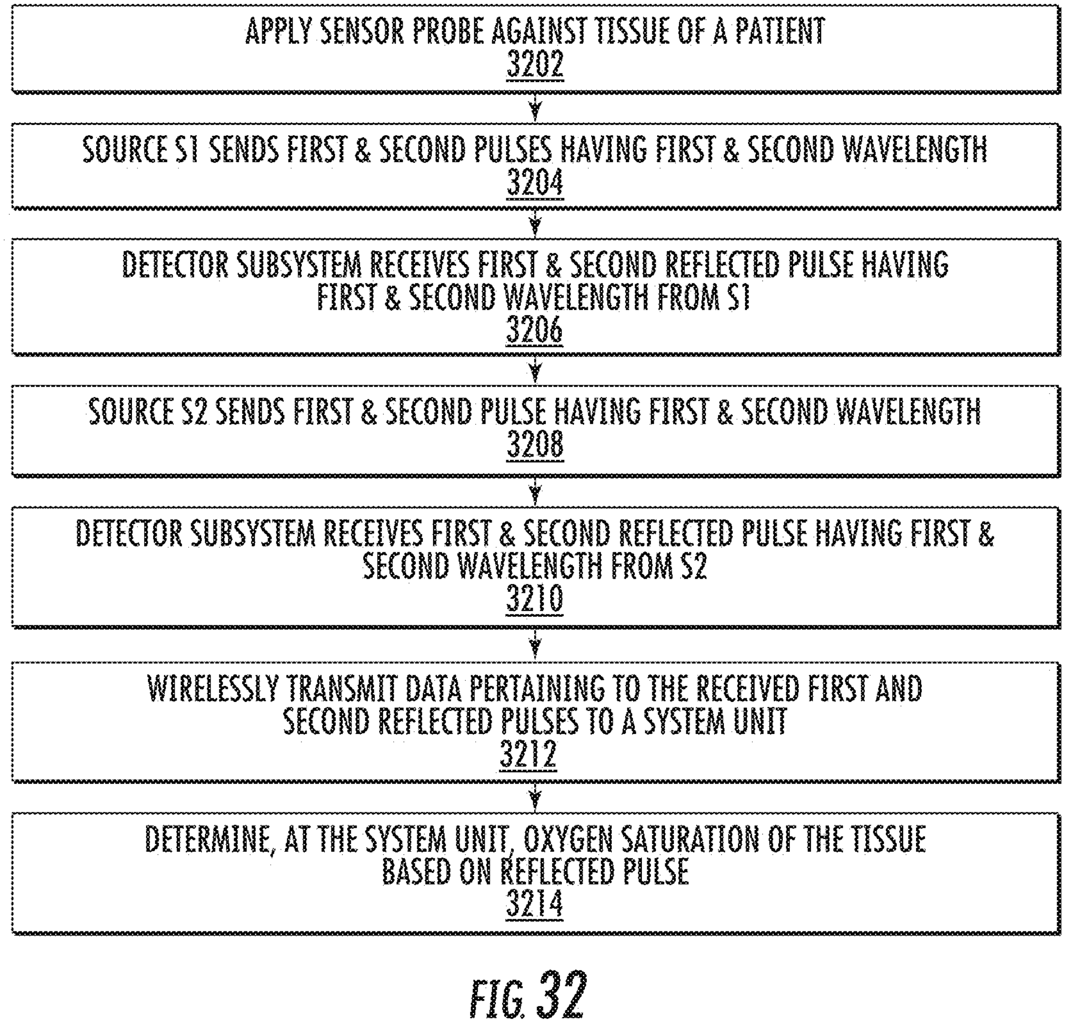
FIG. 32 shows another more detailed block diagram for monitoring viability of a biological tissue, according to some embodiments.

FIG. 32 shows another more detailed block diagram for monitoring viability of a biological tissue, according to some embodiments. A sensor probe (e.g., a sensor head of a sensor probe system 704, a sensor probe unit 706, and others) may be applied at 3202 against a biological tissue of a patient. At 3204, a first light source S1 may transmit first and second light pulses, signals, or beams respectively having a first wavelength and a second wavelength that has a different wavelength value (and hence frequency) from that of the first wavelength. In some embodiments, the first light source S1 may comprise a multi-line laser that emits lights having multiple different wavelengths. The first and second light beams, signals, or pulses may be directed towards a biological tissue and reflect from the exterior surfaces of the biological tissue in the form of first and second reflected or refracted light beams, signals, or pulses.

At 3206, a light detector subsystem may receive a first reflected or refracted light pulse, beam, or signal having a first wavelength and a second reflected or refracted light pulse, beam, or signal having a second wavelength that has a different wavelength value (and hence frequency) from that of the first wavelength. For example, at least a respective portion of the first and second reflected or refracted light beams, signals, or pulses may reflect off the exterior surface of the biological tissue and is then collected by the light detector subsystem at 3206.

At 3208, a second light source S2 may transmit third and fourth light pulses, signals, or beams respectively having a third wavelength and a fourth wavelength that has a different wavelength value (and hence frequency) from that of the third wavelength. In some embodiments, the second light source S2 may comprise a multi-line laser that emits lights having multiple different wavelengths. In some embodiments, the first wavelength may be identical to one of the third and the fourth wavelength, and the second wavelength may be identical to one of the third and the fourth wavelength but different from the first wavelength. In some other embodiments, the first and second wavelengths have wavelength values that are different from those of the third and fourth wavelengths. The third and fourth light beams, signals, or pulses may be directed towards a biological tissue and reflect from the exterior surfaces of the biological tissue in the form of third and fourth reflected or refracted light beams, signals, or pulses.

At 3210, the light detector subsystem may receive a third reflected or refracted light pulse, beam, or signal having a third wavelength and a fourth reflected or refracted light pulse, beam, or signal having a fourth wavelength that has a different wavelength value (and hence frequency) from that of the third wavelength. For example, at least a respective portion of the third and fourth reflected or refracted light beams, signals, or pulses may reflect off the exterior surface of the biological tissue and is then collected by the light detector subsystem at 3210.

The aforementioned reflected or refracted light beams, signals, or pulses (e.g., the first, second, third, and fourth reflected or refracted light beams, signals, or pulses) may be wirelessly transmitted to a system unit (e.g., a medical sensor probe electronic module, a medical device system, and others) at 3212.

A determination may be made at the system unit to decide oxygen saturation of the biological tissue at 3214. In some embodiments, the determination at 3214 may be made based at least in part upon the reflected or refracted light beams, signals, or pulses.

Various techniques shown in the above figures and described above are useful in diagnosing intestinal ischemia in a patient, as well as in monitoring and marking a tissue with a poor oxygen saturation level in the intestine or mesentery. Because embodiments of the invention can directly assess the oxygenation state of a full thickness of the intestine, they provide a better diagnostic tool in determining an ischemic condition of the intestine or mesentery at an earlier stage. Early diagnosis of intestinal ischemia is a key to successfully treating the disease. Embodiments of the invention contribute, among other things, in solving the problems related to a diagnosis of intestinal ischemia, locating ischemic tissue portions, as well as improving oxygen saturation measurements of the intestinal or mesentery tissue.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

What is claimed is:

1. A device comprising:

(A) a first enclosure of an oximeter sensor comprising:

(1) a first source structure and a second source structure arranged on a first line on a first planar surface of the first enclosure, wherein the first source structure comprises a first source structure side, inside the first enclosure, and a second source structure side, outside of the first enclosure, and the second source structure comprises a third source structure side, inside the first enclosure, and a fourth source structure side, outside of the first enclosure;

(2) a first emitter circuit, wherein the first emitter circuit emits light having a first wavelength, and the first emitter circuit is associated with the first source structure;

(3) a second emitter circuit, wherein the second emitter circuit emits light having a second wavelength, which is different from the first wavelength, and the second emitter circuit is associated with the first source structure;

(4) a third emitter circuit, wherein the third emitter circuit emits light having the first wavelength, and the third emitter circuit is associated with the second source structure;

(5) a fourth emitter circuit, wherein the fourth emitter circuit emits light having the second wavelength, and the fourth emitter circuit is associated with the second source structure, the first and second emitter circuits are positioned within the first enclosure such that light emitted by either the first emitter circuit or the second emitter circuit will pass through the first source structure from the first source structure side to the second source structure side in a direction away from the first planar surface, and the third and fourth emitter circuits are positioned within the first enclosure such that light emitted by either the third emitter circuit or the fourth emitter circuit will pass through the second source structure from the third source structure side to the fourth source structure side in a direction away from the first planar surface;

(6) a first detector structure and a second detector structure arranged on a second line on the first planar surface of the first enclosure, where the second line is not collinear or parallel with the first line, and the second line does not pass through the first source structure or the second source structure;

(7) a first detector circuit, wherein the first detector circuit receives light that passes through the first detector structure and not the second detector structure;

(8) a second detector circuit, wherein the second detector circuit receives light that passes through the second detector structure and not the first detector structure; and (9) a front-end circuit, coupled to the first and second emitter circuits and the first and second detector circuits;

(B) a second enclosure of the oximeter sensor, wherein the second enclosure is a separate and independent enclosure from the first enclosure, the second enclosure comprises:

(10) a processor;

(11) a memory, coupled to the processor;

(12) a first wireless communication circuit, coupled to the processor and memory; and

(13) a battery, coupled to the processor, memory, and first wireless communication circuit, wherein the battery supplies power to the processor, memory, and first wireless communication circuit via a connection internal to the second enclosure; and (C) an electrical cable, extending externally between the first and second enclosures, wherein the electrical cable couples the front-end circuit of the first enclosure to the processor, memory, first wireless communication circuit, and battery of the second enclosure, and the battery supplies power to the front-end circuit, first and second emitter circuits, and first and second detector circuits via the electrical cable.

2. The device of claim 1 wherein a first distance is between the first source structure and the first detector structure, a second distance is between the first source structure and the second detector structure, a third distance is between the second source structure and the first detector structure, and a fourth distance is between the second source structure and the second detector structure, and the first, second, third, and fourth distances are different from each other.

3. The device of claim 1 wherein the first enclosure comprises a third detector structure and a fourth detector structure arranged on the second line on the first planar surface of the first enclosure.

4. The device of claim 1 wherein the first and second source structures and the first and second detector structures comprise circular cross sections.

5. The device of claim 1 wherein the first and second source structures and the first and second detector structures comprise a polymer material.

6. The device of claim 1 wherein the first and second source structures and the first and second detector structures comprise optical fibers.

7. The device of claim 1 comprising:

a beam combiner comprising a first input, second input, and an output, wherein the first input of the beam combiner is optically coupled to the first emitter circuit, the second input of the beam combiner is optically coupled to the second emitter circuit, and the output of the beam combiner is optically coupled to the first source structure.

8. A system comprising:

the device of claim 1; and a console comprising a processor, memory, screen, and second wireless communication circuit, wherein via the second wireless communication circuit, the console wirelessly connects to the first wireless communication circuit to establish a wireless communication link, the first wireless communication circuit transmits oxygen saturation information over the wireless communication link, and the console displays a graph on the screen based at least in part on the oxygen saturation information received from the device.

9. The device of claim 1 wherein the first and second emitter circuits are positioned within the first enclosure such that while light emitted by either the first emitter circuit or the second emitter circuit is passing through the first source structure, that light will not pass through the second source structure.

10. The device of claim 9 wherein the third and fourth emitter circuits are positioned within the first enclosure such that while light emitted by either the third emitter circuit or the fourth emitter circuit is passing through the second source structure, that light will not pass through the first source structure.

11. The device of claim 1 wherein a third line passes through the first source structure and the first detector structure, a fourth line passes through the second source structure and the second detector structure, and the third and fourth lines are parallel.

12. A device comprising:

(A) a first enclosure of an oximeter sensor probe comprising:

(1) a first source structure and a second source structure arranged on a first line on a first planar surface of the first enclosure, wherein the first source structure comprises a first source structure side, inside the first enclosure, and a second source structure side, outside of the first enclosure, and the second source structure comprises a third source structure side, inside the first enclosure, and a fourth source structure side, outside of the first enclosure;

(2) a first emitter circuit, wherein the first emitter circuit emits light having a first wavelength, and the first emitter circuit is associated with the first source structure;

(3) a second emitter circuit, wherein the second emitter circuit emits light having a second wavelength, which is different from the first wavelength, and the second emitter circuit is associated with the first source structure;

(4) a third emitter circuit, wherein the third emitter circuit emits light having the first wavelength, and the third emitter circuit is associated with the second source structure;

(5) a fourth emitter circuit, wherein the fourth emitter circuit emits light having the second wavelength, and the fourth emitter circuit is associated with the second source structure, the first and second emitter circuits are positioned within the first enclosure such that light emitted by either the first emitter circuit or the second emitter circuit will pass through the first source structure from the first source structure side to the second source structure side in a direction away from the first planar surface, and the third and fourth emitter circuits are positioned within the first enclosure such that light emitted by either the third emitter circuit or the fourth emitter circuit will pass through the second source structure from the third source structure side to the fourth source structure side in a direction away from the first planar surface;

(6) a first detector structure and a second detector structure arranged on a second line on the first planar surface of the first enclosure, where the second line is not collinear or parallel with the first line;

(7) a first detector circuit, wherein the first detector circuit receives light that passes through the first detector structure and not the second detector structure;

(8) a second detector circuit, wherein the second detector circuit receives light that passes through the second detector structure and not the first detector structure; and (9) a front-end circuit, coupled to the first and second emitter circuits and the first and second detector circuits;

(B) a second enclosure of the oximeter sensor probe, wherein the second enclosure is a separate and independent enclosure from the first enclosure, the second enclosure comprises:

(10) a processor;

(11) a memory, coupled to the processor;

(12) a first wireless communication circuit, coupled to the processor and memory; and

(13) a battery, coupled to the processor, memory, and first wireless communication circuit, wherein the battery supplies power to the processor, memory, and first wireless communication circuit via a connection internal to the second enclosure; and (C) an electrical cable, extending externally between the first and second enclosures, wherein the electrical cable couples the front-end circuit of the first enclosure to the processor, memory, first wireless communication circuit, and battery of the second enclosure, and the battery supplies power to the front-end circuit, first and second emitter circuits, and first and second detector circuits via the electrical cable, wherein between the first source structure and the first detector structure, there are no intervening source or detector structures, between the first source structure and the second detector structure, there are no intervening source or detector structures, between the second source structure and the first detector structure, there are no intervening source or detector structures, and between the second source structure and the second detector structure, there are no intervening source or detector structures.

13. A device comprising:

(A) a first enclosure of an oximeter sensor probe comprising:

(1) a first source structure and a second source structure arranged on a first line on a first planar surface of the first enclosure, wherein the first source structure comprises a first source structure side, inside the first enclosure, and a second source structure side, outside of the first enclosure, and the second source structure comprises a third source structure side, inside the first enclosure, and a fourth source structure side, outside of the first enclosure;

(2) a first emitter circuit, wherein the first emitter circuit emits light having a first wavelength, and the first emitter circuit is associated with the first source structure;

(3) a second emitter circuit, wherein the second emitter circuit emits light having a second wavelength, which is different from the first wavelength, and the second emitter circuit is associated with the first source structure;

(4) a third emitter circuit, wherein the third emitter circuit emits light having the first wavelength, and the third emitter circuit is associated with the second source structure;

(5) a fourth emitter circuit, wherein the fourth emitter circuit emits light having the second wavelength, and the fourth emitter circuit is associated with the second source structure, the first and second emitter circuits are positioned within the first enclosure such that light emitted by either the first emitter circuit or the second emitter circuit will pass through the first source structure from the first source structure side to the second source structure side in a direction away from the first planar surface, and the third and fourth emitter circuits are positioned within the first enclosure such that light emitted by either the third emitter circuit or the fourth emitter circuit will pass through the second source structure from the third source structure side to the fourth source structure side in a direction away from the first planar surface;

(6) a first detector structure and a second detector structure arranged on a second line on the first planar surface of the first enclosure, where the second line is not collinear or parallel with the first line;

(7) a first detector circuit, wherein the first detector circuit receives light that passes through the first detector structure and not the second detector structure;

(8) a second detector circuit, wherein the second detector circuit receives light that passes through the second detector structure and not the first detector structure; and (9) a front-end circuit, coupled to the first and second emitter circuits and the first and second detector circuits;

(B) a second enclosure of the oximeter sensor probe, wherein the second enclosure is a separate and independent enclosure from the first enclosure, the second enclosure comprises:

(10) a processor;

(11) a memory, coupled to the processor;

(12) a first wireless communication circuit, coupled to the processor and memory; and

(13) a battery, coupled to the processor, memory, and first wireless communication circuit, wherein the battery supplies power to the processor, memory, and first wireless communication circuit via a connection internal to the second enclosure; and (C) an electrical cable, extending externally between the first and second enclosures, wherein the electrical cable couples the front-end circuit of the first enclosure to the processor, memory, first wireless communication circuit, and battery of the second enclosure, and the battery supplies power to the front-end circuit, first and second emitter circuits, and first and second detector circuits via the electrical cable, wherein on a line between the first source structure and the first detector structure, there are no intervening source or detector structures, on a line between the first source structure and the second detector structure, there are no intervening source or detector structures, on a line between the second source structure and the first detector structure, there are no intervening source or detector structures, and on a line between the second source structure and the second detector structure, there are no intervening source or detector structures.

14. The system of claim 8 wherein the console comprises a tablet device.

15. A device comprising:

(A) a first enclosure of an oximeter sensor comprising:

(1) a first source structure and a second source structure arranged on a first line on a first planar surface of the first enclosure, wherein the first source structure comprises a first source structure side, inside the first enclosure, and a second source structure side, outside of the first enclosure, and the second source structure comprises a third source structure side, inside the first enclosure, and a fourth source structure side, outside of the first enclosure;

(2) a first emitter circuit, wherein the first emitter circuit emits light having a first wavelength or a second wavelength, the first wavelength is different from the second wavelength, and the first emitter circuit is associated with the first source structure;

(3) a second emitter circuit, wherein the second emitter circuit emits light having the first wavelength or the second wavelength, and the second emitter circuit is associated with the second source structure, the first emitter circuit is positioned within the first enclosure such that light emitted by the first emitter circuit will pass through the first source structure from the first source structure side to the second source structure side in a direction away from the first planar surface, and the second emitter circuit is positioned within the first enclosure such that light emitted by the second emitter circuit will pass through the second source structure from the third source structure side to the fourth source structure side in a direction away from the first planar surface;

(4) a first detector structure and a second detector structure arranged on a second line on the first planar surface of the first enclosure, where the second line is not collinear or parallel with the first line, and the second line does not pass through the first source structure or the second source structure;

(5) a first detector circuit, wherein the first detector circuit receives light that passes through the first detector structure and not the second detector structure;

(6) a second detector circuit, wherein the second detector circuit receives light that passes through the second detector structure and not the first detector structure; and (7) a front-end circuit, coupled to the first and second emitter circuits and the first and second detector circuits;

(B) a second enclosure of the oximeter sensor, wherein the second enclosure is a separate and independent enclosure from the first enclosure, the second enclosure comprises:

(8) a processor;

(9) a memory, coupled to the processor;

(10) a first wireless communication circuit, coupled to the processor and memory; and

(11) a battery, coupled to the processor, memory, and first wireless communication circuit, wherein the battery supplies power to the processor, memory, and first wireless communication circuit via a connection internal to the second enclosure; and (C) an electrical cable, extending externally between the first and second enclosures, wherein the electrical cable couples the front-end circuit of the first enclosure to the processor, memory, first wireless communication circuit, and battery of the second enclosure, and the battery supplies power to the front-end circuit, first and second emitter circuits, and first and second detector circuits via the electrical cable.

16. The device of claim 15 wherein a first distance is between the first source structure and the first detector structure, a second distance is between the first source structure and the second detector structure, a third distance is between the second source structure and the first detector structure, and a fourth distance is between the second source structure and the second detector structure, and the first, second, third, and fourth distances are different from each other.

17. The device of claim 15 wherein a third line passes through the first source structure and the first detector structure, a fourth line passes through the second source structure and the second detector structure, and the third and fourth lines are parallel.

18. A method comprising:

for an oxygen saturation sensor, providing a first enclosure comprising first electronic components;

for the oxygen saturation sensor, providing a second enclosure comprising second electronic components, wherein the second enclosure is separate and independent of the first enclosure; and coupling the first enclosure to the second enclosure via an electrical cable, extending externally to both the first and second enclosures, wherein the first electronic components of the first enclosure comprise a first emitter circuit and a second emitter circuit arranged on a first line, each coupled to the electrical cable, and a first detector circuit and a second detector circuit arranged on a second line, each coupled to the electrical cable, and the second line does not pass through a first source structure or a second source structure, the second electronic components of the second enclosure comprise a battery, coupled to the electrical cable, a controller circuit comprising a processor and memory, coupled to the battery via a connection internal to the second enclosure, and a wireless communication circuit, coupled to the battery via a connection internal to the second enclosure.

19. The method of claim 18 wherein the first electronic components comprise a front-end circuit that is coupled between the electrical cable and the at least two emitter circuits and between the electrical cable and the at least two detector circuits.

20. The method of claim 18 wherein the first enclosure comprises the first source structure and the second source structure arranged on a third line on a first planar surface of the first enclosure, the first source structure comprises a circular cross section, and the second source structure comprises a circular cross section, the first source structure comprises a first source structure side, inside the first enclosure, and a second source structure side, outside of the first enclosure, and the second source structure comprises a third source structure side, inside the first enclosure, and a fourth source structure side, outside of the first enclosure.

21. The method of claim 20 wherein the first emitter circuit emits light having a first wavelength, and the first emitter circuit is associated with the first source structure, the second emitter circuit emits light having a second wavelength, which is different from the first wavelength, and the second emitter circuit is associated with the first source structure, and the first and second emitter circuits are positioned within the first enclosure such that light emitted by either the first emitter circuit or the second emitter circuit will pass through the first source structure from the first source structure side to the second source structure side in a direction away from the first planar surface.

22. The method of claim 18 wherein while the first enclosure is positioned on a tissue to make an oxygen saturation measurement, the second enclosure can be moved relative to the first enclosure without affecting the oxygen saturation measurement.

23. A device comprising:

(A) a first enclosure of an oximeter sensor comprising:

(1) a first source structure and a second source structure arranged on a first line on a first planar surface of the first enclosure, wherein the first source structure comprises a first source structure side, inside the first enclosure, and a second source structure side, outside of the first enclosure, and the second source structure comprises a third source structure side, inside the first enclosure, and a fourth source structure side, outside of the first enclosure;

(2) a first emitter circuit, wherein the first emitter circuit emits light having a first wavelength or a second wavelength, the first wavelength is different from the second wavelength, and the first emitter circuit is associated with the first source structure;

(3) a second emitter circuit, wherein the second emitter circuit emits light having the first wavelength or the second wavelength, and the second emitter circuit is associated with the second source structure, the first emitter circuit is positioned within the first enclosure such that light emitted by the first emitter circuit will pass through the first source structure from the first source structure side to the second source structure side in a direction away from the first planar surface, and the second emitter circuit is positioned within the first enclosure such that light emitted by the second emitter circuit will pass through the second source structure from the third source structure side to the fourth source structure side in a direction away from the first planar surface;

(4) a first detector structure and a second detector structure arranged on a second line on the first planar surface of the first enclosure, where the second line is not collinear or parallel with the first line;

(5) a first detector circuit, wherein the first detector circuit receives light that passes through the first detector structure and not the second detector structure;

(6) a second detector circuit, wherein the second detector circuit receives light that passes through the second detector structure and not the first detector structure; and (7) a front-end circuit, coupled to the first and second emitter circuits and the first and second detector circuits;

(B) a second enclosure of the oximeter sensor, wherein the second enclosure is a separate and independent enclosure from the first enclosure, the second enclosure comprises:

(8) a processor;

(9) a memory, coupled to the processor;

(10) a first wireless communication circuit, coupled to the processor and memory; and

(11) a battery, coupled to the processor, memory, and first wireless communication circuit, wherein the battery supplies power to the processor, memory, and first wireless communication circuit via a connection internal to the second enclosure; and (C) an electrical cable, extending externally between the first and second enclosures, wherein the electrical cable couples the front-end circuit of the first enclosure to the processor, memory, first wireless communication circuit, and battery of the second enclosure, and the battery supplies power to the front-end circuit, first and second emitter circuits, and first and second detector circuits via the electrical cable, wherein a third line passes through the first source structure and the first detector structure, a fourth line passes through the second source structure and the second detector structure, and the third and fourth lines are parallel.

24. The device of claim 23 wherein the first enclosure comprises a third detector structure and a fourth detector structure arranged on the second line on the first planar surface of the first enclosure.

25. A system comprising:

the device of claim 23; and a console comprising a processor, memory, screen, and second wireless communication circuit, wherein via the second wireless communication circuit, the console wirelessly connects to the first wireless communication circuit to establish a wireless communication link, the first wireless communication circuit transmits oxygen saturation information over the wireless communication link, and the console displays a graph on the screen based at least in part on the oxygen saturation information received from the device.

26. The system of claim 25 wherein the console comprises at least one of a smartphone or tablet device.

* * * * *